United States Patent
LaLonde et al.

(10) Patent No.: US 8,373,556 B2
(45) Date of Patent: *Feb. 12, 2013

(54) MEDICAL DATA TRANSPORT OVER WIRELESS LIFE CRITICAL NETWORK

(75) Inventors: John R. LaLonde, Lake Elmo, MN (US); William Mass, Renton, WA (US); Kenneth P. Hoyme, Plymouth, MN (US); David C. Johnson, Inver Grove Heights, MN (US); Joe Bange, Eagan, MN (US); Mark Gryzwa, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/181,176

(22) Filed: Jul. 12, 2011

(65) Prior Publication Data

US 2011/0273287 A1    Nov. 10, 2011

Related U.S. Application Data

(63) Continuation of application No. 12/151,869, filed on May 9, 2008, now Pat. No. 7,978,062.

(60) Provisional application No. 60/967,060, filed on Aug. 31, 2007, provisional application No. 60/967,061, filed on Aug. 31, 2007, provisional application No. 60/967,062, filed on Aug. 31, 2007, provisional application No. 60/967,063, filed on Aug. 31, 2007.

(51) Int. Cl.
*G08B 1/08* (2006.01)

(52) U.S. Cl. ........... 340/539.11; 340/539.1; 340/539.12; 340/539.13; 340/573.1; 340/3.1

(58) Field of Classification Search ............. 340/539.11, 340/539.1, 539.12, 539.13, 573.1, 573.4, 340/3.1
See application file for complete search history.

(56) References Cited

U.S. PATENT DOCUMENTS

| | | | |
|---|---|---|---|
| 4,211,235 A | 7/1980 | Keller, Jr. et al. |
| 5,012,411 A | 4/1991 | Policastro et al. |
| 5,033,286 A | 7/1991 | Guardiani |
| 5,047,930 A | 9/1991 | Martens et al. |
| 5,113,869 A | 5/1992 | Nappholz et al. |

(Continued)

FOREIGN PATENT DOCUMENTS

| EP | 1681803 | 7/2006 |
|---|---|---|
| JP | 08329374 | 12/1996 |

(Continued)

OTHER PUBLICATIONS

International Preliminary Report on Patentability dated Mar. 1, 2010 from PCT Application No. PCT/US2008/010162, 13 pages.

(Continued)

*Primary Examiner* — Daryl Pope
(74) *Attorney, Agent, or Firm* — Pauly DeVries Smith & Deffner LLC

(57) ABSTRACT

A portable patient communicator (PPC) includes a portable housing that supports a processor coupled to memory for storing medical firmware and wireless radio firmware, first and second radios, a processor, and a power source. Communications between a patient implantable medical device (PIMD) and the first radio of the PPC are effected in accordance with program instructions of the medical firmware, and communications between the second radio of the PPC and the wireless network are effected in accordance with program instructions of the wireless radio firmware. Data from the PIMD is received via the first radio to which a priority level is assigned, such as in a tiered manner. A data transport mechanism is selected among disparate data transport mechanisms based at least in part on the priority level. PIMD data is transmitted to the wireless network using the selected transport mechanism via the second radio.

20 Claims, 28 Drawing Sheets

U.S. PATENT DOCUMENTS

| | | |
|---|---|---|
| 5,293,642 A | 3/1994 | Lo |
| 5,336,245 A | 8/1994 | Adams et al. |
| 5,339,824 A | 8/1994 | Engira |
| 5,383,915 A | 1/1995 | Adams |
| 5,438,983 A | 8/1995 | Falcone |
| 5,462,051 A | 10/1995 | Oka et al. |
| 5,464,012 A | 11/1995 | Falcone |
| 5,522,396 A | 6/1996 | Langer et al. |
| 5,579,775 A | 12/1996 | Dempsey et al. |
| 5,620,472 A | 4/1997 | Rahbari |
| 5,634,468 A | 6/1997 | Platt et al. |
| 5,674,249 A | 10/1997 | de Coriolis et al. |
| 5,720,770 A | 2/1998 | Nappholz |
| 5,720,771 A | 2/1998 | Snell |
| 5,749,907 A | 5/1998 | Mann |
| 5,752,976 A | 5/1998 | Duffin et al. |
| 5,759,199 A | 6/1998 | Snell |
| 5,827,180 A | 10/1998 | Goodman |
| 5,873,040 A | 2/1999 | Dunn et al. |
| 5,891,178 A | 4/1999 | Mann et al. |
| 5,899,855 A | 5/1999 | Brown |
| 5,904,708 A | 5/1999 | Goedeke |
| 6,050,940 A | 4/2000 | Braun et al. |
| 6,083,248 A | 7/2000 | Thompson |
| 6,088,594 A | 7/2000 | Kingdon et al. |
| 6,093,146 A | 7/2000 | Filangeri |
| 6,095,985 A | 8/2000 | Raymond et al. |
| 6,161,095 A | 12/2000 | Brown |
| 6,225,901 B1 | 5/2001 | Kail, IV |
| 6,282,441 B1 | 8/2001 | Raymond et al. |
| 6,287,252 B1 | 9/2001 | Lugo |
| 6,325,756 B1 | 12/2001 | Webb et al. |
| 6,330,426 B2 | 12/2001 | Brown et al. |
| 6,353,761 B1 | 3/2002 | Conley et al. |
| 6,363,282 B1 | 3/2002 | Nichols et al. |
| 6,377,843 B1 | 4/2002 | Naydenov et al. |
| 6,396,416 B1 | 5/2002 | Kuusela et al. |
| 6,398,727 B1 | 6/2002 | Bui et al. |
| 6,402,691 B1 | 6/2002 | Peddicord et al. |
| 6,405,083 B1 | 6/2002 | Rockwell et al. |
| 6,406,426 B1 | 6/2002 | Reuss et al. |
| 6,411,840 B1 | 6/2002 | Bardy |
| 6,413,213 B1 | 7/2002 | Essenpreis et al. |
| 6,418,346 B1 | 7/2002 | Nelson et al. |
| 6,428,475 B1 | 8/2002 | Shen |
| 6,434,429 B1 | 8/2002 | Kraus et al. |
| 6,442,432 B2 | 8/2002 | Lee |
| 6,450,953 B1 | 9/2002 | Place et al. |
| 6,453,200 B1 | 9/2002 | Koslar |
| 6,456,256 B1 | 9/2002 | Amundson et al. |
| 6,466,819 B1 | 10/2002 | Weiss |
| 6,470,215 B1 | 10/2002 | Kraus et al. |
| 6,477,363 B1 | 11/2002 | Ayoub et al. |
| 6,477,424 B1 | 11/2002 | Thompson et al. |
| 6,480,745 B2 | 11/2002 | Nelson et al. |
| 6,485,418 B2 | 11/2002 | Yasushi et al. |
| 6,497,655 B1 | 12/2002 | Linberg et al. |
| 6,512,944 B1 | 1/2003 | Kovtan et al. |
| 6,544,171 B2 | 4/2003 | Beetz et al. |
| 6,544,173 B2 | 4/2003 | West et al. |
| 6,553,262 B1 | 4/2003 | Lang et al. |
| 6,556,871 B2 | 4/2003 | Schmitt et al. |
| 6,558,320 B1 | 5/2003 | Causey, III et al. |
| 6,564,104 B2 | 5/2003 | Nelson et al. |
| 6,564,108 B1 | 5/2003 | Makar et al. |
| 6,569,095 B2 | 5/2003 | Eggers |
| 6,574,509 B1 | 6/2003 | Kraus et al. |
| 6,574,510 B2 | 6/2003 | Von Arx et al. |
| 6,577,899 B2 | 6/2003 | Lebel et al. |
| 6,584,356 B2 | 6/2003 | Wassmund et al. |
| 6,591,242 B1 | 7/2003 | Karp et al. |
| 6,599,250 B2 | 7/2003 | Webb et al. |
| 6,602,191 B2 | 8/2003 | Quy |
| 6,609,023 B1 | 8/2003 | Fischell et al. |
| 6,609,115 B1 | 8/2003 | Mehring |
| 6,611,206 B2 | 8/2003 | Eshelman et al. |
| 6,614,406 B2 | 9/2003 | Amundson et al. |
| 6,622,043 B1 | 9/2003 | Kraus et al. |
| 6,622,044 B2 | 9/2003 | Bange et al. |
| 6,622,050 B2 | 9/2003 | Thompson |
| 6,650,939 B2 | 11/2003 | Taepke, II et al. |
| 6,664,893 B1 | 12/2003 | Eveland et al. |
| 6,665,385 B2 | 12/2003 | Rogers et al. |
| 6,665,565 B1 | 12/2003 | Stomberg et al. |
| 6,675,045 B2 | 1/2004 | Mass et al. |
| 6,694,177 B2 | 2/2004 | Eggers et al. |
| 6,701,183 B2 | 3/2004 | Baker et al. |
| 6,708,065 B2 | 3/2004 | Von Arx et al. |
| 6,712,762 B1 | 3/2004 | Lichter et al. |
| 6,720,887 B1 | 4/2004 | Zunti |
| D490,525 S | 5/2004 | Stein et al. |
| 6,731,311 B2 | 5/2004 | Bufe et al. |
| 6,735,479 B2 | 5/2004 | Fabain et al. |
| 6,735,551 B2 | 5/2004 | Voegeli et al. |
| 6,749,566 B2 | 6/2004 | Russ |
| 6,758,812 B2 | 7/2004 | Lang |
| 6,763,269 B2 | 7/2004 | Cox |
| 6,766,201 B2 | 7/2004 | Von Arx et al. |
| 6,773,396 B2 | 8/2004 | Flach et al. |
| 6,783,492 B2 | 8/2004 | Dominguez et al. |
| 6,785,573 B2 | 8/2004 | Kovtun et al. |
| 6,792,321 B2 | 9/2004 | Sepe, Jr. |
| 6,801,137 B2 | 10/2004 | Eggers |
| 6,801,802 B2 | 10/2004 | Sitzman et al. |
| 6,804,557 B1 | 10/2004 | Kroll |
| 6,804,558 B2 | 10/2004 | Haller et al. |
| 6,804,559 B1 | 10/2004 | Kraus et al. |
| 6,809,701 B2 | 10/2004 | Amundson et al. |
| 6,820,057 B1 | 11/2004 | Loch et al. |
| 6,840,904 B2 | 1/2005 | Goldberg |
| 6,850,252 B1 | 2/2005 | Hoffberg |
| 6,878,112 B2 | 4/2005 | Linberg et al. |
| 6,885,288 B2 | 4/2005 | Pincus |
| 6,889,086 B2 | 5/2005 | Mass et al. |
| 6,893,395 B1 | 5/2005 | Kraus et al. |
| 6,903,657 B2 | 6/2005 | Kwoen |
| 6,915,265 B1 | 7/2005 | Johnson |
| 6,936,007 B2 | 8/2005 | Quy |
| 6,940,403 B2 | 9/2005 | Kail, IV |
| 6,941,168 B2 | 9/2005 | Girouard |
| 6,954,673 B2 | 10/2005 | Von Arx et al. |
| 6,957,102 B2 | 10/2005 | Silver et al. |
| 6,957,107 B2 | 10/2005 | Rogers et al. |
| 6,958,705 B2 | 10/2005 | Lebel |
| 6,961,621 B2 | 11/2005 | Krishnan et al. |
| 6,963,907 B1 | 11/2005 | McBride et al. |
| 6,970,737 B1 | 11/2005 | Brodnick et al. |
| 6,976,958 B2 | 12/2005 | Quy |
| 6,978,169 B1 | 12/2005 | Guerra |
| 6,978,182 B2 | 12/2005 | Mazar et al. |
| 6,980,112 B2 | 12/2005 | Nee |
| 6,985,771 B2 | 1/2006 | Fischell et al. |
| 6,988,989 B2 | 1/2006 | Weiner et al. |
| 6,993,393 B2 | 1/2006 | Von Arx et al. |
| 7,002,468 B2 | 2/2006 | Eveland et al. |
| 7,009,511 B2 | 3/2006 | Mazar et al. |
| 7,016,739 B2 | 3/2006 | Bange et al. |
| 7,043,305 B2 | 5/2006 | KenKnight et al. |
| 7,058,453 B2 | 6/2006 | Nelson et al. |
| 7,060,030 B2 | 6/2006 | Von Arx et al. |
| 7,065,409 B2 | 6/2006 | Mazar |
| 7,066,883 B2 | 6/2006 | Schmidt et al. |
| 7,070,562 B2 | 7/2006 | Bardy et al. |
| 7,072,718 B2 | 7/2006 | Von Arx et al. |
| 7,079,035 B2 | 7/2006 | Bock et al. |
| 7,096,067 B2 | 8/2006 | Linberg |
| 7,096,068 B2 | 8/2006 | Mass et al. |
| 7,099,715 B2 | 8/2006 | Korzinov et al. |
| 7,104,955 B2 | 9/2006 | Bardy et al. |
| 7,117,031 B2 | 10/2006 | Lohman et al. |
| 7,120,488 B2 | 10/2006 | Nova et al. |
| 7,123,950 B2 | 10/2006 | Mannheimer |
| 7,130,396 B2 | 10/2006 | Rogers et al. |
| 7,134,996 B2 | 11/2006 | Bardy et al. |
| 7,149,570 B2 | 12/2006 | Ellscheid et al. |
| 7,149,773 B2 | 12/2006 | Haller et al. |
| 7,151,435 B2 | 12/2006 | Brackett et al. |

| | | | | | | |
|---|---|---|---|---|---|---|
| 7,155,290 B2 | 12/2006 | Von Arx et al. | | 2005/0245995 A1 | 11/2005 | Diebold |
| 7,156,808 B2 | 1/2007 | Quy | | 2005/0251227 A1 | 11/2005 | Khoo et al. |
| 7,156,809 B2 | 1/2007 | Quy | | 2005/0282494 A1 | 12/2005 | Kossi |
| 7,181,017 B1 | 2/2007 | Nagel | | 2005/0288808 A1 | 12/2005 | Lopez et al. |
| 7,181,505 B2 | 2/2007 | Haller et al. | | 2006/0020314 A1 | 1/2006 | Bodner |
| 7,194,300 B2 | 3/2007 | Korzinov | | 2006/0020960 A1 | 1/2006 | Relan |
| 7,203,545 B2 | 4/2007 | Schmitt et al. | | 2006/0030810 A1 | 2/2006 | Mandrusov et al. |
| 7,212,849 B2 | 5/2007 | Zhang et al. | | 2006/0047318 A1 | 3/2006 | Pastore et al. |
| 7,212,850 B2 | 5/2007 | Prystowsky | | 2006/0052084 A1 | 3/2006 | Diebold et al. |
| 7,218,969 B2 | 5/2007 | Vallapureddy | | 2006/0064133 A1 | 3/2006 | Von Arx et al. |
| 7,240,833 B2 | 7/2007 | Zarembo | | 2006/0064142 A1 | 3/2006 | Chavan et al. |
| 7,257,447 B2 | 8/2007 | Cates et al. | | 2006/0064143 A1 | 3/2006 | Von Arx et al. |
| 7,270,633 B1 | 9/2007 | Goscha | | 2006/0089856 A1 | 4/2006 | Kadhiresan et al. |
| 7,273,454 B2 | 9/2007 | Raymond et al. | | 2006/0106433 A1 | 5/2006 | Mazar et al. |
| 7,283,864 B2 | 10/2007 | Thomas et al. | | 2006/0111759 A1 | 5/2006 | Hoyme et al. |
| 7,286,872 B2 | 10/2007 | Kramer et al. | | 2006/0116744 A1 | 6/2006 | Von Arx et al. |
| 7,289,761 B2 | 10/2007 | Mazar | | 2006/0122667 A1 | 6/2006 | Chavan et al. |
| 7,292,139 B2 | 11/2007 | Mazar et al. | | 2006/0133362 A1 | 6/2006 | Stein et al. |
| 7,313,441 B2 | 12/2007 | Mass et al. | | 2006/0139229 A1 | 6/2006 | Theobold et al. |
| 7,316,648 B2 | 1/2008 | Kelly et al. | | 2006/0142820 A1 | 6/2006 | Von Arx et al. |
| 7,319,903 B2 | 1/2008 | Bange et al. | | 2006/0142821 A1 | 6/2006 | Bange et al. |
| 7,324,850 B2 | 1/2008 | Persen et al. | | 2006/0154642 A1 | 7/2006 | Sannell, Jr. |
| 7,353,063 B2 | 4/2008 | Simms, Jr. | | 2006/0159074 A1 | 7/2006 | Diebold et al. |
| 7,359,753 B2 | 4/2008 | Bange et al. | | 2006/0161213 A1 | 7/2006 | Patel |
| 7,363,080 B2 | 4/2008 | Stubbs et al. | | 2006/0161223 A1 | 7/2006 | Vallapureddy et al. |
| 7,373,200 B2 | 5/2008 | Stubbs et al. | | 2006/0173985 A1 | 8/2006 | Moore |
| 7,378,955 B2 | 5/2008 | Mazar et al. | | 2006/0194615 A1 | 8/2006 | Vallapureddy et al. |
| 7,383,087 B2 | 6/2008 | Hoyme et al. | | 2006/0195162 A1 | 8/2006 | Arx et al. |
| 7,383,088 B2 | 6/2008 | Spinelli et al. | | 2006/0195163 A1 | 8/2006 | KenKnight et al. |
| 7,389,146 B2 | 6/2008 | Hanson et al. | | 2006/0200007 A1 | 9/2006 | Brockway et al. |
| 7,392,086 B2 | 6/2008 | Sathaye | | 2006/0206246 A1 | 9/2006 | Walker |
| 7,392,092 B2 | 6/2008 | Li et al. | | 2006/0218054 A1 | 9/2006 | Postelnik et al. |
| 7,395,117 B2 | 7/2008 | Mazar et al. | | 2006/0241712 A1 | 10/2006 | Cates et al. |
| 7,536,557 B2 | 5/2009 | Murakami et al. | | 2006/0253158 A1 | 11/2006 | Stubbs et al. |
| 7,751,801 B2 | 7/2010 | Torvinen | | 2006/0253163 A1 | 11/2006 | Stubbs et al. |
| 7,752,059 B2 | 7/2010 | Sweeney | | 2006/0253300 A1 | 11/2006 | Somberg et al. |
| 7,830,381 B2 | 11/2010 | Lundstrom et al. | | 2006/0253301 A1 | 11/2006 | Simms et al. |
| 7,978,062 B2 * | 7/2011 | Lalonde et al. ......... 340/539.11 | | 2006/0253894 A1 | 11/2006 | Bookman |
| 2001/0027331 A1 | 10/2001 | Thompson | | 2006/0265740 A1 | 11/2006 | Clark |
| 2002/0010679 A1 | 1/2002 | Felsher | | 2007/0018810 A1 | 1/2007 | Smythe et al. |
| 2002/0052539 A1 | 5/2002 | Haller | | 2007/0027723 A1 | 2/2007 | Bardy |
| 2002/0055917 A1 | 5/2002 | Muraca | | 2007/0036771 A1 | 2/2007 | Wagner et al. |
| 2002/0082480 A1 | 6/2002 | Riff | | 2007/0049983 A1 | 3/2007 | Freeberg |
| 2002/0095196 A1 | 7/2002 | Linberg | | 2007/0049992 A1 | 3/2007 | Freeberg |
| 2003/0025602 A1 | 2/2003 | Medema et al. | | 2007/0053516 A1 | 3/2007 | Katoozi et al. |
| 2003/0227414 A1 | 12/2003 | Saliga | | 2007/0061266 A1 | 3/2007 | Moore |
| 2004/0006265 A1 | 1/2004 | Alhussiny | | 2007/0078491 A1 | 4/2007 | Siejko et al. |
| 2004/0048601 A1 | 3/2004 | Lee et al. | | 2007/0083246 A1 | 4/2007 | Mazar et al. |
| 2004/0117308 A1 | 6/2004 | Bouknight | | 2007/0100384 A1 | 5/2007 | Fischell et al. |
| 2004/0122488 A1 | 6/2004 | Mazar et al. | | 2007/0100396 A1 | 5/2007 | Freeberg |
| 2004/0128161 A1 | 7/2004 | Mazar et al. | | 2007/0100397 A1 | 5/2007 | Seeberger et al. |
| 2004/0170154 A1 | 9/2004 | Carter et al. | | 2007/0106129 A1 | 5/2007 | Srivathsa et al. |
| 2004/0176811 A1 | 9/2004 | Von Arx et al. | | 2007/0106536 A1 | 5/2007 | Moore |
| 2004/0230246 A1 | 11/2004 | Stein et al. | | 2007/0106537 A1 | 5/2007 | Moore |
| 2004/0230247 A1 | 11/2004 | Stein et al. | | 2007/0106750 A1 | 5/2007 | Moore |
| 2004/0233930 A1 | 11/2004 | Colby, Jr. | | 2007/0106751 A1 | 5/2007 | Moore |
| 2004/0260189 A1 | 12/2004 | Eggers et al. | | 2007/0106752 A1 | 5/2007 | Moore |
| 2005/0021370 A1 | 1/2005 | Riff | | 2007/0106753 A1 | 5/2007 | Moore |
| 2005/0027329 A1 | 2/2005 | Holmquist et al. | | 2007/0106754 A1 | 5/2007 | Moore |
| 2005/0032511 A1 | 2/2005 | Malone et al. | | 2007/0116036 A1 | 5/2007 | Moore |
| 2005/0033124 A1 | 2/2005 | Kelly et al. | | 2007/0116037 A1 | 5/2007 | Moore |
| 2005/0071199 A1 | 3/2005 | Riff | | 2007/0118188 A1 | 5/2007 | Von Arx et al. |
| 2005/0091338 A1 | 4/2005 | De la Huerga | | 2007/0123943 A1 | 5/2007 | Patangay et al. |
| 2005/0113900 A1 | 5/2005 | Shiroff et al. | | 2007/0123946 A1 | 5/2007 | Masoud |
| 2005/0114711 A1 | 5/2005 | Hesselink | | 2007/0129642 A1 | 6/2007 | Korzinov |
| 2005/0120082 A1 | 6/2005 | Hesselink | | 2007/0130657 A1 | 6/2007 | Rogers et al. |
| 2005/0125258 A1 | 6/2005 | Yellin | | 2007/0135855 A1 | 6/2007 | Foshee et al. |
| 2005/0131479 A1 | 6/2005 | Axelrod et al. | | 2007/0135865 A1 | 6/2007 | Schmitt et al. |
| 2005/0144186 A1 | 6/2005 | Hesselink | | 2007/0136098 A1 | 6/2007 | Smythe et al. |
| 2005/0144195 A1 | 6/2005 | Hesselink | | 2007/0138253 A1 | 6/2007 | Libin |
| 2005/0144200 A1 | 6/2005 | Hesselink | | 2007/0142727 A1 | 6/2007 | Zhang et al. |
| 2005/0149481 A1 | 7/2005 | Hesselink | | 2007/0150010 A1 | 6/2007 | Stubbs et al. |
| 2005/0159105 A1 | 7/2005 | Mass et al. | | 2007/0150028 A1 | 6/2007 | Parkinson et al. |
| 2005/0160147 A1 | 7/2005 | Denney et al. | | 2007/0156054 A1 | 7/2007 | Korzinov et al. |
| 2005/0192649 A1 | 9/2005 | Shehadeh et al. | | 2007/0157298 A1 | 7/2007 | Dingwall et al. |
| 2005/0192836 A1 | 9/2005 | Rossinni et al. | | 2007/0168222 A1 | 7/2007 | Hoyme et al. |
| 2005/0192837 A1 | 9/2005 | Fears et al. | | 2007/0168461 A1 | 7/2007 | Moore |
| 2005/0192838 A1 | 9/2005 | Jones et al. | | 2007/0175827 A1 | 8/2007 | Wariar |
| 2005/0241026 A1 | 10/2005 | Esler et al. | | 2007/0179349 A1 | 8/2007 | Hoyme et al. |

| | | |
|---|---|---|
| 2007/0180047 A1 | 8/2007 | Dong et al. |
| 2007/0185547 A1 | 8/2007 | Hoyme et al. |
| 2007/0185550 A1 | 8/2007 | Vallapureddy et al. |
| 2007/0191723 A1 | 8/2007 | Prystowsky et al. |
| 2007/0192140 A1 | 8/2007 | Gropper |
| 2007/0195163 A1 | 8/2007 | Chestak et al. |
| 2007/0203754 A1 | 8/2007 | Harrington |
| 2007/0206615 A1 | 9/2007 | Plamondon et al. |
| 2007/0210923 A1 | 9/2007 | Butler |
| 2007/0226013 A1 | 9/2007 | Elletson et al. |
| 2007/0260293 A1 | 11/2007 | Carpenter et al. |
| 2007/0263873 A1 | 11/2007 | Qi |
| 2007/0265533 A1 | 11/2007 | Tran |
| 2007/0273504 A1 | 11/2007 | Tran |
| 2007/0276270 A1 | 11/2007 | Tran |
| 2007/0282634 A1 | 12/2007 | Johnson et al. |
| 2007/0288067 A1 | 12/2007 | Eveland |
| 2007/0288069 A1 | 12/2007 | Goscha et al. |
| 2007/0293776 A1 | 12/2007 | Korzinov et al. |
| 2007/0299317 A1 | 12/2007 | Hoyme et al. |
| 2008/0001735 A1 | 1/2008 | Tran |
| 2008/0004904 A1 | 1/2008 | Tran |
| 2008/0015655 A1 | 1/2008 | Bange et al. |
| 2008/0015656 A1 | 1/2008 | Bange et al. |
| 2008/0021521 A1 | 1/2008 | Shah et al. |
| 2008/0021523 A1 | 1/2008 | Cates et al. |
| 2008/0021524 A1 | 1/2008 | Goscha et al. |
| 2008/0021730 A1 | 1/2008 | Holla |
| 2008/0021741 A1 | 1/2008 | Holla |
| 2008/0021834 A1 | 1/2008 | Holla |
| 2008/0024294 A1 | 1/2008 | Mazar |
| 2008/0027499 A1 | 1/2008 | Srivathsa et al. |
| 2008/0040151 A1 | 2/2008 | Moore |
| 2008/0055070 A1 | 3/2008 | Bange et al. |
| 2008/0058651 A1 | 3/2008 | Shen et al. |
| 2008/0058881 A1 | 3/2008 | Wagner et al. |
| 2008/0061961 A1 | 3/2008 | John |
| 2008/0071183 A1 | 3/2008 | Thomas et al. |
| 2008/0071314 A1 | 3/2008 | John |
| 2008/0086185 A1 | 4/2008 | Amurthur et al. |
| 2008/0103542 A1 | 5/2008 | Hoyme et al. |
| 2008/0109051 A1 | 5/2008 | Splinter et al. |
| 2008/0114412 A1 | 5/2008 | Bange et al. |
| 2008/0140163 A1 | 6/2008 | Keacher |
| 2008/0150937 A1 | 6/2008 | Lundstrom et al. |
| 2008/0154099 A1 | 6/2008 | Asper |
| 2008/0157928 A1 | 7/2008 | Butler |
| 2008/0164975 A1 | 7/2008 | Butler |
| 2008/0164977 A1 | 7/2008 | Butler |
| 2008/0177194 A1 | 7/2008 | Zhang et al. |
| 2008/0180249 A1 | 7/2008 | Butler |
| 2008/0186137 A1 | 8/2008 | Butler |
| 2008/0186138 A1 | 8/2008 | Butler |
| 2008/0186139 A1 | 8/2008 | Butler |
| 2008/0186180 A1 | 8/2008 | Butler |
| 2008/0211630 A1 | 9/2008 | Butler |
| 2008/0222711 A1 | 9/2008 | Michaelis |
| 2008/0252459 A1 | 10/2008 | Butler |
| 2008/0294019 A1 | 11/2008 | Tran |
| 2008/0306872 A1 | 12/2008 | Felsher |
| 2009/0019552 A1 | 1/2009 | McLaughlin |
| 2009/0024416 A1 | 1/2009 | McLaughlin |
| 2009/0058636 A1 | 3/2009 | Gaskill |
| 2009/0062887 A1 | 3/2009 | Mass |
| 2009/0063187 A1 | 3/2009 | Johnson |
| 2009/0063193 A1 | 3/2009 | Barton |
| 2009/0146822 A1 | 6/2009 | Soliman |
| 2009/0222898 A1 | 9/2009 | Veidung |
| 2009/0240526 A1 | 9/2009 | Vesto et al. |
| 2009/0320029 A1 | 12/2009 | Kottomtharayil |
| 2010/0144316 A1 | 6/2010 | Piercy et al. |
| 2010/0225468 A1 | 9/2010 | Sievert et al. |
| 2010/0228977 A1 | 9/2010 | Sievert et al. |

FOREIGN PATENT DOCUMENTS

| | | |
|---|---|---|
| JP | 2003047599 | 2/2003 |
| JP | 2005080175 | 3/2005 |
| JP | 2007200276 | 8/2007 |
| WO | WO9736443 | 10/1997 |
| WO | WO03077994 | 9/2003 |
| WO | WO03100647 | 12/2003 |
| WO | WO2004109992 | 12/2004 |
| WO | WO2006010166 | 1/2006 |
| WO | WO2009032134 | 3/2009 |

OTHER PUBLICATIONS

International Search Report and Written Opinion dated Apr. 9, 2009 from PCT Application No. PCT/US2008/010162, 24 pages.
Invitation to Pay Additional Fees dated Jul. 12, 2010 from PCT Application No. PCT/US2010/026076, 6 pages.
International Search Report and Written Opinion dated Oct. 11, 2010 from PCT Application No. PCT/US2010/026076, 17 pages.
File History for U.S. Appl. No. 12/151,869.
File History for EP Application No. 08795636.3 as retrieved from the European Patent Office Electronic File System on Jul. 12, 2011, 59 pages.
Savci et al., "MICS Transceivers: Regulatory Standards and Applications", IEEE Proceedings, Apr. 8, 2005. pp. 179-182.
Valdastri et al., "An implantable ZigBee ready telemetric platform for in vivo monitoring of physiological parameters," Sensors and Actuators A, vol. 142, 2008, pp. 369-378.
Margolis et al., Latitude Active Monitoring alerts physician of silent AF episode, Latitude Patient Management Case Study, Boston Scientific Corporation, 2006, 2 pages.
Biotronic Technical Manual for Philos DR-T, DDDR Dual Chamber Pulse Generator with Home Monitor, 2004, 32 pages.
Medtronic Analyzer Reference Guide for Medtronic Carelink Analyzer, Model 2290 Analyzer for Medtronic and Vitatron Devices, 2008, 106 pages.
Medtronic Programmer Reference Guide for Medtronic Carelink Programmer, Model 2090 Programmer for Medtronic and Vitatron Devices, 2008, 112 pages.
File history for U.S. Appl. No. 12/228,915.
File history for U.S. Appl. No. 12/151,780.
File history for U.S. Appl. No. 12/151,796.
File history for U.S. Appl. No. 12/151,910.
U.S. Appl. No. 12/151,796.
U.S. Appl. No. 12/694,826.
JP Office Action with translation dated Mar. 28, 2012 from JP Application No. 2010-522944, 4 pages.
U.S. Appl. No. 12/228,915.
for U.S. Appl. No. 12/151,910.
U.S. Appl. No. 12/151,780.
European Application No. 08795636.3.
U.S. Appl. No. 12/694,817.
JP Office Action Response dated Jun. 20, 2012 from JP Application No. 2010-522944, 24 pages.
U.S. Appl. No. 12/151,869.
Office Action Response dated Aug. 24, 2012 for U.S. Appl. No. 12/694,817, 13 pages.
Office Action Response dated Sep. 4, 2012 for U.S. Appl. No. 12/151,910, 13 pages.

* cited by examiner

| Patient/Device | Last Remote Interrogaton | My Alerts | Device Status | Physician(s) | Next Remote Follow-up | Disposition |
|---|---|---|---|---|---|---|
| Theo H210/600112 | 06 Apr 2005 | ◆ | ◇ | Pat M.D. Dana M.D. | 25 Oct 2005 | Unscheduled Review Started |
| Bernie H170/600111 | 04 Apr 2005 | | △ | Pat M.D. Dana M.D. | 10 Dec 2005 | Ready for Review |
| Sylvia 1860/327149 | 10 Mar 2005 | | | Pat M.D. Dana M.D. | 30 Oct 2005 | New Patient New PG |
| Paul H210/600332 | 02 Apr 2005 New Data | | | Pat M.D. Dana M.D. | 12 Sep 2005 | Patient-Initiated Ready For Review |
| Steven H210/602353 | 16 Feb 2005 | | | Pat M.D. Dana M.D. | 19 Aug 2005 | Data Not Available |

Fig. 12A

| | LATITUDE Patient Management | Report Created 08 Aug 2003 |
|---|---|---|
| GUIDANT | Quick Notes Report<br>Date of Birth  19 Apr 1961<br>Device  RENEWAL 3 RF H210/999999<br>A-Tachy Mode  Monitor Only<br>A-Tachy Mode  Monitor + Therapy | Last Remote Interrogation<br>04 Jul 2003<br>Last In-Office Lead Test<br>15 May 2003<br>Implant Date<br>10 Jun 2000 |

My Alerts
- 17 Jun 2003 - Alert Description
- 30 Jun 2003 - Alert Description
  See last page for full list of alerts

Events Since Last Remote Follow-up (04 Jul 2003)
- 16 Jul 2003 07:13 VT at 160 bpm, 2 therapies delivered, accel to VF at 190,10 J conversion to 91 bpm
- 16 Jul 2003 05:22 VT at 180 bpm, 10 J conversion to 88 bpm
  See last page for full list of Events Since Last Remote Followw-up.

Battery  OK

| Monitoring Voltage | 3.25V | Elective Replacement |
| Charge Time | 10 sec | Indicator (ERI) |
| Last Reform | 5 Mar 2002 | End of Life (EOL) —— Beginning of Life (BOL) |

| Leads Data | Implant<br>10 Jun 2000 | Last In-Office<br>Lead Test<br>15 May 2003 | Last Remote<br>Interrogation<br>04 Jul 2003 |
|---|---|---|---|
| ◇ Atrial | | | |
| Intrinsic Amplitude | 3.1 mV | 2.6 mV (23 Feb 2003) | 3.1 mV |
| Pace Impedance | 610 Ω | 190 Ω | 610 Ω |
| Pace Threshold | 0.4 V @ 0.5 ms | N/R | |
| Right Ventricular | | | |
| Intrinsic Amplitude | 11.1 mV | 11.1 mV | 11.1 mV |
| Pace Impedance | 900 Ω | 900 Ω (23 Feb 2003) | 900 Ω |
| Pace Threshold | 0.4 V @ 0.5 ms | N/R | |
| Left Ventricular | | | |
| Intrinsic Amplitude | 11.1 mV | 11.1 mV | 11.1 mV |
| Pace Impedance | 900 Ω | 900 Ω | 900 Ω |
| Pace Threshold | 0.4 V @ 0.5 ms | 0.5 V @ 0.5 ms (23 Feb 2003) | |
| Shock | | | |
| Shock Impedance | 58 Ω | 65 Ω (23 Feb 2003) | 66 Ω |

Settings

| Ventricular Tachy Settings | | Atrial Tachy Settings | |
|---|---|---|---|
| VF Zone | 10 J, 31 J, 31 J x 4 | ATR Mode Switch Mode | VDI |
| VF Zone | ATP x 2, 31 J, 31 J | ATR Mode Switch Rate | 170 bpm |
| vt-1 Zone | | AFib  225 bpm | 10 J, 31 J, 31 J x 4 |
| Brady and CRT Settings | | SVT  170 bpm | ATP x 2, 31 J, 31 J |
| Brady Mode | DDDR | Pacing Output | |
| Lower Rate Limit | 60 ppm | Atrial | 3.5 V @ 0.5 ms |
| Maximum Tracking Rate | 120 ppm | Right Ventricular | 1.5 V @ 0.5 ms |
| Maximum Sensor Rate | 120 ppm | Left Ventricular | 2.5 V @ 0.5 ms |
| Paced AV Delay | 100-150 ms | Sensitivity | |
| Sensed AV Offset | 20 ms | Atrial | Nominal |
| AV Search Hysteresis | | Right Ventricular | Nominal |
| Search Interval | 10 cycles | Left Ventricular | Nominal |
| AV Increase | 10 % | | |
| A-Refractory (PVARP) | 240-250 ms | | |
| RV-Refractory (RVRP) | 240-250 ms | | |
| LV-Refractory (LVRP) | 300 ms | | |
| LV Protection Period | 300 ms | | |
| Ventricular Pacing Chamber | BiV | | |
| LV Offset | 20 ms | | |

Fig. 12C

MEDICAL DATA TRANSPORT OVER WIRELESS LIFE CRITICAL NETWORK

RELATED APPLICATIONS

This application is a continuation of U.S. Ser. No. 12/151,869 filed on May 9, 2008, now U.S. Pat. No. 7,978,062 issued on Jul. 12, 2011 and claims the benefit of Provisional Patent Application Ser. Nos. 60/967,060, 60/967,061, 60/967,062, and 60/967,063 filed on Aug. 31, 2007, which are incorporated herein by reference in their entireties.

FIELD OF THE INVENTION

The present invention relates generally to systems, devices, and methods for transporting medical information over a wireless network.

BACKGROUND

Implantable pulse generators (IPGs) are medical devices commonly used to treat irregular heartbeats, known as arrhythmias. Cardiac pacemakers, for example, are designed to manage bradycardia, an abnormally slow or irregular heartbeat. Left untreated, bradycardia can cause symptoms such as fatigue, dizziness, and fainting. Cardiac resynchronizers are a particular class of pacemaker that provide cardiac resynchronization therapy, such a bi-ventricular pacing, for patients suffering from heart failure. Implantable cardioverter defibrillators (ICDs), by way of further example, are designed to treat tachycardia, heart rhythms that are abnormally fast and life threatening.

Some forms of tachycardia can result in sudden cardiac death, if left untreated. Pacemakers and ICDs are increasingly being equipped with an on-board, volatile memory in which telemetered signals can be stored for later retrieval and analysis. The telemetered signals provide various types of patient device information, such as atrial electrical activity, ventricular electrical activity, time of day, activity level, cardiac output, oxygen level, cardiovascular pressure measures, pulmonary measures, and any interventions made on a per heartbeat or binned average basis. In addition, a growing class of cardiac medical devices, including implantable heart failure monitors, implantable event monitors, cardiovascular monitors, and therapy devices, are being used to provide similar stored device information. These devices are typically designed to store approximately thirty minutes of heartbeat data. Telemetered signals are also stored in a broader class of monitors and therapeutic devices for other areas of medicine, including metabolism, endocrinology, hematology, neurology, muscular, gastrointestinal, genital-urology, ocular, auditory, and the like.

Information stored in an implantable medical device is typically retrieved using a proprietary interrogator or programmer, often during a clinic visit or following a device event. The volume of data retrieved from a single device interrogation procedure can be large and proper interpretation and analysis can require significant physician time and detailed subspecialty knowledge, particularly by cardiologists and cardiac electrophysiologists. Present approaches to data interpretation and understanding, and practical limitations on time and physician availability, make such analyses impracticable.

Conventional systems for collecting and analyzing pacemaker and ICD telemetered signals in a clinical or office setting can be used to retrieve data, such as patient electrocardiogram and any measured physiological conditions, collected by the IPG for recordation, display and printing. The retrieved data may displayed in chronological order and analyzed by a physician. Conventional systems often lack remote communications facilities and must be operated with the patient present. These systems present a limited analysis of the collected data based on a single device interrogation and lack the capability to recognize trends in the data spanning multiple episodes over time or relative to a disease specific peer group.

SUMMARY OF THE INVENTION

The present invention is directed to systems, devices, and methods for transporting medical information over a wireless network. A portable patient communicator (PPC) is configured for communicating with a patient implantable medical device (PIMD) and facilitating communications with a remote server via a wireless network. The wireless network typically supports a number of disparate data transport mechanisms having differing characteristics. A data transport mechanism is selected among the various available data transport mechanism based on one or more factors, such as type of data, criticality of data and/or patient condition, occurrence of a particular event or events, environmental factors, network factors, and needs of the patient, physician or technician, among others.

According to various embodiments, a portable patient communicator PPC includes a housing configured for portability by an ambulatory patient. A processor is coupled to memory, and the processor and the memory are provided in the housing. The memory stores wireless radio firmware and medical firmware. The medical firmware is executable by the processor to facilitate interaction between the PPC and the PIMD in accordance with predetermined medical device guidelines. A first radio is provided in the housing and configured to effect communications with the PIMD in accordance with program instructions of the medical firmware executable by the processor. A second radio is provided in the housing and configured to effect communications via the wireless network in accordance with program instructions of the wireless radio firmware executable by the processor. A power source is provided in the housing and configured to supply power for components of the PPC.

The processor is configured to receive data from the PIMD via the first radio to which a priority level is assigned. The processor is configured to execute program instructions for selecting a data transport mechanism among a plurality of disparate data transport mechanisms based at least in part on the priority level and transmit at least some of the PIMD data to the wireless network using the selected transport mechanism via the second radio.

In accordance with various embodiments, methods of the present invention may be implemented to effect communications between a portable patient communicator and a patient implantable medical device and facilitate communications between the PPC and a remote server via a wireless network. A PPC is provided that includes a housing configured for portability by an ambulatory patient. The housing supports a processor coupled to memory for storing medical firmware and wireless radio firmware, first and second radios, a processor, and a power source. Methods of the present invention involve effecting communications between the PIMD and the first radio of the PPC in accordance with program instructions of the medical firmware, and effecting communications between the second radio of the PPC and the wireless network in accordance with program instructions of the wireless radio firmware. Data from the PIMD is received via the first radio to which a priority level is assigned. A data transport mechanism is selected among a plurality of disparate data transport mechanisms based at least in part on the priority level. At least some of the PIMD data is transmitted to the wireless network using the selected transport mechanism via the second radio.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 12A-12C show various data and reports that may produced using medical information transported over a life critical network in accordance with embodiments of the present invention;

Figure 1A:
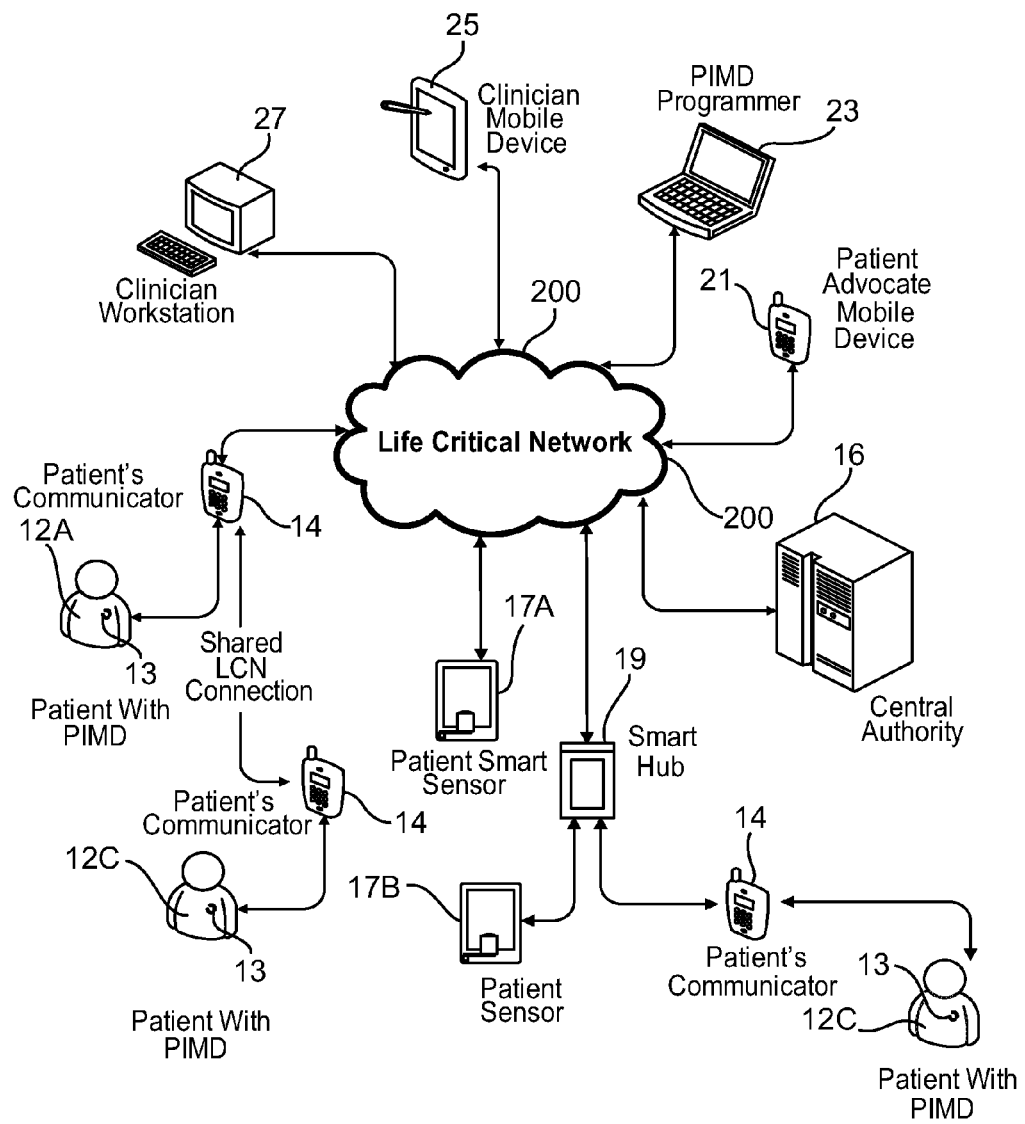
FIG. 1A is a system diagram of a life critical network implementation in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described herein. For example, a device or system may be implemented to include one or more of the advantageous features and/or processes described below. It is intended that such a device or system need not include all of the features described herein, but may be implemented to include selected features that provide for useful structures, systems, and/or functionality.

A life critical network of the present invention is preferably configured as a robust network supported by existing mobile and data networks, and exhibiting heightened communication attributes such as guaranteed delivery, high quality of service (QoS), and tight security. A life critical network implemented in accordance with the present invention provides for the acquisition of physiologic and contextual data acquired for any number of patients that are each carrying a portable communications device, referred to herein interchangeably as a portable patient communicator (PPC) or patient communicator (PC).

Acquisition of physiologic data by a remote server of the life critical network for individual patients may advantageously occur on an unscheduled basis, such as in response to predefined events (e.g., tachycardia events) or in response to patient initiated interrogations. In this regard, a life critical network may acquire patient data for any number of patients that carry a PPC on an event-driven basis, in contrast to a time-scheduled basis.

Remote server acquisition of patient physiologic data may occur while the patient is ambulatory, such as during daily routines at the home or office, or when traveling locally, nationally or worldwide. Physiologic data for patients may be acquired by a wide variety of sensors, including external and internal sensors. For example, an implantable medical device, such as a pacemaker or ICD, may acquire physiologic data and transmit such data to the PPC.

Data acquired by the PPC may be transmitted to a remote server of the life critical network in real-time, such as by use of a real-time data streaming protocol. Store-and-forward data transfer protocols may also be employed, such as for less critical data or when a real-time data transfer connection is not available. Incremental data transfers may also be performed to reduce the volume of data transferred from the PPC to the remote server. A life critical network of the present invention provides connectivity between a patient's PPC and remote server that can be dynamically adjusted to meet the needs of the patient, physician, emergency services, and system/technical personnel.

Real-time transfer of patient physiologic data may be triggered by real-time clinical events detected by a sensor or implantable medical device provided with the patient. Data transfers may also be triggered in accordance with query/response protocols. Clinical alerts for high risk patients may be communicated through the life critical network in real-time. Physiologic monitoring for remote triage may be implemented in real-time through the life critical network.

Examples of patient data that may be transferred from the PPC to the remote server include electrograms (EGMs), clinical event data, episode counters, alerts, device or sensor settings, battery status, lead measurements, and patient activity level, among other types of data. Data transferred from the PPC to the remote server may be integrated at a web site supported by the remote server and displayed at a remote location (e.g., physician's office).

Notification of data delivery and/or alerts from the PPC to the patient's physician, an EMT or patient advocate, for example, may be implemented by a telephone call from the life critical networks service, a fax, email or SMS message, among other modes of communication. Other forms of patient/server interaction facilitated by the life critical network include medication management and remote interrogation or programming of the sensor or implantable medical device.

A PPC implemented in accordance with the present invention facilitates acquisition of patient sensor or implantable medical device data by a remote system for ambulatory patients. A PPC of the present invention is preferably configured to communicate wirelessly over existing mobile and data networks, and to effect local wireless communication with one or more internal and/or external physiologic sensors, ambient and/or contextual sensors, implantable medical devices, and/or other external systems or devices.

A PPC of the present invention may be implemented to provide a wide spectrum of capabilities and functionality. For example, the PPC may be configured to provide only a limited number of features, such as in the case of a PPC having a reduced feature set. By way of further example, a PPC may be implemented to provide a variety of features and capabilities that enable a wide range of functionality.

A PPC implemented in accordance with embodiments of the present invention may be dynamically configurable via interaction with a remote server of a patient management system and/or an implantable medical device or system. Dynamically altering the configuration of a PPC serves to enhance cooperative operation between the PPC, implantable medical device/sensor, and networked patient management system, referred to herein as an advance patient management (APM) system or server. Dynamically altering the configuration of a PPC may also serve to conserve power of the implantable medical device or sensor(s) that are communicatively coupled to the PPC.

A life critical network coupling a patient implantable medical device (PIMD) with an APM server via a PPC provides the opportunity for increased interaction between the patient and various network components and services. Mobile cellular connectivity of the portable communication device facilitates a variety of interactions between the patient and the APM system, between the patient and the PIMD-PPC pair, and/or between the patient or PIMD-PPC pair and other services accessible via the mobile cellular network.

Exemplary services that may be provided through use of the PIMD-PPC pair involve medication management for the patient, medication schedule compliance tracking, exercise schedule compliance tracking, and/or periodic physiological test compliance tracking, compliance tracking of prescribed external therapies (e.g., patient use of CPAP or oxygen therapies), prescription refills, and/or information relayed to the patient's physician, patient advocate or APM server if patient activity, exercise or physiological tests indicate a change that needs attention.

The PPC and/or server may generate reminders to the patient to perform some action, such as taking medication, perform a home-based diagnostic test, exercise, or use an external therapy device. The patient reminders may be based on a particular time schedule or may be event-driven based on the physiological condition of the patient. A physician monitoring the patient may prescribe the regimen of exercise (e.g., exercise frequency or duration), and other types of activities, including those listed above, for example, and the patient reminders may be based on patient compliance with the prescribed regimen.

The functionality provided by reminder schedules, medication schedule or activity tracking may provide incentives for a patient to stay communicatively coupled to the network, allowing for a higher level of care.

The ability of the PIMD-PPC pair to provide event-driven updates, real-time waveform viewing and nearly instantaneous command access to the PIMD for modifying device parameters facilitates remote interrogation, testing, and PIMD programming through the life critical network.

Embodiments of the invention contemplate the involvement of application-specific network solutions, as well as exploiting existing and future network technologies. Patients are equipped with a PPC capable of carrying out wireless communications over existing data networks. Device and network attributes can also be modified and/or controlled to provide a "life critical network" by which the communication of vital patient information can approach guaranteed, secure delivery.

It may be unnecessary, impractical or otherwise undesirable to restrict patients to physical areas where equipment is located to facilitate information communication with patient management services. In many cases, the patient's condition or health does not restrict the patient from normal daily activities, or at least from activities that would separate the patient from fixed equipment used to communicate with patient management services. Solutions provided by the invention advance patient mobility by enabling wireless communication of data, commands and/or other information between patient devices and patient management systems. By furnishing the patient with such mobile communication equipment, communication can be effected periodically or semi-continuously, at any needed time or place.

FIG. 1A is a system diagram of a life critical network implementation in accordance with embodiments of the present invention. The network implementation shown in FIG. 1A includes multiple components linked together to provide a specialized network that guarantees secure and timely delivery of data that are transmitted over one or more networks and attempts to meet specific context sensitive criteria on delivery of that data.

The life critical network 200 essentially provides a private network that is configured to operate on top of existing mobile and fixed facility networks. The LCN 200 utilizes a secured architecture providing for authentication and management of those components that are allowed access to the network 200. Such components or nodes include, for example, portable patient communicators 14, patient sensors 17A-17B, PIMD programmer systems 23, clinician mobile devices 25, clinician workstations 27, patient advocate mobile devices 21, and smart hubs 19, among others.

The LCN 200 preferably follows cryptographic best practices with regard to confidentiality, integrity, and availability. Given the computational—versus-power requirements, the LCN system 200 can minimize the number of asymmetric cryptographic operations in favor of a symmetric algorithm based on various factors, including a known shared-secret generated or installed at time of manufacture, and a dynamically shifting key based on a seed fed to a pseudo random number generator (e.g., such as model, serial number, and network time).

The LCN system 200 preferably leverages the physical network as a virtualized transport, essentially treating any underlying protocol as potentially unsecured, and thus not relying on any native security mechanisms inherent in any given protocol with regard to the encryption and integrity of its data. The LCN system 200 preferably supports both stateful and stateless connections in order to facilitate asynchronous communication where network bandwidth does not support real-time communication.

The LCN 200, as shown in the embodiment of FIG. 1A, employs a central authority 16 to manage access to the network infrastructure. This involves cryptographically validating and authenticating content from a potential node prior to allowing access, and performing other control aspects of policing the network infrastructure. The LCN 200 preferably supports the concept of classification of nodes on the network 200 into a specific hierarchy of access abilities. The various entities requesting access to the LCN 200 are granted different access rights based on their classification. For example, a low-urgency sensor device 17A-17B may not be given access to high-speed connectivity if it is classified in a lower urgency or priority tier. A patient implantable medical device programming system 23 may be granted priority access to a higher speed connectivity capability due to its more demanding need for timely interconnection to the infrastructure. This classification and prioritization is preferably dynamically managed via the central authority 16.

One aspect of creating and maintaining an LCN 200 in accordance with the present invention is the ability to dynamically map the available connectivity options between nodes in the network 200. This process is a key capability to providing the optimum resources for the network infrastructure as well as defining various profiles for communication.

The process of mapping the environment at the source end of the network 200 begins by the source agent performing a series of queries and/or connection attempts via various methods to build potential temporal and spatial profiles. In various embodiments, the device performing the mapping may employ multiple forms of both wired and wireless communications. The communication mechanisms may include, but are not limited to, the following: RF Wireless Transceivers (WiFiMax, IEEE 802.11a/b/g/n, etc.); Cellular Network Transceivers (GSM, EDGE, GPRS, CDMA, etc.); Bluetooth (high or low power methods); Zigbee (IEEE 802.15.4); Wired Ethernet (IEEE 802.3); Plain Old Telephone System (POTS)/Public Switched Telephone Network (PSTN); Emergency Systems (e.g., 911, WPS); TDD, SMS, MMS, EMS, and VOIP, among others.

The mapping determines the most efficient and most reliable connection options that are present in the current location of the source device. Because network connections are not always stable, the mapping process attempts to survey all of the currently available connection options. A profile maintains these options and lists various attributes of the connectivity methods found. These attributes could, for example, include the following: signal type; signal strength; provider name; preferred network provider information; encryption options available; and compression options available, among others.

Once the environment has been mapped, the measured results are then prioritized into a list of connection options of the highest bandwidth, with the most robust and secure option first on the list and then descending towards less secure and robust options. Not all options are available or viable in a specific environment. As a result, the list is populated with only those connections that meet the required connectivity requirements.

The mapping agent has the capability for creating and managing multiple profiles per user per device. The ability to create different profiles based on the patient location allows the LCN nodes the ability to have multiple sets of connection options that are dynamically selected based on the location of the patient. The decision to create a new profile can be autonomously decided by the source user device due to the device sensing a new location/environment for a specified timeframe or via direct interaction with the user. Many types of environments may exist for the user—at the users residences (e.g., home, office, hospital, etc), at a mobile location (e.g., transit options including car, rail, planes, marine, etc.).

The LCN system 200 may employ a peer-to-peer or ad hoc network profile, where devices brought within range of one another may elect to leverage a profile of the other device in order to pass information up to the system, in particular sensors may utilize a node hopping approach. The condition where there are no viable connectivity options available is realistic, so in this case the source device preferably has means (electronic or non-electronic) of conveying some aspect of the lack of connectivity to the user directly. This may be via various physical means including but not limited to vibration, lighting an indicator, audio outputs, etc.

The connection between LCN nodes, once established, is used to transfer data securely between a source and a target. In various embodiments, the source end represents a medical device that is used to communicate data and diagnostic information from other medical devices in a patient's environment. These data may originate from medical devices taking the form of implantable medical devices (ICD, CRT-D, pacemakers, etc.), or sensor devices both external to the patient (e.g., a weight scale or a blood pressure monitor) and implantable sensors (e.g., pressure sensors, blood chemistry, temperature, etc).

These data components have varying attributes associated with them, specifically, the basic attributes of size and context. However, there also is a concept of urgency/priority. The source component can provide this urgency/priority as a guide for determining how data is transmitted via the LCN 200. For example, if the data retrieved was of high urgency and criticality, the source component could use a higher performing transmission capability of the LCN 200 to ensure that the urgent content is sent to the target in the most efficient way. This concept would also be used as part of the prioritization as to how the LCN profile would be traversed.

The target component commonly is a computer system that provides the ability to store the retrieved content sent from the source. The use of the LCN 200 enables two-way communication between the source and target nodes. The data content being sent from the target to the source can have many contexts. Specifically, the data could contain configuration information for a node or software updates, as well as any system connectivity updates (e.g., protocol updates, network infrastructure updates, approved provider lists, etc.)

Alternative methods for data transmission over the LCN 200 may involve data parsing based on criticality of data or multicasting data via several channels at once. According to some embodiments, the source nodes in the LCN system 200 may choose to parse data into various categories based on urgency and use different methods based on the categorization. An example of this capability involves a required data upload for a medical device where the raw medical device data is sent via fast communication channels, and statistical information may be sent along a slower, less urgent communication channel. This capability allows the source node the ability to tailor use of the LCN infrastructure 200 due to business needs, while still maintaining the critical aspects of the medical device content.

According to other embodiments, there may be conditions where urgent content needs to be sent to a target and the sending node sends the content across multiple communication methods to assure that the data is received by the target node. This allows the target to receive the data from multiple methods and reconstruct the message if partial messages are received.

Figure 1B:
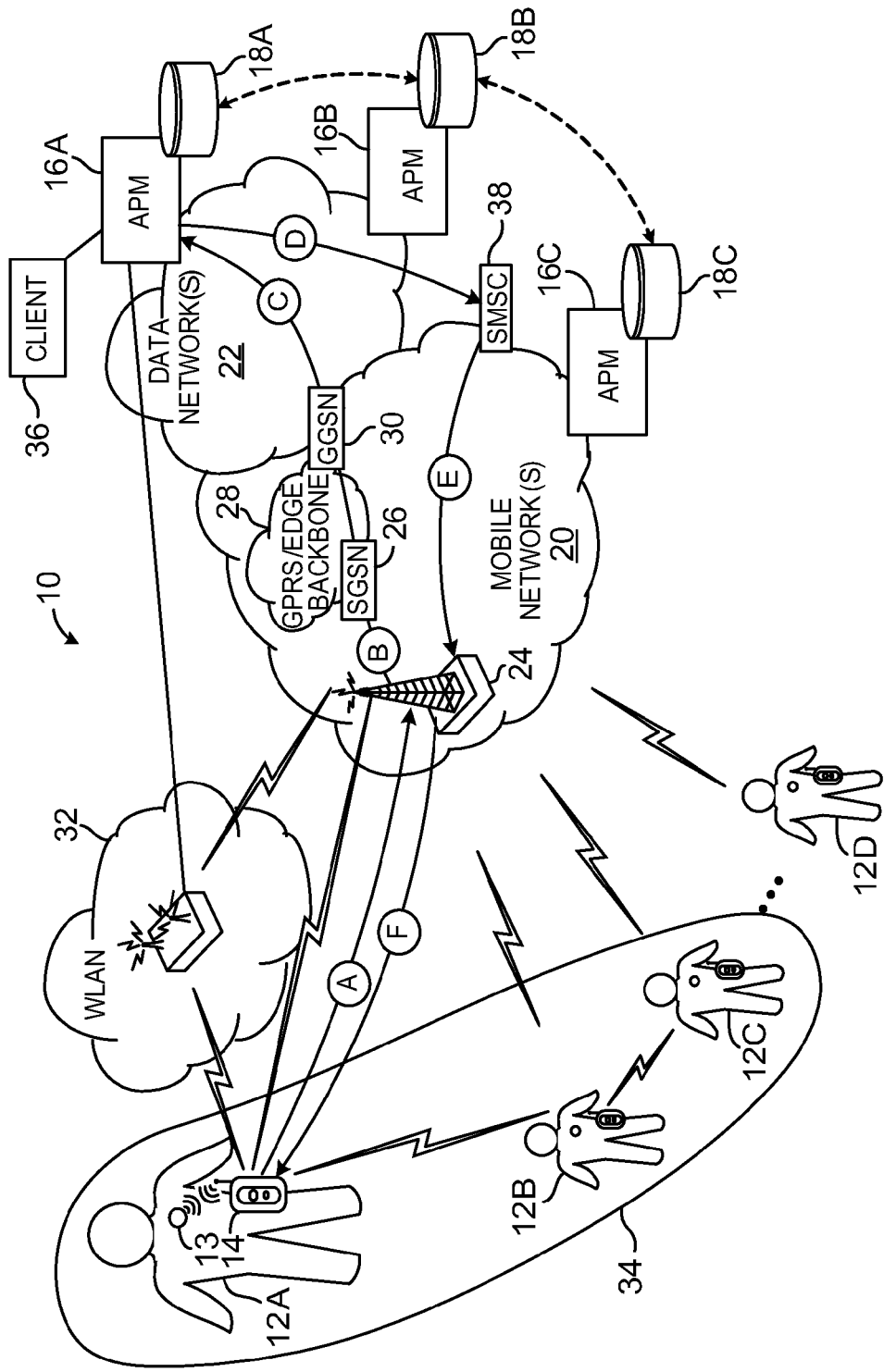
FIG. 1B illustrates an exemplary automated or advanced patient management environment supported within a life critical network in accordance with embodiments of the present invention.

Automated patient management involves numerous activities, including remote patient management and automatic diagnosis of the device and/or patient health. FIG. 1B illustrates an exemplary automated or APM environment 10 supported by the present invention. Each patient 12A, 12B, 12C, 12D involved with the APM environment is associated with one or more data sources or medical devices 13 (hereinafter medical devices) associated with that patient. These medical devices 13 include, for example, medical therapy devices that deliver or provide therapy to the patient 12A, medical sensors that sense physiological data in relation to the patient 12A, and measurement devices that measure environmental parameters occurring independent of the patient 14.

Each patient medical device 13 can generate one or more types of patient data and can incorporate one or more components for delivering therapy, sensing physiological data and measuring environmental parameters. Representative medical devices include patient implantable medical devices (PIMDs) such as pacemakers, implantable cardiac defibrillators, drug pumps, neuro-stimulators and the like. External medical devices may also be paired with the PPC, such as automatic external defibrillators (AEDs). The medical devices may also include implantable or external sensors. Implantable sensors include, for example, heart and respiratory monitors, implantable diagnostic multi-sensor non-therapeutic devices, etc. External sensors may include Holter monitors, weight scales, blood pressure cuffs, temperature sensors (e.g., digital thermometers and cutaneous temperature sensors), ECG and/or heart rate sensor, gas sensors for sensing oxygen and carbon dioxide concentration via a respiratory mask, such as a CPAP mask, drug dispensers or pill counters, etc. Other types of medical, sensing, and measuring devices, both implantable and external (e.g., drug delivery devices), are possible.

Each patient 12A, 12B, 12C, 12D involved with the APM environment is also associated with at least one PPC 14 capable of wirelessly communicating information with an APM system represented by one or more APM servers 16A, 16B, 16C. Each APM server may include a database 18A, 18B, 18C to store information such as patient data, device/sensor configuration and diagnostic data, PIMD and PPC power status and usage data, LCN connection data, and the like. The APM server arrangement may be implemented in a single server/database 16A/18A, or may include multiple servers and databases as depicted in FIG. 1B. Further, the APM server arrangement may include multiple servers and associated databases operating substantially independently. In such a case, information may be exchanged between any of the APM servers through information requests and responses. Alternatively multiple servers and databases may operate as a distributed server/database system to collectively serve as a single APM system.

Each PPC 14 is uniquely assigned to a particular patient 12A, preferably through a process generally referred to herein as "pairing" in accordance with various embodiments. As used herein, pairing generally refers to the unique association created between the patient's PPC 14 and the medical device(s) 13 associated with that patient. When information is to be transmitted between the medical devices 13 and an APM server 16A, the PPC 14 paired with a respective medical device(s) 13 serves to wirelessly communicate the information over one or more networks. In one embodiment, the PPC 14 communicates by way of a mobile network(s) 20, such as a cellular network. A cellular network generally refers to a radio network made up of numerous cells generally defined by a transmitter or "base station." Each base station provides coverage for an area defining its respective cell, and the collective cell structure thus provides radio coverage over a wider area. The mobile network(s) 20 may represent any one or more known or future wireless networking technologies, such as the Global System for Mobile Communications (GSM), Universal Mobile Telecommunications System (UMTS), Personal Communications Service (PCS), Time Division Multiple Access (TDMA), Code Division Multiple Access (CDMA), Wideband CDMA (WCDMA), or other mobile network transmission technologies.

In one embodiment of the invention, the PPC 14 communicates wirelessly via a GSM network. Data may be communicated via a General Packet Radio System (GPRS) mobile communications network, where GPRS refers to a packet-switched service for GSM that mirrors the Internet model and enables seamless transition towards advanced generation networks. GSM/GPRS networks have further evolved to provide increased data transfer rates over the network. For example, one embodiment of the invention exploits the Enhanced Data rates for GSM Evolution (EDGE), which is also known as Enhanced GPRS (EGPRS). EDGE is a digital mobile technology that allows for increased data transmission rates and reliability, and is essentially a "bolt on" enhancement to second generation GSM and GPRS networks. Further enhancements to EDGE networks, such as "EDGE Evolution," provides even further increases in data rates, error correction and signal quality.

Data communicated between the PPC 14 and the mobile network(s) 20 is ultimately communicated with the APM server 16A. As previously indicated, the APM server 16A may or may not be associated with one or more other discrete or distributed server/database systems 16B/18B, 16C/18C, etc. One or more data networks 22 may cooperatively operate with the mobile network(s) 20 to facilitate data transfers to and from the relevant APM server 16A. For example, the illustrated data network 22 may represent the Internet, which interfaces to the illustrated EDGE or other mobile network 20 to serve landline APM server systems.

The patient communication 14 communicates with a component of a cellular infrastructure. For example, the PPC 14 may communicate with a base station 24 via an air interface. The base station 24 represents a component of the wireless network access infrastructure that terminates the air interface over which subscriber traffic is communicated to and from the PPC 14. A Base Station Controller (BSC) (not shown) is a switching module that provides, among other things, handoff functions, and controls power levels in each base station. The BSC controls the interface between a Mobile Switching Center (MSC) (not shown) and base station 24 in a GSM/GPRS or EDGE mobile network 20, and thus controls one or more base stations 24 in the set-up functions, signaling, and in the use of radio channels.

A BSC also controls the interface between the Serving GPRS Support Node (SGSN) 26 and the base station 24 in such a mobile network 20. The SGSN 26 serves a GPRS or EDGE-equipped mobile by sending or receiving packets via the base station 24 at the mobile interface of the GPRS/EDGE backbone network 28. The SGSN 26 can manage the delivery of data packets to and from the PPC 14 within its service area, and performs packet routing and transfer, mobility management, logical link management, authentication, billing functions, etc. In the exemplary GPRS/EDGE embodiment shown in FIG. 1B, the location register of the SGSN 26 can store location information such as the current cell and Visiting Location Register (not shown) associated with the PPC 14, as well as user profiles such as the International Mobile Subscriber Identity Number (IMSI) of all users registered with this SGSN 26.

Another network element introduced in the GPRS/EDGE context is the Gateway GPRS Support Node (GGSN) 30, which acts as a gateway between the GPRS/EDGE backbone network 28 and a data network(s) 22. For example, the GGSN 30 may serve as a gateway between the GPRS/EDGE backbone network 28 and the Internet, or other data networks such as an Internet Protocol (IP) Multimedia Core associated with IP multimedia subsystems (IMS). The GGSN 30 allows mobile devices such as the PPC 14 to access the data network 22 or specified private IP networks. The connection between the GGSN 30 and the data network 22 is generally enabled through a standard protocol, such as the Internet Protocol (IP).

In the illustrated example involving an EDGE or other GSM-based network, data from the medical device 13 is transmitted "A," received by the base station 24, and forwarded "B" to the SGSN 26 and GGSN 30 for delivery "C" via the data network 22 to the targeted APM server 16A. The PPC 14 may first communicate via a proximity network(s) 32 such as a wireless local area network (WLAN). For example, where the PPC 14 is within a transmission range of a WLAN (e.g., IEEE 802.11b/g network), the PPC 14 can be configured to automatically or manually connect to the WLAN 32. Other proximity networks 32 can also be employed, such as Bluetooth, Zigbee and/or WIMAX. Such proximity networks can address connectivity issues with the mobile network 20, such as within a building where reception can be less than optimal.

In certain configurations, networks are described herein in terms of node networks, although arrangement of the networks as mesh networks is equally applicable to some aspects of the life critical network.

Another embodiment involves ad hoc peer-to-peer (P2P) networking, an example of which is depicted by the peer association 34. A peer-to-peer network does not involve traditional clients or servers, but rather the PPCs 14 serve as nodes functioning as both client and servers to other nodes. In this manner, a PPC 14 can use another patient's 12B, 12C PPC as a relay to the WLAN 32 or mobile network(s) 20. Additional aspects of P2P networking, aspects of which may be utilized in conjunction with the embodiments discussed herein are described in commonly owned U.S. patent application Ser. No. 11/248,879, filed Oct. 11, 2005, which is incorporated herein by reference.

The data originating at the PPC 14 may be stored and/or analyzed at the APM server 16A, which may be further coupled to one or more client stations 36 to perform input and output functions. Methods, structures, and/or techniques described herein, may incorporate various APM related methodologies, including features described in one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

The mobile network 20 can further facilitate data or command transfer from the APM server 16A to the PPC 14. Data can be transferred in reverse sequence ("C," "B," "A"). Other channels may additionally or alternatively be used. For example, one embodiment involves sending commands from the APM server 16A to the PPC 14 using messaging services supported by the mobile network 20 and data network 22 infrastructures. These messaging services include, for example, Short Message Service (SMS), Enhanced Messaging Service (EMS), Multimedia Messaging Service (MMS), etc. These messaging technologies represent "store-and-forward" message services. For example, the APM server 16A may send "D" an SMS message that is received by an SMS Center (SMSC) 38 that provides the store-and-forward functionality, and is responsible for delivering "E" the message(s) to the base station 24 for ultimate delivery "F" to the address of the targeted PPC 14. The SMSC 38 stores the message until the PPC 14 is available, at which time it forwards the message, removes it from the SMSC 38, and notifies the APM server 16A that the message has been forwarded. Issuing commands from the APM server 16A to the PPC 14 using SMS is described more fully below.

MMS, also based on the store-and-forward service model, is similar to SMS in the manner that messages are communicated. However, unlike SMS, MMS is not limited to text messages. The destination address used in an MMS message may be the recipient's public number such as the Mobile Station Integrated Services Digital Network Number (MSISDN), or may be an e-mail address. Therefore, to minimize the chance of the PPC 14 receiving an SMS from an inadvertent source, a lengthy or otherwise unique e-mail address can be contrived and used as the destination address at the PPC 14. To minimize the risk of misdirected messages, messaging techniques such as those described herein may be combined with cryptographic authentication mechanisms to ensure that the PPC doesn't attempt to process and an erroneous message.

It may be desirable, for example, to use a store-and-forward data transfer protocol for less critical data and/or for performing incremental data transfers to/from a server. Use of a store-and-forward transfer protocol may be performed to reduce the volume of data transferred from the PPC to the remote server, yet provide sufficient connectivity between a patient's PPC and remote server.

For example, particular blocks of medical device data of interest may be selectably transferred from the medical device 13 to the PPC 14 in response to command signals generated by the remote server, PPC 14 or medical device 13. Generation of these command signals may result from programmed instructions residing in a memory of the PPC 14 or the medical device, execution of which may be triggered by the PPC 14, medical device or remote server. The programmed instructions may be modified by the physician, typically via the remote server or by an interface to the PPC 14 or medical device.

The physician may be interested in receiving arrhythmia (e.g., atrial or ventricular tachyarrhythmia) related data whenever such event occurs, for example. This selected subset of data is tagged for transfer to the PPC 14 in accordance with the physician's request. Depending on the severity of the event type, the physician may have requested that the event data be automatically transferred to the remote server via the PPC 14 immediately when the event occurs, or, for less serious events, be transferred the next time the PPC 14 connects with the remote server. The PPC 14, prior to establishing communications with the medical device, may be programmed to connect with the remote server and determine if and what specific information is to be acquired from the medical device. This inquiry by the PPC 14 may be performed immediately prior to connecting with the medical device or at some other time (e.g., at off-peak hours or during "cheap" connection times).

The PPC 14 may be programmed to require particular information from the medical device and/or remote server. Various implementations allow the PPC 14 to acquire particular information when needed. For example, the PPC 14 may initiate a real-time interrogation of the medical device, such as by commanding the medical device to wake-up (if applicable) and transmit (or acquire the requested information for transmission) to the PPC 14. The PPC 14 may be programmed to establish communications with the medical device in accordance with a pre-programmed schedule (which may be alterable by the remote server, medical device, or medical device programmer/interrogation device). Alternatively or in addition, connectivity between the medical device and the PPC 14 may be established in response to a remote command, such as a command generated in response to patient-actuated button on the PPC 14.

The remote server may be programmed to require particular information from the medical device and/or PPC 14. Various implementations allow the remote server to acquire particular information when needed. For example, the remote server may initiate a real-time interrogation of the medical device via the PPC 14, such as by commanding the PPC 14 to wake-up the medical device (if applicable) and transmit or acquire the required information for transmission to the remote server via the PPC 14. This scenario is generally reserved for important data, as commanded medical device wake-up and data transfer operations expend energy stores of the medical device. For less important data requests, the remote server may transmit a data acquisition command to the PPC 14 that is to be executed the next time the PPC 14 communicates with the medical device. In this scenario, an unscheduled or commanded wake-up and/or data transmission operation can be avoided. A tiered connection strategy may be employed to effect communications between the remote server, medical device, and PPC 14 that is dependent on a number of factors, including severity of a patient event, power consumption, status of communication link(s) (e.g., availability, quality of service, cost of service), physician/remote server needs, among others.

Upon detection of a physiologic or other event (e.g., arrhythmic episode), selected blocks of data about the event may be selected for transfer to the PPC 14. The selected data blocks typically include data acquired by the medical device during the event, and may be specified to include data temporally surrounding the event that is stored in the medical device's memory (e.g., data stored in a circular buffer representing data acquired n seconds before the event and m seconds after). Histogram, event counter, alerts, and related data may also be transferred in connection with the detected event.

With a constant or quasi-constant "live" connection with the remote server, it is possible to determine what event data for a given patient is presently stored on the server so that collection of duplicative data from the PPC 14 and/or medical device is reduced or eliminated. For example, a patient's implanted medical device (e.g., CRM device) may be interrogated at a clinic by use of a programmer. Prior to transferring data from the implanted medical device, a cross-check can be made between the remote server (via the programmer connected thereto) and the implanted medical device to determine whether data residing in the implanted medical device's memory had previously been transferred to the remote server using the PPC 14. If so, the duplicative data need not be re-transferred to the programmer, thereby conserving implanted medical device energy that would otherwise be expended to transmit the redundant data.

It should be recognized that the present invention may utilize mobile networks 20 other than GSM-based systems. For example, the Universal Mobile Telecommunications System (UMTS) is a 3G mobile technology that may in the future, and in some instances currently, replace GSM/GPRS network infrastructures. UMTS has a different air interface than GSM that can be connected to different backbone networks such as the Internet, ISDN, GSM or other UMTS networks. The PPC 14 can be configured to communicate via a UMTS network or any other existing or future network.

Figure 2A:
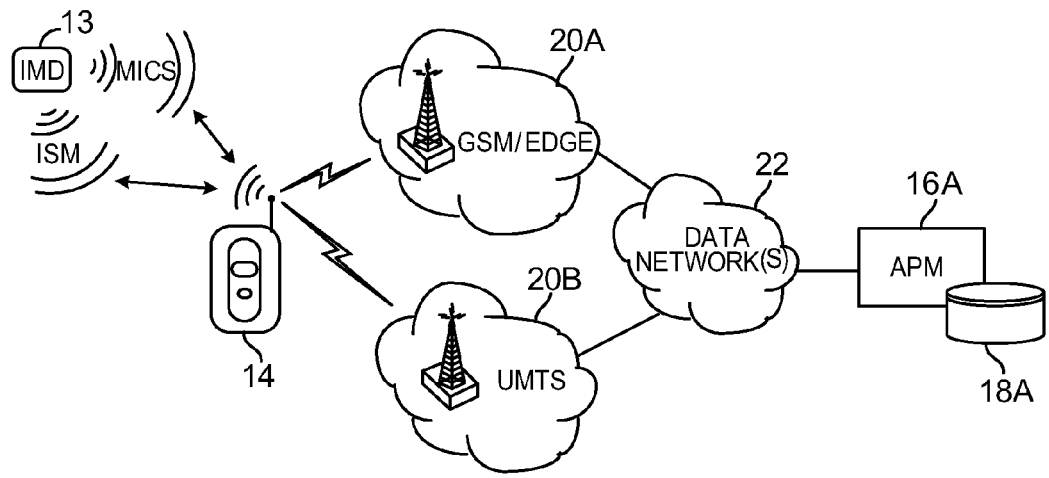
FIG. 2A illustrates a patient implantable medical device configured to operate in various frequency bands or channels for communicating with a portable patient communicator in the context of a life critical network in accordance with embodiments of the present invention.

In one embodiment the system is configured to operate on multiple mobile networks. For example, the air interface of UMTS is not compatible with GSM. As depicted in FIG. 2A, the PPC 14 can be configured as a dual-mode device capable of switching between, for example, an EDGE network 20A and a UMTS network 20B. If a patient equipped with a PPC 14 travels to an area without a first network coverage, the PPC 14 can switch to a second network. The PPC 14 can be configured to switch between a greater number of network infrastructures as well.

In the illustrated embodiment of FIG. 2A, the PPC 14 may ordinarily communicate data with the APM server 16A via a GSM/EDGE network 20A. If the patient moves to an area having only UMTS coverage, the PPC 14 can switch to the UMTS network 20B. In other embodiments network compatibility can be handled at the network level based on, for example, what is contained in the data communicated between the PPC 14 and the APM server 16A. Determination of which network is available can be accomplished in various manners, including determining what country or region the PPC 14 is in based upon the base station signal.

Multiple communication channels may also be provided between the medical device and the PPC. A patient implantable medical device is represented by PIMD 13 in FIG. 2A, which may communicate with the PPC 14 via various communication channels. The PIMD 13 or other medical device may communicate using the Medical Implant Communication Service (MICS), which is a reserved frequency band between 402-405 MHz. Other frequency bands may alternatively be used, such as the Industrial, Scientific and Medical (ISM) radio band, the Short Range Devices (SRD) radio band or others.

FIG. 2A illustrates that the PIMD 13 may be configured to operate in the ISM or MICS frequency bands, or in other channels. While the PIMD 13 may be originally configured for transmission via a single band (e.g., MICS or ISM), other embodiments enable the PIMD 13 to be configured to an appropriate transmission channel. Examples include providing a configurable transceiver module, or providing multiple transceiver modules respectively associated with each of the ISM or MICS (and/or other) frequency bands. The desired band may be designated through remote commands from the APM server 16A or elsewhere. The PIMD 13 may also be configured to automatically switch between communication channels in response to a triggering event. For example, communication between an PIMD 13 and the PPC 14 may switch from MICS to ISM if the MICS transceiver circuitry fails, thereby providing redundancy. The PPC 14 may be configurable in a like manner. For example it may automatically recognize the frequency of the signal and implement the appropriate ISM, MICS, or other circuitry.

The PIMDs 13 acquire the data that is ultimately communicated to the APM server 16A. This data varies depending on the type of medical device involved. In the case of PIMDs, examples of the acquired and communicated data include electrograms (EGM), events, episode counters, alerts, device settings, battery status, lead measurements, patient activity level, and the like. Data may be provided to comply with electronic medical record (EMR) standards. Collected data may be transferred all at once, or incrementally. Requests for data may also include data accumulated over time, such as certain data occurring on a daily, weekly, monthly, or other duration basis. The APM server 16A may selectively request, by way of the PPC 14, particular portions of the data stored in the PIMD or other medical device 13.

The PPC 14 is capable of communicating with the APM server 16A at any time a connection can be made, and thus provides an "always available" functionality. In addition to scheduled data transfers, this "always available" functionality supports event-driven data transfers that are provided in response to an event. Such events may be based on data analysis results, date, time of day, monitored conditions, etc. For example, if a particular patient-related health event occurs, relevant data can be immediately transmitted to the APM server 16A via the PPC 14. Communication of data between the various components may be customized for enhanced operation. Systems and methods involving customized data collection for a medical device which may be useful in combination with the embodiments described herein are provided in commonly owned U.S. Patent Publication No. 20070299317, which is incorporated herein by reference.

Other examples relate to medical device 13 diagnostic or operating conditions. One example is a low PIMD battery condition, which can be sent upon its recognition. Another example is an early memory overwrite warning where a notification can be transmitted when the PIMD memory is at a particular capacity level (e.g., 90%). Yet another example is emergency ambulatory communication of critical patient data. The notification can be used to trigger an interrogation of the PIMD 13 to retrieve the stored data.

Embodiments of the invention also support determining what source device or system interrogated the PIMD 13 or other medical device. For example, the PIMD 13 can be configured to determine whether a programmer or the PPC 14 interrogated the PIMD 13. The medical device 13 can also be configured to record status of data transmissions, including a status indicator(s) indicating whether certain data has already been recorded at the APM server 16A. Status may further include whether a core memory dump has been performed, or a safety core post-process.

In one embodiment the PPC 14 receives and/or transmits device-independent data. Consequently the PPC 14 can operate with different types or models of PIMDs 13 or other medical devices. This can be accomplished by configuring the PPC 14 to the particular type of medical device 13 to which the PPC 14 is, or will be, paired. When interrogating the medical device 13, the PPC 14 can send or forward generic commands such as "send episodes 1-3." This could be in the form of, for example, a style sheet. Alternatively, the PPC 14 can convert data from any type/model of medical device 13 to a common data structure. Data can also be compressed, either in the medical device 13 or the PPC 14, or both.

Life Critical Network

Figure 2B:
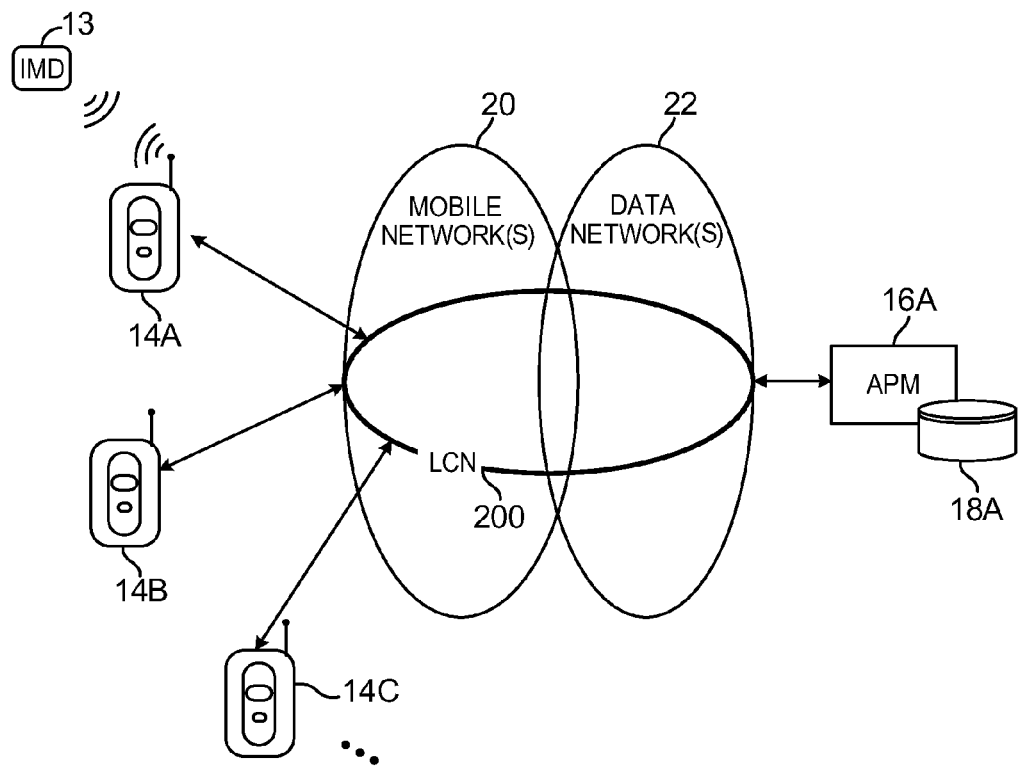
FIG. 2B illustrates a multiplicity of patient implantable medical devices that communicate via a life critical network comprising one or more mobile and data networks in accordance with embodiments of the present invention.

One aspect of the invention involves providing a robust network exhibiting heightened communication attributes such as guaranteed or near-guaranteed delivery, increased quality of service (QoS), tight security, etc. A network exhibiting such attributes according to embodiments of the present invention is referred to herein as a "life critical network" (LCN). FIG. 2B illustrates a PIMD 13 and its corresponding PPC 14A. Any number of additional patients, and respective PPCs 14B, 14C may also be part of the LCN 200.

The LCN 200 essentially represents a private network supported by public network infrastructure. The LCN 200 is configured to operate on top of the existing mobile networks 20 and data networks 22. One feature of the LCN 200 is privacy, in that only devices intended for inclusion in the LCN are allowed. Access control can be accomplished through authentication, which refer to procedures established to verify that the device requesting access to the LCN 200 is the device that it purports to be. For example, a unique identifier(s) from the PIMD 13 may be used as a key to authenticate the device for use on the LCN 200. A more secure process involves specific keys and certificates programmed into the PIMD that allow the PIMD to authenticate messages from the server. The PIMD may use its ability to authenticate the server as a way to authenticate the PPC. A useful authentication method is the "challenge/response" approach described below.

Authentication can be further bolstered in various ways, including encrypting the identifier, or subjecting the identifier to a cryptographic hash function. A cryptographic hash function generally uses a character string or message of any length as input, and in response generates a fixed-length string output often referred to as a digital fingerprint. The unique identifier of the PIMD 13 could be used as the input. Alternatively, the PIMD 13 identifier can be concatenated with a unique identifier of the PPC 14, such as the Mobile Station Integrated Services Digital Network (MSISDN) number (i.e., the "phone number" or other address of the mobile PPC 14) for use with authentication processes. A cryptographic hash function may optionally be applied to the conjoined result and used for access control. These and/or other security measures are employed in various embodiments of the invention.

Authorization processes may also be used at the PPC 14 and/or APM server 16A. Authorization in this sense generally refers to functionality at the relevant device or system that protects the device from communicating unless it is granted authority to do so. Authentication and/or authorization may use unique identifiers or certificates and cryptographic keys to determine whether device functionality (authorization) or network access (authentication) is allowed. For example, in one embodiment, the unique identifier(s) from the PIMD 13 may be used as a key to authorize communication functionality on the PPC 14.

Components of the life critical network may incorporate various methodologies for providing secure and reliable communication, including features described in one or more of the following references: U.S. Patent Publication Nos. 20070118188 and 20070083246, and U.S. Pat. Nos. 7,805,199, 7,801,620, 7,751,901, 7,218,969, 7,203,545, 8,041,032, 8,027,727, and 8,160,704, all of which are incorporated herein by reference.

The LCN 200 can provide virtual connections routed through public networks 20, 22 to separate the traffic of the intended and unintended communication nodes over the underlying networks. Firewalls may also be used, which provides a barrier between the LCN 200 and the public networks 20, 22. These firewalls can restrict the number of open ports, specify what type of packets are passed through, and specify which protocols can pass. Information communicated via these restricted channels can further be encrypted, which involves encoding the data into a form that only the other intended nodes of the LCN 200 can decode. Because the PPC is exposed on the cellular network, a firewall is used to prevent unauthorized access attempts.

Embodiments of the LCN 200 aim to operate as a guaranteed delivery system or a near- or quasi-guaranteed delivery system. For some data and commands between the PIMD 13 and the APM server 16A, timely delivery may be crucial. To approach guaranteed delivery, the LCN 200 implements mechanisms to ensure high quality of service (QoS) transmission. QoS involves various aspects of the connection, such as the time to provide service, echo, loss, reliability, etc.

In addition to guaranteed delivery of data, there may be a need for guaranteed throughput for some data, such as real-time EGM or other monitored cardiac signals. For example, data can be streamed from the PIMD 13 to the APM server 16A via the PPC 14. Streaming data over the LCN 200 can be accomplished in any known manner. Protocols such as the real-time streaming protocol (RTSP), real-time transport control protocol (RTCP) and real-time transport protocol (RTP) enable time-sensitive data to be streamed over data networks. RTP and RTCP are built on the user datagram protocol (UDP), where the data is sent in a connectionless manner in a series of data packets.

Connection-oriented protocols such as the Transmission Control Protocol (TCP) may also be used, as it utilizes acknowledgements to guarantee delivery. While TCP may experience some loss and retransmission delays, some data loss may be tolerable depending on the data being streamed. For example, non-critical, substantially real-time EGM signals may sufficiently provide a clinician with the needed information, notwithstanding some relatively insignificant data loss or latency. Heightened QoS is also implemented on the mobile telecommunication network portion of the LCN 200.

The type of connection and manner of data transmission as between a remote server of the LCN 200, such as server 18A of the APM server 16A, and the PPC 14 may vary depending on a number of factors, including the criticality of the data (e.g., type and criticality of physiological or other patient related data acquired from the patient's medical device, patient sensor or information manually input to the PPC 14 by the patient; nature of a software/firmware update for the medical device or PPC 14; scheduled standard interrogation data vs. patient event/episodic or device diagnostic data; distress of the patient, such as an emergency vs. non-emergency situation; whether data is to be pushed or pulled; geographical location of the patient/PPC 14; available communications infrastructure, whether domestic or international, etc.).

In one approach, the PIMD 13 determines the criticality of the data based on the patient condition or event detected by the PIMD 13. A look-up table of patient condition/event severity versus criticality level may be established for a particular PIMD 13. For example, a look-up table stored in the memory of an ICD may categorize ventricular fibrillation as the most critical level (L1), followed by ventricular tachycardia-1 (L2), ventricular tachycardia-2 (L3), premature ventricular contractions (L4), pacemaker-mediated tachycardia (L5), atrial fibrillation (L6), atrial tachycardia (L7), supra-ventricular tachycardia (L8), premature atrial contractions (L9), etc. Each patient condition/event can have a corresponding criticality level, it being understood that two or more conditions/events can have the same criticality level. In response to one of these or other triggering events, the PIMD 13 preferably transmits criticality level data, along with other data, to the PPC 14.

The connection attributes by which the PPC 14 connects with, and communicates over, the LCN 200 may be based, at least in part, on the criticality level data received from the PIMD 13. For example, the PPC 14 may be programmed to establish a real-time, high QoS connection for high criticality levels, while lower criticality levels may only require a standard QoS connection. The PPC 14 may progress sequentially through a prioritized list of connection types/attributes associated with a given criticality level, until the connection is established. For high criticality levels, for example, the prioritized list may be organized so that the PPC 14 progresses sequentially from most desirable to least desirable connection type/attributes. For low criticality levels, the prioritized list may be organized so that the PPC 14 progresses sequentially from least expensive (e.g., night or off-peak hours) to most expensive connection type/attributes.

It is noted that, in the case of a high criticality level scenario, the PPC 14 may not be able to connect with the LCN 200 (e.g., PPC 14 is in an underground area of the hospital). In such a case, the PPC 14 may include a visual indicator that illuminates, flashes or provides a message prompting the patient (or caregiver) to move to another location so that the PPC 14 can establish a connection. The PPC 14 may also or alternatively produce an aural and/or tactile (e.g., vibratory) output to prompt the patient (or caregiver) to move to another location so that the PPC 14 can establish a connection.

According to another approach, the PPC 14 determines the criticality of the data based on the patient condition or event detected by the PIMD 13. A look-up table of patient condition/event severity versus criticality level may be established for a particular PIMD 13 and stored in a memory of the PPC 14. As in the case of the immediately preceding example, the connection attributes by which the PPC 14 connects with, and communicates over, the LCN 200 may be based, at least in part, on the criticality level data determined by the PPC 14. In addition to PIMD data, it may be desirable for one or both of the PIMD 13 and PPC 14 to use sensor data (implanted or external) to determine or modify the patient's criticality level.

In one embodiment, the particular QoS or other network attributes can change relative to the patient status. For example, data originating from scheduled status transmissions can be communicated using a standard QoS. The QoS of transmitted data can rise as the relative criticality of the data or underlying condition rises. Critical data such as that triggered by a serious cardiac anomaly can be communicated to the APM server 16A, a hospital, an ambulance or other relevant destination using the highest QoS. It may be necessary or desirable to prioritize APM server response/resources based on patient status and/or condition. Criticality of patient condition may be used as a parameter by the APM server to determine which patients to triage first.

The criticality of a patient condition may change after an initial QoS has been determined. For example, an initial QoS or other network attribute may be initially established based on detection of atrial fibrillation. The QoS or other network attribute may adjust in real-time during and/or after the atrial fibrillation episode depending on a change in the patient's status. The QoS or other network attribute may be increased/adjusted if the atrial fibrillation accelerates or if it induces ventricular arrhythmia, for example. Conversely, the QoS or other network attribute may be reduced/adjusted if the atrial fibrillation lessens in severity or terminates either spontaneously or via atrial therapy delivered by an implanted CRM device, for example. This sliding scale of patient status-to-QoS provides the appropriate delivery guarantees based on the particular circumstances.

Various QoS attributes can be controlled in order to provide an appropriate connection for transmitting medical data over the LCN 200. Various QoS attributes may be modified to change connection attributes based on the criticality of the medical data to be transported over the LCN 200. Such QoS attributes may include traffic influencing parameters, such as latency, jitter, packet loss, bandwidth, and response time; management of finite resources, such as rate control, queuing and scheduling, congestion management, admission control, routing control, traffic protection; and service level agreement requirements for flows (e.g., flow-based or aggregated flows).

QoS service methodologies that may be made available for medical data transport include best effort (no QoS), integrated services (hard QoS, IntServ Architecture, see RFC 1633, RFC 2205, RFC 3175), and differentiated services (soft QoS, DiffServ Architecture, see RFC 2475, RFC 3270) methodologies. Another network technology that allows for QoS priority selection is referred to as MPLS (Multiprotocol Label Switching, see RFC 3468, RFC 3209). DiffServ, for example, can be used to provide low-latency, guaranteed service to critical network traffic, such as transport of high criticality PIMD data, while providing simple best-effort traffic guarantees to non-critical network traffic, such as low criticality PIMD data, PIMD-APM server traffic, or routine file transfers.

One approach to implementing selection and/or adjustment of network QoS attributes based on medical data criticality is to establish a mapping of QoS attributes needed to support the LCN network (e.g., a mapping of desired or required QoS attributes based on PIMD data criticality). This LCN QoS schema can be developed by the medical device manufacturer in cooperation with physicians and health care entities, for example. A schema of the public network QoS (e.g., the cellular network(s) and any other data network(s) that are part of the LCN 200) may be developed by the medical device manufacturer in cooperation with the cellular and other network operators, for example. A QoS mapping of LCN QoS-to-public network QoS (e.g., for data transfers from the PPC 14 to the APM server 16) and a mapping of public network QoS-to-LCN QoS (for data transfers from the APM server 16 to the PPC 14) may thus be developed using the LCN and public network QoS schemas.

In accordance with another approach, the LCN 200 may provide enhanced medical data transport using a Wireless Priority Service (WPS). WPS has been developed to provide priority for emergency calls made from cellular telephones. WPS is an easy-to-use, add-on feature subscribed on a per-cell phone basis, with no special phone hardware required. WPS is implemented as software enhancements to existing cellular networks, and is being deployed by cellular service providers in their coverage areas throughout the United States.

WPS provides priority for emergency calls through a combination of special cellular network features. WPS addresses congestion in the local radio access channel (or cell), which is often the reason that cellular calls cannot be made during heavy calling periods or when damage to network infrastructure occurs. WPS automatically provides priority access to local radio channels, placing WPS calls in queue for the next available channel if a channel is not immediately available. Originating Radio Channel Priority requires WPS feature activation on the calling cellular phone. WPS calls do not preempt calls in progress.

When a radio access channel becomes available and the call proceeds, WPS calls are assigned a unique call marking by the cellular network switching equipment. This marking triggers industry standard High Probability of Completion (HPC) features residing in most U.S. telecommunications networks as calls are routed from the originating cell to the called cellular or landline phone. These HPC features significantly increase the probability of call completion should the call encounter network congestion or blockage beyond the originating cell.

Access rights of a PPC 14 to connect to the Wireless Priority Service may be established by medical device manufactures and local and national governmental agencies. The connection attributes or rights by which the PPC 14 connects with, and communicates over, a WPS connection of the LCN 200 is preferably based on criticality level data received from the PIMD 13. For example, the PPC 14 may be authorized to establish a WPS connection for high criticality levels, while lower criticality levels may not qualify for a WPS connection.

As described above, commands may be sent from the APM server 16A to the PPC 14 using messaging services supported by the mobile network 20 infrastructure. One embodiment of the invention involves using Short Message Service (SMS) or "text messages" to direct commands to the PPC 14 for ultimate delivery to the PIMD 13. Verification techniques may be employed to ensure that an SMS message from an unauthorized source is not inadvertently addressed to the PPC 14 and perceived as a command. In one embodiment, a subset of the data in the SMS message may be used by the PPC 14 to verify that the SMS message originated from an authorized source (e.g., APM server 16A). One example involves the PPC 14 comparing the source address (e.g., MSISDN number) of the SMS message with a stored list of approved source addresses. In another exemplary embodiment a code may be inserted into the SMS message itself. For example, a standard SMS message supports 160 characters, and the first predetermined number of characters may represent a code used by the PPC 14 to verify that the sender is genuine. The code may be the concatenated PIMD/PC identifiers signed with the APM server's private key. The APM server's private key can be verified by both the PPC and the PIMD as they have the public key for the server in their set of certificates.

Figure 3:
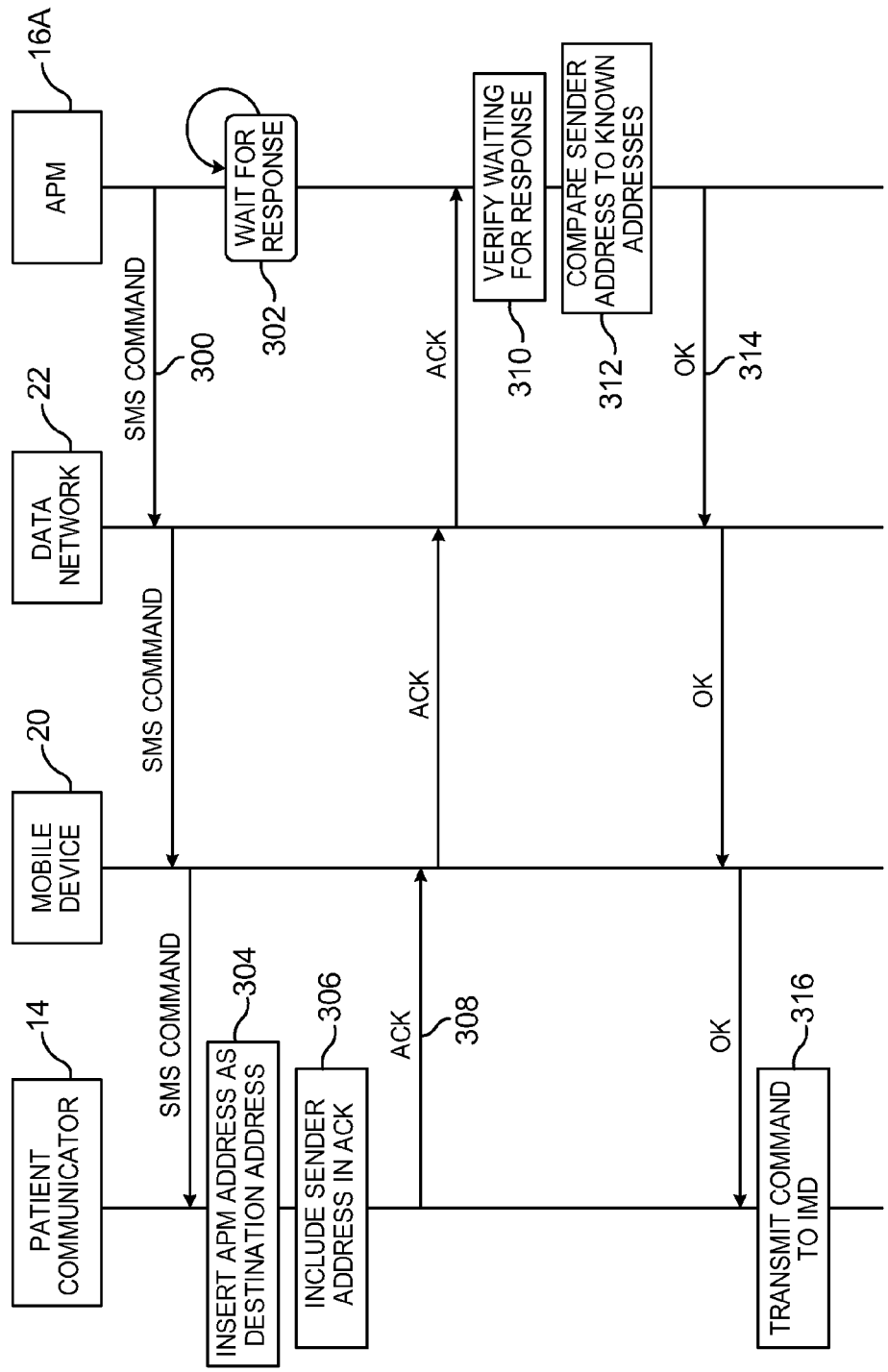
FIG. 3 is a message flow diagram illustrating one manner of using acknowledgment messages to verify the source of an SMS message communicated between a remote server and a portable patient communicator via a life critical network in accordance with embodiments of the present invention.

Message verification techniques utilizing handshaking may also be used. FIG. 3 is a message flow diagram illustrating one manner of using acknowledgment messages to verify the source of the SMS (or other) message. Such a handshaking embodiment enables the PPC 14 to verify that the command originated at an APM server 16A or other authorized source before forwarding the command to the PIMD 13. This may be beneficial, for example, where the PPC 14 is unaware of the APM server 16A source address. The PPC 14 may be generally unaware of APM addresses, or new APMs having new source addresses may be added to the system unbeknownst to the PPC 14.

Operationally, the APM server 16A may direct a command to the PPC 14 via an SMS-based command 300. If the APM server 16A was in fact the source of the SMS message, it enters a wait state 302 or otherwise notes that it has initiated the message. The command is forwarded through the data and mobile networks 22, 20, and arrives at the PPC 14. Rather than "reply" to the source address of the incoming SMS message, the PPC 14 inserts 304 a known APM address as the destination address. Thus, even if the SMS message originated at an unauthorized source, the resulting acknowledge message (ACK) 308 is directed to the APM server 16A. Additionally, the sender's address (i.e., the source address identified in the received SMS message) can be included 306 in the responsive ACK message, for reasons discussed more fully below.

When the ACK 308 arrives at the APM server 16A, it verifies 310 that it was in a wait state, waiting to receive an ACK message from the PPC 14. If it was not, it can be assumed that the SMS message received at the PPC 14 was not issued by the APM server 16A, and the APM server 16A can notify the PPC 14 as such. Further, the sender address provided by the PPC 14 in the ACK message can be compared 312 to a set of known APM addresses, if multiple APM and corresponding APM addresses exist. If the received sender address does not correspond to any known APM addresses, it again can be assumed that the original SMS message received at the PPC 14 was not initiated by the APM system. If the received sender address matches a known APM address, the APM sends an OK 314 or other confirmatory message to notify the PPC 14 that the original SMS message was indeed issued by the APM system. Upon receipt of the OK 314 message, the PPC 14 can transmit 316 the command embodied within the SMS message to the PIMD 13 or other medical device paired with the PPC 14. Additional or alternative processes for message verification that may be used are described in commonly owned U.S. Patent Publication No. 20070185547, which is incorporated by reference herein.

When using the SMS medium, the security keys and identifiers included in the text message need to be smaller than the character limit for SMS. In one approach, a key that the APM server recognizes may be embedded in the text message. A simple encryption approach may be used, which involves sending medical data without patient-identifying information, and including the medical device serial number or the SIM (Subscriber Identity Module) serial number.

Streaming data from the PIMD 13 or other medical device over the LCN 200 and to the APM server 16A via the PPC 14 may be enabled and disabled in a number of ways and in response to varying conditions, triggers or events. The manner and paths by which PIMD data is streamed over the LCN 200 may be based on events or patient conditions such as criticality of the data, distress of the patient, and whether or not an emergency call has been attempted via a 911 service, among others.

A PPC 14 may be programmed so that its behavior relative to the LCN 200 and/or the PIMD 13 is dynamically adjusted based on predetermined conditions. For example, if the PPC 14 detects that it is out of range of the PIMD 13, the "status" of the PPC 14 on the LCN 200 may be changed (e.g., reduced). The status of the PPC 14 refers to the level of capabilities granted a particular PPC 14 when operating over the LCN 200. A PPC 14 that is out of range of its corresponding PIMD 13 may have a reduced ability to communicate with the APM server 16, such as by being denied access to certain functions (e.g., over-the-air PPC firmware upgrades, PIMD interrogation or programming commands) and data that are appropriate only when the PPC 14 is in range of its paired PIMD 13.

By way of further example, use of cellular phones and devices is often restricted in most areas of hospitals and health care clinics, but permitted in lobby areas. During a hospital or clinic visit, it may be desirable to establish communication between the PPC 14 and the LCN 200/APM server 16, particularly during extended visits. Assuming that the patient is restricted to his or her room, a caregiver may take the PPC 14 to the lobby or other permitted area and establish a connection with the LCN 200/APM server 16. Granting authorization to the caregiver may involve some form of authentication, such as thumbprint, voice, or PIN code authentication, for example. The PPC 14 may be configured with appropriate hardware and software to perform this "third party" authentication, which will vary depending on the manner of authentication (e.g., a thumbprint reader, voice-recognition circuitry).

The present "status" of a PPC 14 may not be apparent to the patient until a connection with the APM serve 16 is attempted, either automatically or by actuation of a manual sync button on the PPC 14 that initiates an upload/push data operation, for example. If the patient attempts to use the wrong PPC 14, an indication of the PPC's reduced status is preferably indicated in some visual, aural or tactile manner to the patient. Although basic data may be transferred out of the PPC having a reduced status, full uploading/functionality may only be granted to a properly paired PPC, although high priority/criticality data/events would likely be excepted.

Tiered functionality may be programmed into the PPC based on correct or incorrect pairing. There may be scenarios where incorrect pairing is detected, but the location of the PPC indicates that a PPC's status need only be minimally reduced (or not at all). Scenarios where incorrect pairing occurs, but where there is a high level of confidence that the PPC 14 is in the right location for the patient, include multiple PPC scenarios, the PPC in the office, home, clinic, physician's office or hospital, the PPC in a nursing home, and the PPC in a pharmacy (via the pharmacy's Wi-Fi that can be identified as such).

The effectiveness of the LCN 200 depends in large part on the reliability of the cellular network or networks that facilitate connectivity between PPCs 14 and the APM servers 16. Various techniques can be implemented to improve data transmission efficiency and reliability through the LCN 200. A forward error correction approach, for example, may be implemented by which data is re-sent multiple times from the PPC 14 (e.g., data redundancy).

An approach to determining appropriate connection attributes for a PPC 14 may involve determining latency of transmission between the PPC 14 and the APM server 16. One approach to determining this latency is to determine round trip time (RTT), such as by use of a ping service, which may be initiated by the PPC 14. In response to receiving a ping packet transmitted by the PPC 14, the APM server 15 sends back a response packet (i.e. performs a no-op). A ping operation does not involve performing packet processing, so the RTT measured by the PPC 14 is a relatively accurate measure of round trip latency. The PPC 14 may be programmed to perform a ping operation and consider RTT when determining appropriate connection attributes for connecting to the LCN 200.

Depending on the criticality of the data, the PPC 14 may be programmed to negotiate a higher output power from the cell tower(s) or an increase in the PPC's network interface transmission power on a temporary basis. In general, a conventional cellular phone is not permitted to adjust its network interface power output with respect to the particular cell towers over which it is presently communicating. Rather, network interface output power of cell phones communicating over particular cell towers is moderated by those cell towers. A cellular network operator may cooperate with the medical device manufacturer of the PPCs 14 to offer special services for patient subscribers that use the operator's cellular network to support the LCN 200.

These special services may include the PPC 14 negotiating a higher output power from cell tower(s) for transmitting critical data. Alternatively, or in addition, the cell tower(s) can raise its base power. These special services may include adjusting the QoS for transmitting critical data and/or change the carrier frequency to a frequency that minimizes interference with other connections. Unique information (codes or profile packets/bits) may be transmitted from the PPC 14 that indicates a request for special services is being made which is recognizable by the cellular network operator. Based on the data's criticality level, one or more connection attributes may be adjusted by the cellular network operator in response to the PPC's request.

Embodiments of the invention are directed to tiered approaches for communicating data over a life critical network. A tiered or prioritized approach to communicating medical data over a network is particularly beneficial in cases where non-ideal infrastructural conditions exist or arise, such as dead spots or undesirable tower interaction in a wireless communication system, and where patient condition can vary dynamically between normal and life-threatening. A tiered approach facilitates exploitation of different communication protocols and mediums for different clinical data, events, and/or priority.

According to some embodiments, the PPC 14 implements control logic to determine the proper communication protocol and medium for exchanging data with a remote server based on the purpose and priority/urgency of the data exchange and/or infrastructural status. The PPC 14 may, for example, have different physical channels of communications available to it, such as a telephone line, cellular, Wi-Fi, etc. Not all of these physical channels are always available, and they have different costs, performance characteristics, and levels of service. Cellular technology, for example, allows for a number of different mechanisms for data exchange, each with different levels of service, throughput, and purposes (e.g., raw data, SMS, email, and others).

The PPC 14 and remote APM server 16A have many different reasons to exchange data. Data transmission from/to the PPC 14 and APM server 16A occurs at different frequencies, some are physician or patient initiated, and some are medical device manufacturer initiated. These data have different priorities, including urgent, nominal, or low priority, or even optional. The PPC 14, according to some embodiments, may be configured to determine some or more of the degree of urgency, purpose of the data exchange, the cellular network's current capabilities, and the transport mechanisms available.

In accordance with an illustrative example of a tiered communications approach as between a PPC 14 and a remote APM server 16A, it is assumed that the highest degree of priority or urgency is associated with an emergency or time critical situation, such as when therapy delivery is ineffective or all therapies are exhausted. In such cases, the PPC 14 is preferably programmed to utilize all communications protocols and mediums available to it. Some of these channels may be reliable while others may be unreliable. Parallel messages over multiple channels (data channels, SMS, two cell towers, Wi-Fi to local network) are preferably transmitted by the PPC 14 in an attempt to reach the APM server 16A. The PPC 14 preferably sends the same urgent message on all the mediums.

According to one approach, the PPC 14 sets a unique identifier for the message to be delivered on all mediums. The same identifier is used on all of the messages triggered by the same event. The APM server 16A may receive one or more of the urgent messages through any of the channels. The APM server 16A utilizes the unique identifier and identifies that the messages are the same. The APM server 16A only acts on one of the messages—acting on more than one is redundant. A unique stamp may be used to verify this is the same message, albeit received from disparate mediums.

In response to receiving the message from the PPC 14, the APM server 16A preferably sends an acknowledgement back to the PPC 14. The acknowledgement includes the unique identifier. When the PPC 14 receives the acknowledgement, it discontinues transmitting the urgent message. If the PPC 14 does not receive an acknowledgement, it continues to retry/transmit the urgent message at some regular interval.

Continuing with this illustrative example, it is assumed that an alert based on patient data represents the second highest priority or urgency level. A typical "red" alert indicates that there is a problem with the medical device or patient's health condition that needs to be communicated to the APM server 16A (e.g., "Not in Monitor+Therapy Mode" alert condition). In response to an alert condition, the PPC 14 first attempts to use the configured cellular/mobile data network interface. Using a cellular/mobile medium, the clinician receives the alert sooner than when using a once-per-day scheduled check of the PPC 14 initiated by the APM server 16A. If the cellular/mobile medium or other data interface is not available, the PPC 14 attempts a more simpler form of data exchange, such as a store-and-forward exchange (e.g., SMS).

The third highest priority or urgency level according to this illustrative embodiment may be for problems with the PPC 14 where the patient is in an unmonitored state (i.e., unmonitored by the APM server 16A). A problem with the PPC 14 may be detected by the APM server 16A, such as by detecting non-receipt of PPC data for a predetermined period or failure to receive such data in accordance with a predetermined schedule. The APM server 16A may also detect an unmonitored patient state by pinging the patient's PPC 14 and failing to receive a response from the patient's PPC 14 within a predetermined period of time. The APM server 16A, in response to detecting loss of connectivity with the patient's PPC 14, may attempt to establish communication with the PPC 14 using all mediums and protocols available to it, preferably using a tiered approach. For example, the APM sever 16A may attempt to use a data network followed by use of SMS.

The PPC 14 may detect loss of APM server connectivity using strategies similar to those discussed above but initiated by the PPC 14. If, after implementing a tiered strategy for attempting to connect with the APM server 16A, the PPC 14 determines that such attempts have been unsuccessful, the control logic of the PPC 14 may execute a procedure to draw patient awareness to the present problematic state of the PPC 14. The PPC 14 can, for example, flash an alert light or message on a display or broadcast an audible alert. Other approaches may be used, such as activating a vibrating element of the PPC 14 or other tactile transducer. These and other methods of attracting the patient's attention may be implemented, such as in a tiered approach based on factors such as power consumption, likelihood of success, or predetermined preferences established by or for the patient. The patient, upon detecting an alert initiated by the PPC 14, may contact the physician or PPC manufacturer or service for assistance.

The fourth highest priority or urgency level according to this illustrative embodiment is for data exchanges to and from a physician or clinician. Data transfers to the physician is effected in a manner discussed previously with regard to implementing a tiered approach for transferring data from the PPC 14 to the APM server 16A over the LCN 200. For data transfers from the physician to the PPC 14, a store-and-forward medium or protocol is preferably used, since the PPC 14 may not be presently connected to the APM server 16A. According to one approach, a physician (or r technician) preferably defines an interrogation schedule, and the APM server 16A pushes the interrogation schedule to the PPC 14. This approach may be supplemented by scheduled (or commanded) PPC pulls from the APM server when the PPC 14 connects with the APM server 16A.

Clinicians may push data to the PPC 14 from the APM server 16A for a variety of reasons other than, or in addition to, performing PIMD or PPC interrogations. For example, physician directed data may be pushed to the PPC 14 to prompt the patient to take some action, such as to take drugs (e.g., maintain prescribed medication regimen, titrate diuretics, activate or adjust drug delivery device), take some type of measurement (e.g., weight, oxygen saturation, blood pressure, heart rate), or interact with a sensor (e.g., blood pressure cuff, weight scale, glucose sensor), among other actions. The clinician may analyze certain data and effect some form of communication to the PPC 14 via the APM server 16A.

The fifth highest priority or urgency level according to this illustrative embodiment is for notifying the patient that a data transmission failed after repeated attempts. This message class includes messages for prompting the patient to contact the medical device company if the PPC 14 is unable to communicate properly. A sixth highest priority or urgency level is for performing routine interrogation of the PIMD 13.

The seventh highest priority or urgency level according to this illustrative embodiment is for evaluating status of the PPC 14. This message class consists of very low priority information that can be lost or not collected. It consists of diagnostic information not critical to the patient, physician, or the system operation. Accordingly, a low cost transport mechanism (e.g., SMS) is preferably selected. The transmission of low priority content may be delayed for lower cost periods of the day/night.

The manner in which a multiplicity of PPCs 14 connect with, and communicate over, the LCN 200 may be controlled to reduce overall network usage. For example, the quantity and type of content of the data transmitted over the LCN 200 (uni- or bi-directional) may be adjusted (increased or decreased) by the APM system operator as needed or desired. Data content and transmission attributes may be modified on-the-fly for one or a multiplicity of PPCs 14, which may affect the PPC(s) 14 future behavior by causing it/them to not send as much data or to send more data, depending the need. The APM system operator may, for example, control all PPCs 14 in group-wise fashion, such as by reducing or disabling data content transmission from the PPCs 14 or by commanding all PPCs 14 to transmit full data content with diagnostics, including communicator and SIM identification data, for example.

The manner in which data is to be exchanged between the PPC 14 and APM server 16A may be impacted at least in part by the cellular infrastructure. For example, a message or settings may be sent from the APM server 16A to all or appropriate cell towers that will pass the message or settings on to one or more of the PPCs 14. The message or settings may be delivered to the PPC(s) 14 in a variety of ways, such as part of a normal tower-communicator cellular exchange, a queued transmission at off-peak hours, or as part of a PPC 14 being powered-up and setting up the cellular connection.

LCN Connection Strategies

The efficacy of a life critical network depends in large part on the capability of the LCN to facilitate transport of critical medical data (e.g., CRM device data) over a public cellular network infrastructure in a secured and time-efficient manner. A variety of methodologies may be employed to maintain and enhance LCN efficacy. For example, the integrity of the communication link between the PIMD 13 and PPC 14 may be enhanced by performing block transfers of PIMD (e.g., IPG) data snapshots into a buffer for transfer to the PPC 14. This approach may advantageously avoid dropouts between the PIMD 13 and PPC 14. As was discussed previously, PIMD data transferred to the PPC 14 may be transmitted over the LCN 200 in a number of ways, including a session based connection or an ACK-based connection. Suitable transport approaches include automatic retry query (ARQ), TCP, and UDP streaming, among others.

Another approach involves transmitting an urgent message or important/critical data to multiple cell towers, such as two towers. The message/data can first be transmitted to the cell tower that provides the best signal quality followed by transmissions of the same message/data to the tower(s) with lower signal quality. Variations of this approach are discussed hereinabove.

In cases where a preferred LCN connection is not available or becomes unusable, alternative connections may be sought in accordance with a predetermined priority scheme. For example, should a preferred connection such as a high QoS cellular connection become unavailable, a PPC 14 may attempt to connect to the LCN 200 using a data channel (e.g., Ethernet connection), MMS, SMS, Wi-Fi, or low-speed modem over a voice channel (to operate as a modem to transmit data), for example. If a patient has no cell coverage, intermittent coverage, or periodic (e.g., day/night) coverage, a predetermined priority scheme may include switching to a Wi-Fi network as backup. The Wi-Fi is preferably preconfigured to provide efficient connectivity between the PPC 14 and the LCN 200. Another fallback is to attempt a connection using any network that can be found by the PPC 14.

When out in public, several opportunities for connecting to the APM server 16A may be exploited. In one approach, a public kiosk or Wi-Fi access point (e.g., municipal, within a store or coffee house, at a pharmacy) may be used. A tiered connection and data transport strategy may be implemented in accordance with the type of connection made.

For example, a greater range of PPC functionality may be granted if the PPC 14 connects with the APM server 16A via a pharmacy or hospital's wireless access point, relative to a generic public access point. Several network service discovery mechanisms may be used by the PPC 14 to facilitate discovery of available network services, including ultra low-power mechanisms (e.g., via Bluetooth). Another approach involves hopping onto another person's cell phone who is in proximity with the patient's PPC 14. Yet another approach involves an ISM to ISM scheme, which can be a relatively long range mechanism (e.g., 200 meters) that provides complete control of a radio. This approach would allow the PPC 14 to connect (i.e., bootstrap) to another PPC 14 or cell phone via ISM radio, and then using the cell phone for establishing a network connection.

According to another approach that involves a docking station or hub for the PPC 14, a message or indicator may be communicated to the patient by the hub or PPC 14 to dock the PPC 14 to the hub. Assuming the hub has an alternative medium to connect to the LCN 200, such as POTS connection, this alternative medium can be used to connect the PPC 14 to the LCN 200.

Another approach involves the PPC 14 indicating to the patient to move to another area where coverage is available. The PPC 14 may indicate to the patient that a message needs to be transmitted and the patient should try to go to a known good cellular coverage area or dock their device.

In cases where PPC data is collected at a scheduled time, such as during the night), but there is no coverage when patient is at rest, a number of actions may be performed. A store-and-forward procedure may be implemented when the connection becomes available. Another action may involve a mechanism to notify the patient, especially is the case of an emergency (e.g., red alert) condition. If the data is not received by the APM server 16A or the PPC 14 does not get a signal for a predetermined period of time, the patient is preferably notified (e.g., a phone call to the patient's home, an email or SMS message to the patient's cell phone).

Some classes of devices, as controlled by their SIM, may have higher priority for using the cellular infrastructure, such as police, fire, and emergency medical personnel (e.g., higher priority via a Wireless Priority Service connection). During normal operation with no emergency data, the PPC 14 preferably utilizes normal SIM settings and receives the commonly available cellular service. If the PPC 14 has emergency data to be delivered, the PPC 14 preferably registers with the emergency-class SIM to utilize the special-availability class of service. It is important to change the emergency priority designation based upon status to avoid always using emergency channel.

If the cellular network is full or otherwise inaccessible, the PPC 14 may be programmed to re-attempt a connection at appropriate intervals, which would preferably involve attempts to connect via alternative mediums. Should the PPC 14 ultimately fail to connect to the LCN 200, a message or indictor is preferably presented on the user interface of the PPC 14 (or broadcast via an audible message or tactile output) prompting the patient to contact his or her physician or medical device manufacturer.

International travel by a patient can present a number of challenges when attempting to connect to the LCN 200 via the PPC 14. When traveling in an airplane or on a cruise ship, the PPC 14 is preferably programmed to connect to the LCN 200 via an airborne or shipboard communications network. For example, the PPC 14 is preferably configured to access an airliner's cellular access point via a wireless protocol, such as onboard Wi-Fi device (e.g., AirCell 802.11 a/b/g wireless access point or an 802.11 n wireless access point). A typical airborne cellular network deployment includes three towers mounted on the exterior of the plane, which beam to ground stations in the United States. A similar approach is employed in Europe and elsewhere. Some airlines provide Ethernet and USB ports in each seat which can be used to provide LCN connectivity. When cruising, the patient may connect with the LCN 200 via a global maritime cellular operator that is accessible throughout the cruise ship. The shipborne radio networks, typically GSM or CDMA, are generally linked to public networks via satellite.

The PPC 14 may provide the option to operate in "flight mode," in which the transceiver used to connect to a wireless network is turned off. The wireless transceiver that communicates with the PIMD may remain on or may be switched to a short range power setting (or may be turned off as well). The PIMD transceiver of the PPC 14 may incorporate a wake-up detection circuit that "listens" for an emergency wake-up signal from the PIMD. This emergency signal may be a low-power RF signal, an acoustic signal, or other signal that does not (or only minimally) interferes with onboard communications systems.

The PPC 14 may be set to "flight mode" by actuation of an appropriate button on the PPC 14 (or by voice command activation). A flashing light or other indicator is preferably generated to indicate to the patient that the PPC 14 is in "flight mode." After the flight, the flashing light or indicator prompts the patient to switch off the "flight mode." Various automatic techniques may be employed to ensure that the PPC 14 does not remain indefinitely in "flight mode" should the patient forget to switch this mode to off. One approach involves using a timer, which starts when "flight mode" is selected, to turn off "flight mode" upon expiration. The timer may be set to a duration that guarantees that the flight will have concluded, such as 24 hours, for example.

In the case of a PPC 14 communicating with LCN 200 via an EDGE network, the PPC 14 can have from 1 connection up to 5 connections. The number of connections controls the data rate. When the EDGE network is busy, the number of PPC connections is reduced (e.g., from 4 down to 1). The PPC 14 can detect how many connections are available to it, and modify its behavior accordingly. The PPC 14 utilizes the EDGE and cell tower information to determine how much bandwidth might be available, and to determine if the medium is appropriate for the message's priority/urgency. This information can be included in the APM system's dashboard diagnostics, which is discussed below.

For example, the PPC 14 may detect availability of a large number of connections, which allows the PPC 14 to stream data, such a real-time EGM data, to the APM server 16A. When a reduced number of connections is detected, the PPC 14 adjusts its data output rate and/or content to allow for data transfers at the reduced data rate. The PPC 14 preferably requests more bandwidth based upon urgency. The PPC 14, based on the message priority/urgency, preferably requests the cell tower for more EDGE channel connections. This request feature may be one of the "special services" accorded a PPC 14 as discussed previously.

Dashboard Diagnostics/Interfaces

Figure 9A:
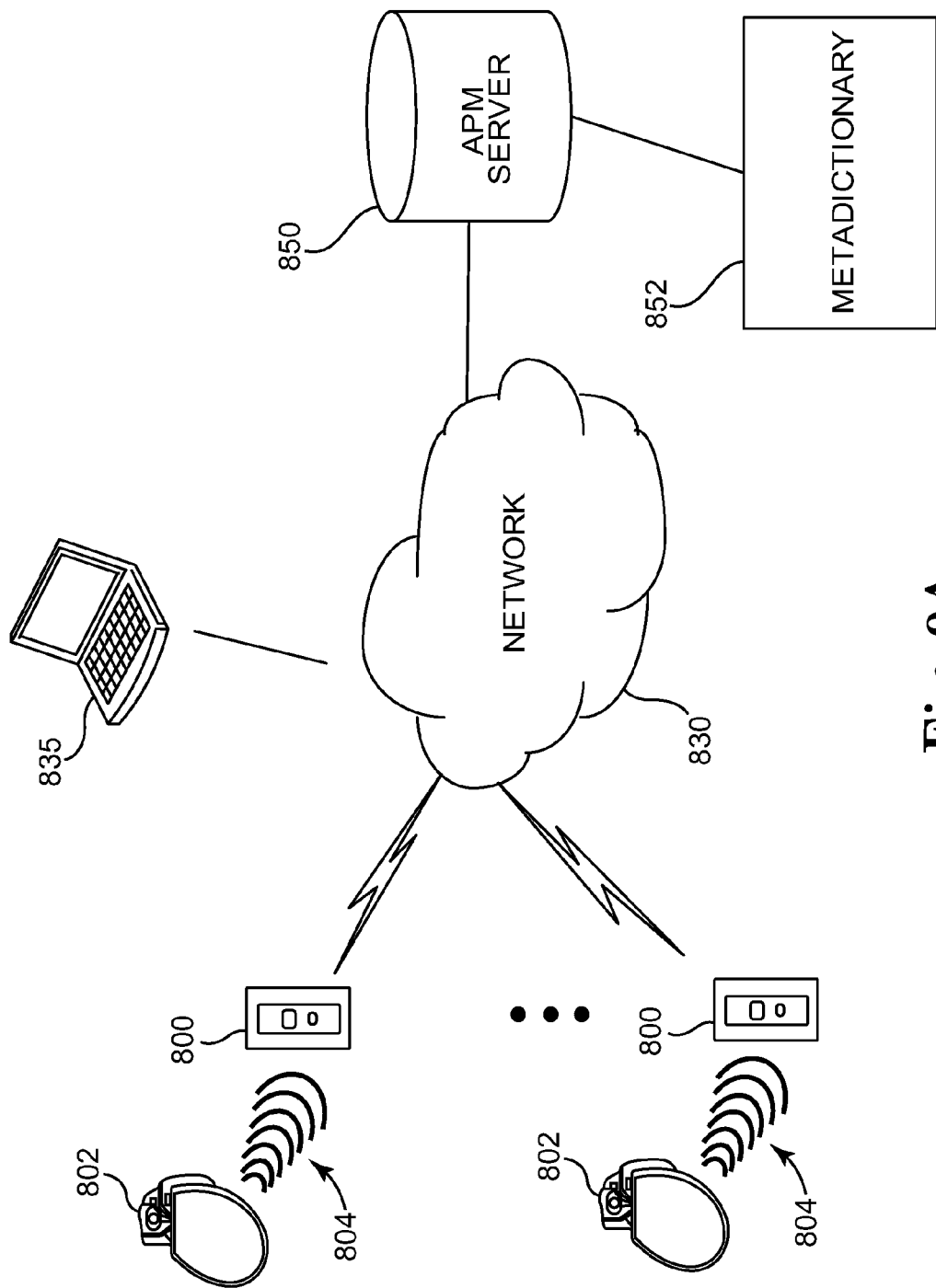
FIG. 9A shows an illustration of a multiplicity of PPCs communicatively coupled to an APM server via a network in accordance with embodiments of the present invention.
Figure 9B:
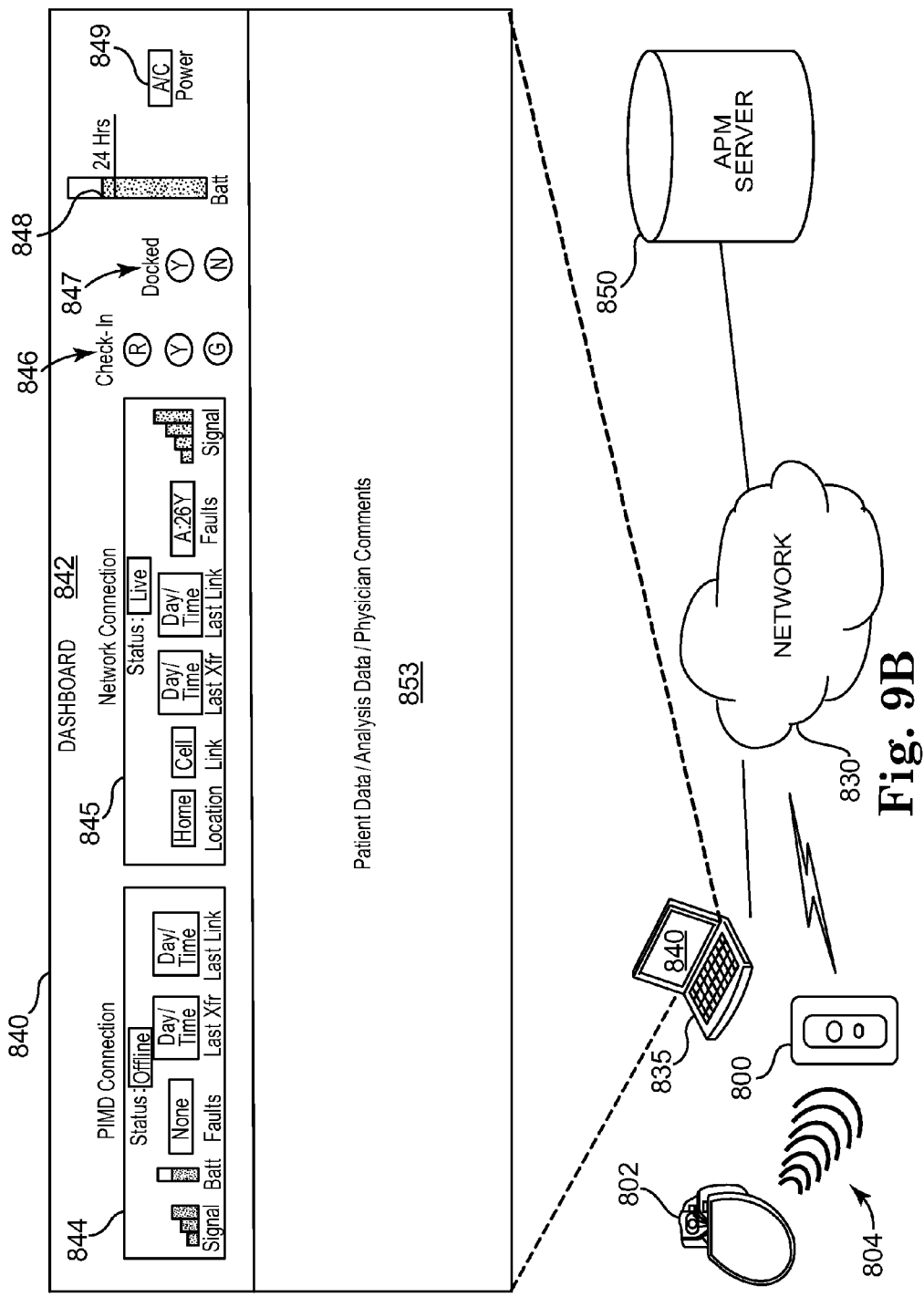
FIG. 9B is an illustration of dashboard diagnostics accessible to local and remote users in accordance with embodiments of the present invention.

The physician or other authorized person may interact with the APM server to access a variety of information concerning a particular patient, the patient's medical device, and/or the PPC. FIGS. 9A and 9B, for example, show a user access device, such as a laptop or PPC 835, that provides authorized access to an APM server 850 via a network 830 (e.g., LCN). The laptop 835 may reside at the physician's office, home or other location (e.g., vacation hotel room). A dashboard diagnostic can be executed on the laptop 835 that, in general, shows information about the status of the PPC 800 and the patient's medical device (e.g., implanted CRM device or other PIMD). The dashboard diagnostic, analogous to an automobile's dashboard that has a variety of gauges and indicators, provides useful diagnostic information about the "health" of the PPC's connection with a communication medium (e.g., cellular network) and with the PIMD 802 or other medical device or sensor with which the PPC 800 communicates.

The dashboard or other APM server-based application may be implemented to provide support for near real-time functions, such as PIMD 802 and/or PPC 800 interrogation, EGM and/or other sensor data streaming, over-the-air reconfiguring, software updating (e.g., PIMD firmware updates) and programming (e.g., modifying device parameters or initiating physician commanded functions). Application level packets may be transmitted to request information, and data mining may be performed on the PIMD 802 or PPC 800 by the physician or authorized user. For example, a dashboard application may provide for remote initiation of clinician commanded atrial shock therapy. By way of further example, a dashboard application may allow an authorized user to command the PPC 800 to effect a scan of the PPC's local environment for RF interference. Data acquired from this scan can be shown on an "interference" indicator of the dashboard.

A procedure may be established by which certain information is acquired or exchanged with a PPC 800 that connects with the APM server 850. In general, it is preferably that the PPC 800 communicate with the APM server 850 via a cellular network connection, by which the PPC 800 will interact with the cellular network and exchange information packets with the APM server 850. The PPC 800 is preferably programmed to periodically check-in with the cellular network and with the APM server 850. The PPC 800 may check-in several or many times per day with the cellular network and generally checks-in only once or twice per day (under normal conditions) with the APM server 850.

During a cellular network check-in by the PPC 800, the PPC 800 obtains network/connectivity information such as signal strength, signal band/protocol, or other cellular network information/statistics. During an APM server check-in by the PPC 800, the PPC 800 exchanges patient PIMD/sensor data and further shares a sub-set of that network/connectivity information about its connectivity with the APM server 850, primarily if the PPC 800 has a good connection (e.g., signal strength, quality of service). Selected types of PIMD and network connectivity information may be presented on the dashboard 842.

Various types of diagnostic information acquired by the PPC 800 are preferably made available to the physician or authorized user via a dashboard display 842, which may be presented in a region of the display 840 of a laptop 835 as shown in FIG. 9B. In addition to dashboard information, various types of patient information received from the APM server 850 may be displayed in a patient data portion 853 of the display 840. As with the patient related data, the dashboard data is preferably pulled from the APM server 850 by way of a secured network connection to the laptop or personal computer.

As can be seen in the dashboard 842 in FIG. 9B, a dashboard diagnostic operating on a physician or other authorized user's laptop or personal computer 835 is configured to primarily show connectivity and status information about the PPC 800 and PIMD 802. The layout of the dashboard 842 shown in the embodiment of FIG. 9B includes a PIMD Connection window 844, a Network Connection window 845, a Check-In indicator 846, a Docking Status indicator 847, a Battery Status indicator 848, and a Power Status indicator 849. It is understood that the type and number of data windows and indicators shown in FIG. 9B are for illustrative purposes, and that other of different informational content and manners of displaying same are contemplated.

The Network Connection window 845 provides various information regarding the connection between the PPC 800 and the network 830. The Network Connection Window 845 indicates the present connection state between the PPC 800 and the network 830 (e.g., "live" or "offline). Such information includes whether or not the patient's PPC 800 is presently connected to the network 830 and by what means (e.g., cellular, land-line, satellite, etc.). As shown, the dashboard 842 shows that the PPC 800 is presently connected to the network 830 (i.e., Status: "Live") and that the present connection is via a cellular connection (i.e., Link: "Cell"). It is noted that additional details concerning the "Link" may be displayed, such as by clicking on the "Link" label/button. The strength of the connection between the PPC 800 and the network 830 is shown, such as by use of commonly used signal strength bars. Any faults that have occurred can be viewed in a Fault window.

Other information shown in the Network Connection window 845 includes the day/time of the last or previous contact between the PPC 800 and the network 830/APM server 850, and the last day/time data was transferred between the PPC 800 and the APM server 850. If the physician wishes to see details about the last transfer of information or last connection, additional information may be presented by clicking on the "Last Xfr" label/button or "Last Link" label/button. Still other information includes the location status of the PPC 800, such as whether the PPC 800 is presently stationary (e.g., at the patient's office or home) or mobile. The Location indicator of the Network Connection window 845 shows that the PPC 800 is presently at the patient's home.

A PIMD Connection window 844 of the dashboard 842 provides various information regarding the connection between the PPC 800 and the PIMD 802. The PIMD Connection window 845 indicates the present connection state between the PPC 800 and the PIMD 802 (e.g., "live" or "offline). As shown, the dashboard 842 shows that the PPC 800 is presently not communicating with the PIMD 802 (i.e., Status: "Offline"). The strength of the connection between the PPC 800 and the PIMD network 830 (present strength if connected or of last connection) is shown, such as by use of commonly used signal strength bars.

Other information shown in the PIMD Connection window 844 includes the day/time of the last or previous contact between the PPC 800 and the PIMD 802, and the last day/time data was transferred between the PPC 800 and the PIMD 802. If the physician wishes to see details about the last transfer of information or last connection, additional information may be presented by clicking on the "Last Xfr" label/button or "Last Link" label/button in PIMD Connection window 844. Further information includes the status of the PIMD battery and the fault and/or alert status of the PIMD 802. If the physician wishes to see details about the PIMD faults or alerts, additional information may be presented by clicking on the "Faults" label/button.

The dashboard 842 may include other informational indicators, such as a Check-In indicator 846. The Check-In indicator 846 provides information based on the PPC's most recent connectivity information upload. In the illustrative example shown in FIG. 9B, the Check-In indicator 846 includes a multi-state indicator comprising three colored indicators; red (i.e., circled "R"), yellow (i.e., circled "Y"), and green (i.e., circled "G"). When the physician clicks on a patient's detail page, such as that shown presented in display 840, the physician can see the state of the "red—yellow—green" indicator 846.

If the PPC 800 has not checked-in with the APM server 850 within some time period, the Check-In indicator 846 will show "red." If the PPC 800 has checked-in with only a low/moderate indication of signal strength, the Check-In indicator 846 will show "yellow." If the PPC 800 has checked-in regularly (e.g., 2 or more times within a specified time period) with good signal strength, the Check-In indicator 846 will show "green."

Based on a "green" indication, the APM server web page can allow a physician to initiate an "active connection" with the PPC 800. It is desirable (or may be mandatory) that an active connection be established when both the PPC 800 and the PIMD 802 are not mobile, which may be determined based on the stability of signal strengths or other means. When a non-mobile active connection of sufficient strength is established, the APM server's user interface can allow the physician to initiate an active session. An active connection can allow for a variety of operations, such as real-time streaming of EGMs, physician-initiated interrogation, sending a message to the patient, and remote programming, among others. The APM server's web site can also allow some actions to be performed, even if there can not be an active connection. For example, various types of messages can be transmitted to the PPC 800 or queued to transmit to the PPC 800 when a cellular connection is established.

The PPC 800 may incorporate a display that includes some or all of the indicators provided in the dashboard 842, although various embodiments of the PPC 800 may have a limited user interface, such as in the case of a reduced feature-set PPC 800. For example, the display of the PPC 800 may display an indication to the patient about signal strength (e.g., signal strength bars). It might only display the exception (e.g., yellow or red LED in cases where there is either unstable or no connection). An indicator of the PPC 800 may offer some indication to the patient that a physician/clinical user of the APM server's web site has established an "active connection" with the PPC 800. An alert status indicator (e.g., red LED) may be programmable by the physician/clinical user and activated via the APM server's web site to alert the patient of a problem, thus prompting the patient to contact the physician or APM service representative.

In the Network Connection window 845, an indication of the present location of the PPC 800, in the case of a live connection, or the most recent location, in the case of an offline status indication, is provided to the physician or authorized user. This location information may be used for a variety of purposes, including estimating the stability of the connection if an important data transfer operation is to be conducted (e.g., a PIMD or communicator firmware update), and changing the connection attributes, data access rights, and/or functionality of the PPC 800 depending on location (e.g., greater rights/access granted if at home versus overseas), among others. It is noted that, if the connection status indicator in the Network Connection window 845 indicates that the PPC 800 is "Offline," the most recent dashboard information is presented. The manner in which the location of the PPC 800, including the present geographical location of the PPC 800 if not at the patient's home, may be determined is discussed hereinbelow.

The dashboard 842 will indicate if the PPC 800 is mobile and if it is at its "home" location. As previously mentioned, this can be important for determining if the patient is likely at their place of residence (or other known location such as the patient's office) and if the quality of the cellular connection is likely to be stable. The PPC 800 has a setup procedure, performed once during setup, that will ask the user "are you currently in your home location?" and allow the user to respond with Yes/No. This location can be determined by cell system features. This location can also be identified by the set of cell towers and relative signal strength from each. The PPC 800 stores this "home profile" in internal memory so that it can be tracked later. The Network Connection window 845 of the dashboard 842 will indicate "Not at Home" when the set of cell towers/signal strength does not match the home profile.

A number of indicators tracked by the PPC 800 can be used to determine if the PPC 800 is "mobile" or stationary. For example, a PPC 800 that is switching to multiple different cell towers within a predetermined time period (e.g., the last 10 minutes) is considered mobile. A PPC 800 that has large variations in signal strength with the same cell tower within a predetermined time period (e.g., the last 10 minutes) is considered mobile. Various known cellular-based locating techniques (e.g., triangulation) may be used to determine the present location of the PPC 800. In some embodiments, a GPS receiver may be provided on the PPC 800 or be communicatively coupled (wirelessly or wired) to the PPC 800. For example, a Bluetooth enabled GPS receiver implemented in a portable housing or a GPS receiver integrated into automobile electronics may be paired with the PPC 800 and provide high precision location information to the PPC 800. This location information may be transmitted to the APM server 850 and made available to the physician. An indication of the present location of the PPC 800 is preferably presented on the dashboard 842.

The dashboard 842 is shown to include a docking status indicator 847, a battery indicator 848, and a power status indicator 849. The docking status indicator 847 indicates whether or not the PPC 800 is presently docked with its corresponding base station or hub (e.g., "Y"=Yes if docked to its home hub or "N"=No if not docked to its home hub). A PPC 800 will generally have a corresponding "home" hub that resides at the patient's home, but may also have additional hubs, such as a hub that resides at the patient's office. A portable or travel hub may also be used by the patient when traveling, which may incorporate additional features and functionality, such as a power source converter for connecting with international power sources and a GPS receiver that provides the present location of the travel hub (and, therefore, provides a good estimate of the patient's location).

A PPC 800 is considered at its "home location" and not mobile when it is physically connected to its home hub (or other known "stationary" hub). The power status indicator 849 of the dashboard 842 will indicate if the PPC 800 is currently powered by the hub's battery source or an AC power adapter. The power status indicator 849 allows the physician to know in advance if there is an external source of power for the PPC 800, so that power will not run out during a live communication session. The battery indicator 848 of the dashboard 842 indicates the relative battery energy level of the PPC 800. The battery indicator 848 allows the physician to know if there is enough internal battery power, so that power will not run out during a live communication session. The battery indicator 848 may also include an indicator to show whether the internal battery power of the PPC 800 is sufficient to provide 24 hours of PPC operation. This information may also be provided on the patient's home hub display so that the patient/physician can be assured that a full day's charge is available.

The information provided on the dashboard 842 allows the physician to assess how the patient is using the PPC 800, such as whether the PPC 800 is in communication range, being properly charged, turned on, etc. Over time, the set of status data from the PPC 800 accumulates in the APM server 850. This allows for a report or user interface to show the patient, clinician, or medical device sales representative how effective the patient's use of the PPC 800 has been. Various metrics may be computed, trended, and displayed, such as the percentage of time the PPC 800 contacts the PIMD 802. This provides an indication of how many times PIMD contact was attempted and the number or percentage of successful contacts.

Other useful metrics include an indication of the PPC's average battery power (e.g., the PPC's charge history), whether the patient is keeping the PPC 800 properly charged, how many times the battery has been completely exhausted, and how long the PPC 800 was completely off or inaccessible. The degree of mobility may be a useful metric that indicates whether, and to what extend, the PPC 800 is moving or not. This provides an indication of whether patient is actually taking the PPC 800 with them during their normal activities. This can provide an indication of patient health and quality of life. For example, a mobility metric can show if the patient is active. Metrics can be generated that can be used to assess patient compliance and to implement compliance training Various reports, statistics, and user interfaces can be used to identify to the patient if they are not keeping the battery charged or not carrying the PPC 800 with them, and encourage the patient to take corrective actions. Patient compliance information can also be generated and presented that reinforces and encourages proper use of the PPC 800 by the patient.

It is contemplated that other dashboards can be implemented that provide useful data for particularized users. For example, a dashboard may be implemented that is oriented towards the clinician/physician. A separate dashboard may be implemented that is oriented towards more network diagnostic. Other dashboards may be implemented that are oriented towards customer service centers for purposes of enhancing troubleshooting efforts by technicians and clinicians.

Moreover, diagnostics other than those discussed above can be shown on a dashboard 842. Such diagnostics include the following: frame error rate of the cellular network connection, frame error rate of the implanted device connection; state of the PPC/PIMD connection (e.g., not-connected, attempting implant connection/wake-up, connected, failed/not-connected); current number of attempts to contact/wakeup the PIMD; last time the PPC had a user interaction (e.g., button pushed, placed on or removed from the docking station); transfer rate metrics (e.g., minimum bps, maximum bps, average bps) for the most recent data transfer; and timestamped connectivity link change history (e.g., GSM→WifF→GSM) since the PPC connected to the network. Other diagnostics and metrics are contemplated. Dashboard information may be updated at a relatively slow rate, such as once per hour (or faster or slower as desired) Dashboard information may also be updated upon command. Dashboard information may be updated in response to a connection being established between a PPC and the APM server 850.

Updating the firmware of the PPC 800 may be implemented using the dashboard diagnostic or other facility of the APM server 850. The PPC 800 may be viewed as having different sets of firmware. A first set of PPC firmware may be termed medical firmware, a second set of PPC firmware may be termed user interface firmware, and a third set of PPC firmware may be termed cellular radio firmware. These sets of firmware operate substantially independently yet cooperatively to seamlessly effect communications between a governmentally regulated "medical device" (e.g., an implanted CRM device, which is a classified by the FDA as a Class III medical device) and a public communications infrastructure (e.g., cellular network and the Internet). The procedures and requirements for updating different sets of PPC firmware are quite different.

The cellular radio firmware controls the interactions and communications to and from the PPC 800 and the cellular network. This firmware must be independently versioned, tested, and controlled in conjunction with the network providers. The cellular radio firmware is typically upgraded without the need for patient interaction, and can be actioned for upgrade by the cellular network provider or through the APM server 850.

The user interface firmware controls the visual and/or audio content of the PPC 800. The user interface firmware also contains the audio recordings for any sounds generated by the PPC 800. This firmware is updated preferably over-the-air, without involvement from the user. It is controlled by the APM server 850.

The medical firmware controls the activities schedule of the PPC 800, communications between the PPC 800 and the PIMD 802 and other sensors, and data transfers to and from the APM server 850. The medical firmware, for example, ensures that all communications between the PPC 800 and the PIMD 802 conforms to predetermined medical device guidelines, which may include regulatory guidelines that conform to security, encryption, and privacy (e.g., HIPAA) requirements promulgated by a regulatory body, such as the U.S. Food and Drug Administration. The medical firmware also ensures that all communications between the PPC 800 and the network 830 and APM server 850 conform to such regulatory guidelines or requirements. This firmware is updated preferably over-the-air, without involvement from the user.

Over-the-air programming (OTA) is also referred to as over-the-air service provisioning (OTASP), over-the-air provisioning (OTAP) or over-the-air parameter administration (OTAPA), or firmware over-the-air (FOTA), each of which defines methods of distributing new software/firmware updates to cellular phones or provisioning handsets with the necessary settings with which to access services such as WAP or MMS. OTA via SMS, for example, can be implemented to optimize the configuration data updates in SIM cards and handsets, and enable the distribution of new software/firmware updates to mobile phones or provisioning handsets. OTA messaging provides for remote control of mobile phones for service and subscription activation, personalization and programming of a new service for network operators, for example.

In general, the APM server 850 is able to communicate to the cellular network provider and/or queue a message that is general to all PPCs 800. The message is preferably pushed from the APM server 850/network 830 to the PPCs 800 over the least expensive medium and during off-peak hours. An "upgrade available" broadcast message preferably causes the PPCs 800 to initiate communications to the APM server 850 during an off-peak hour, and possibly at a randomized interval to avoid server/network overload, to commence with the upgrade download. The PPCs 800 may use the hub communication medium to contact the server and download the upgrade.

The PPC 800 preferably includes software and hardware that support OTA upgrading. New software or firmware may be transferred from the cellular network provider (or the APM server 850) to the PPC 800, installed, and put into use. It may be necessary to turn the PPC 800 off and back on for the new programming to take effect, which can be programmed to occur automatically at a time when PPC services are not required (e.g., patient is sleeping with no anomalous physiologic conditions detected).

An OTA software or firmware upgrade session can be initiated automatically at an appropriate time or in response to a patient's input. For example, the cellular network provider or APM server 850 can send an SMS message to the PPC 800 requesting the patient to enable the OTA software/firmware upgrade, such as by actuating an update button on the PPC 800. In response, the PPC 800 dials a service number to receive a software/firmware update. It is understood that other modes of performing software/firmware upgrades for the PPC 800 may be used, such as by establishing a wired connection with a server of the cellular network provider or the APM server 850. It is further understood that all or selected groups of PPCs 800 can be upgraded concurrently, such as by the cellular network provider or the APM server 850 broadcasting an SMS message indicating that an upgrade is needed or by performing the upgrade automatically at an appropriate time.

According to some embodiments, firmware upgrades are performed by the cellular network provider pushing the firmware updates to one or more PPCs 800. The updates are tracked on a per-radio basis, such as by use of SIM identification. Firmware updates for each of a PPC's cellular radio firmware, user interface firmware, and medical firmware is tracked and made accessible on the dashboard 842. Notification of a firmware update is generated by the cellular network provider and received by the APM server 850. The update receipt is preferably pulled in by the APM server 850. A check is made to determine if all designated PPCs 800 were successfully upgraded. For PPCs 800 that either did not receive the update (e.g., PPC 800 out of range, poor connection, or turned off) or failed to successfully implement the update (e.g., update was interrupted), the updating procedure is repeated. As was mentioned previously, the updates can be coordinated and delivered by the cellular network provider, the APM server 850 or both.

Generally, the cellular network operator is able to determine which PPCs 800 have what versions of firmware. Reports are typically available to determine which PPCs 800 have older firmware revisions that still need to be updated. These PPCs 800 can be re-targeted for a firmware update. Patients who have these PPCs 800 can be contacted by a customer support representative.

When the PPC 800 is connected to the network 830 and signal strengths and time of day/patient condition are appropriate, a firmware upgrade package is delivered to the PPC 800. The signal strength and battery need to be consistent for a complete transmission. The appropriate time of day can be determined according to network availability and data transfer fees. Night-time/low utilization periods should be preferred. As an alternative implementation for firmware updates, all firmware updates may be sent to the cellular network provider. The cellular network provider preferably uses over-the-air transmission for installing the updates, and the cellular network identifies the PPCs 800 that need the upgrade.

As was previously discussed, the status of each set of PPC firmware is preferably made available on the dashboard 842. Firmware status and updates are preferably tracked on the basis of individual PPC radio, typically by way of SIM data. It may be desirable to provide two or more dashboards, each tailored for a particular user. For example, a physician dashboard may include higher level/summarized information relating to the patient or a group/population of patients, the connected state of the PPC(s) 800, availability of active-connection(s), and patient compliance. In general, the physician does not need all of the detailed connectivity information that is available. A customer service dashboard may include full details, including actual signal strengths, diagnostic information, etc. The customer service dashboard may also provide information about groups or populations of patients and/or users. For example, data about what fraction of patients/users are currently connected, recently connected, out of range, etc., may be accessed via the customer service dashboard, which can provide customer service personnel with valuable information about problem areas that can be further investigated in greater detail.

A PIMD programmer dashboard may be implemented that provides information of particular use to physicians that are accustomed to using a traditional implantable medical device programmer. In general, most of the information that is of interest about a PPC 800 also applies to a PIMD programmer that is connected and on a cellular network. For example, information and trending data on the connectivity status of PIMD programmer, such as signal strengths and percentage of time connected, can be obtained and presented on the programmer dashboard. Information regarding the last check-in by the PIMD programmer, including data, time, and interrogation information, is preferably transferred to the APM server 850 from the PIMD programmer and presented on the PIMD programmer dashboard. The location where a particular programmer is and/or where a given interrogation occurred can be determined and tracked. For example, a programmer is generally an expensive piece of equipment, and it is important to have programmer information for equipment tracking, determining equipment location and availability, and determining equipment servicing needs.

During use, the PIMD programmer can store data in its internal memory for later upload to the APM server 50. The programmer can indicate that it has data ready for upload/streaming and, when connected to the network 830, the programmer can upload the data to the APM server 850. Data associated with implanting a PIMD, for example, can be stored in the programmer's memory for real-time or later transfer to the APM server 850. By way of example, during a PIMD or other medical device implant procedure, a number of records are written, logged, typed, and printed. All or selected records associated with the implant may be communicated from the programmer to the APM server 850. This implant data may be accessed and evaluated by physicians, clinics and hospital personnel and data systems, and medical device manufacturer representatives, for example.

The PIMD programmer can be used to facilitate an active session with the APM server 850 and the PIMD 802, in a manner like the PPC 800. Features such as real-time EGM streaming, for example, are made available. The software and firmware installed on each programmer must generally be tracked by the medical device manufacture to meet tracking requirements. The current version of programmer software, firmware, and other configuration and diagnostic information about the programmer is preferably uploaded to the APM server 850 and made available on the PIMD programmer dashboard.

PPC/Programmer

According to some embodiments, a PPC 800 may be configured for use as a component of the in-clinic/operating room PIMD programmer. In this regard, the PPC 800 is configured as a "dual use communicator," in that the PPC 800 is used as a programmer in clinic and as a communicator out of clinic.

The PPC 800 can be paired/assigned to the patient and the PIMD at the time of implant. The PPC 800 is utilized as a "smart wand" during the implant operation and initial follow-ups. The patient could be enrolled in the APM system at this same time. Advantageously, the PPC 800 stays with the patient as the patient leaves the operating room.

The PPC 800 can be used as a "smart wand" that communicates with the PIMD via telemetry and to the programmer user station via another RF link (e.g., Wi-Fi or Bluetooth) or other information system/laptop computer. When used during PIMD implant, the data can be transferred between a laptop (e.g., used by the PIMD sales representative), PPC 800, PIMD, and programmer. In one configuration, direct communication between the laptop and the PPC 800 is effected using a Bluetooth link.

At the time of implant, the PIMD sales representative typically records a large amount of patient information (e.g., name, age, physician's name, notes) and PIMD information (lead models, serial numbers, IPG model/serial number, etc.). The sales representative types this information into the information system's laptop. The sales representative must then re-enter the same information into the programmer's user interface. Rather than re-input this information, the sales representative may instead press a "program to patient communicator" button on the laptop. The data is then transferred to the PPC 800. Rather than using the programmer for PIMD data transfer, the PPC 800 then programs this data to the PIMD, thus acting as a "smart wand" and eliminating duplicative entry of the patient information.

One benefit obtained when using the PPC 800 as a "smart wand" is that the patient/PIMD is monitored immediately after the PIMD is implanted. Alerts and monitoring are active immediately and available during the patient's stay in the hospital and immediately after discharge. The patient is able to be trained and familiarize themselves and family members with the PPC 800.

Pairing the PIMD with the PPC

One aspect of the life critical network involves the process of pairing the patient implantable medical device with a PPC. Pairing communicatively links a PPC with a particular PIMD to form a unique PIMD-PPC pair. Pairing is typically performed during an initialization process and occurs before patient specific data can be transferred between the PIMD and the PPC. Re-pairing may need to be performed in the event that one or both of the paired devices is replaced or loses pairing information.

Pairing involves exchanging or otherwise providing pairing information to one or both devices that is used to communicatively link devices in a unique PIMD-PPC pair. Pairing information may include device identification information, patient identification information, cryptographic keys, and/or other information that can be used to establish and maintain a secure and reliable communication link between the PIMD and its paired PPC. Pairing information is typically maintained within the PPC and/or the PIMD and may be provided, exchanged and/or developed before or during pairing between the PIMD and the PPC.

Figure 4A:
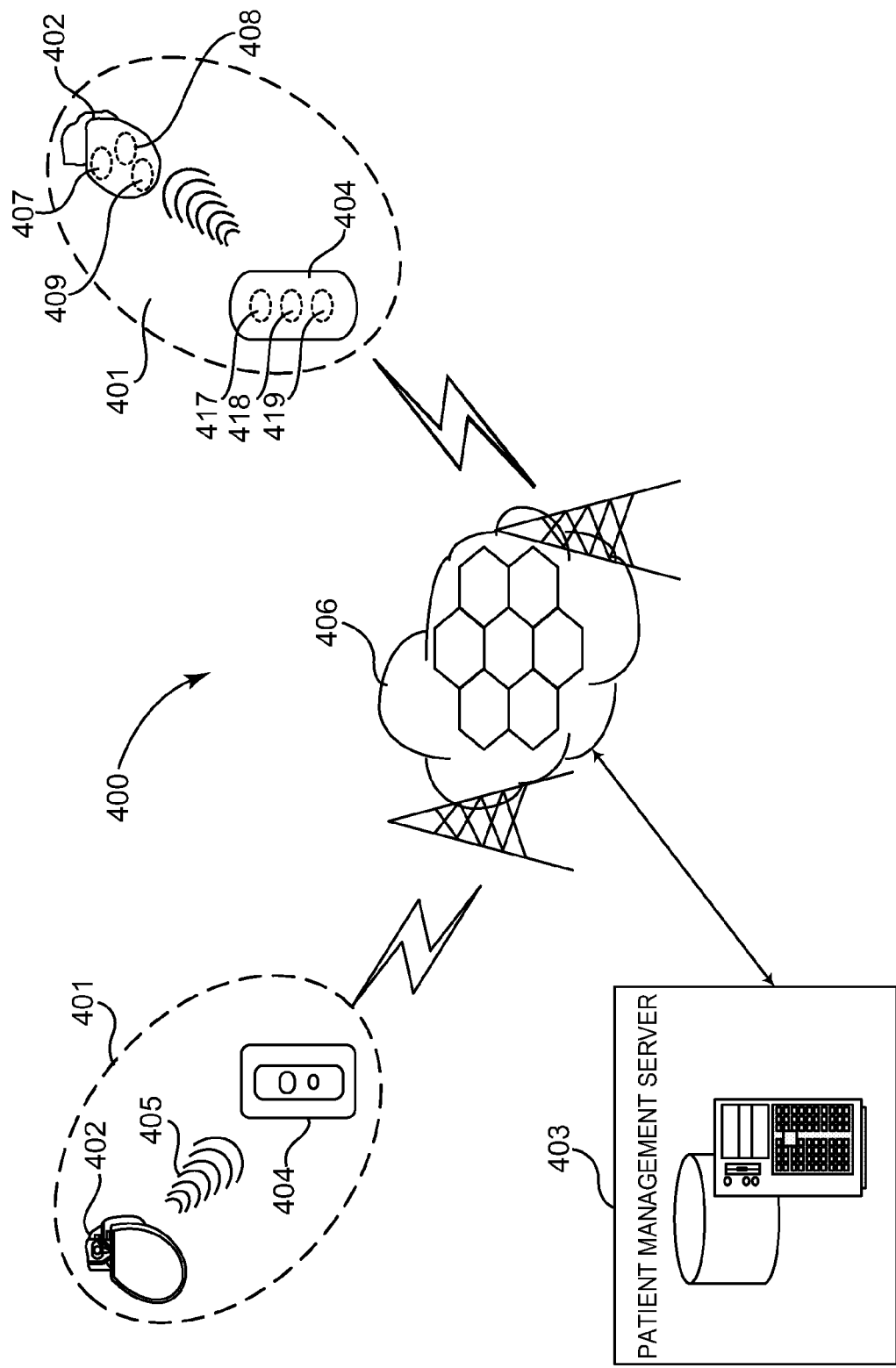
FIG. 4A illustrates a multiplicity of PIMD-PPC pairs and an APM server in a life critical network in accordance with embodiments of the present invention.

FIG. 4A illustrates a plurality of PIMD-PPC pairs 401 and an APM server 403 in a life critical network 400. The PIMD 402 and the PPC 404 of each PIMD-PPC pair 401 are paired by a bi-directional communication link 405 between the PIMD 402 and PPC 404. For example, the bi-directional communication link 405 may involve RF telemetry utilizing MICS, ISM, SRD, or other appropriate radio bands. Following a pairing process that uniquely links a PIMD 402 and PPC 404 to form a PIMD-PPC pair 401, information may be transferred between the PIMD 402 and its linked PPC 404 via the RF link 405 and between the PPC 404 to the APM server 403 via a cellular network 406.

The PIMD and/or PPC may include one or more components and/or processes to facilitate pairing and/or to allow interaction between the PIMD-PPC pair and the patient. For example, as described in more detail herein, the PIMD 402 and/or PPC 404 include software, firmware and/or hardware 407, 417 that stores pairing information and/or stores and executes the program commands used in the pairing process. The PIMD 402 and/or PPC 404 may also include sensors 408, 418 used to verify proper pairing, determine proximity of the PIMD 402 to the PPC 404, and/or to provide patient incentives that encourage the patient to carry the PPC 404 so that the PIMD 402 and PPC 404 can maintain communication. The PIMD 402 and/or PPC 404 may also include components and/or processes 409, 419 used to generate an alert or provide for other types of communication with the patient.

Figure 4B:
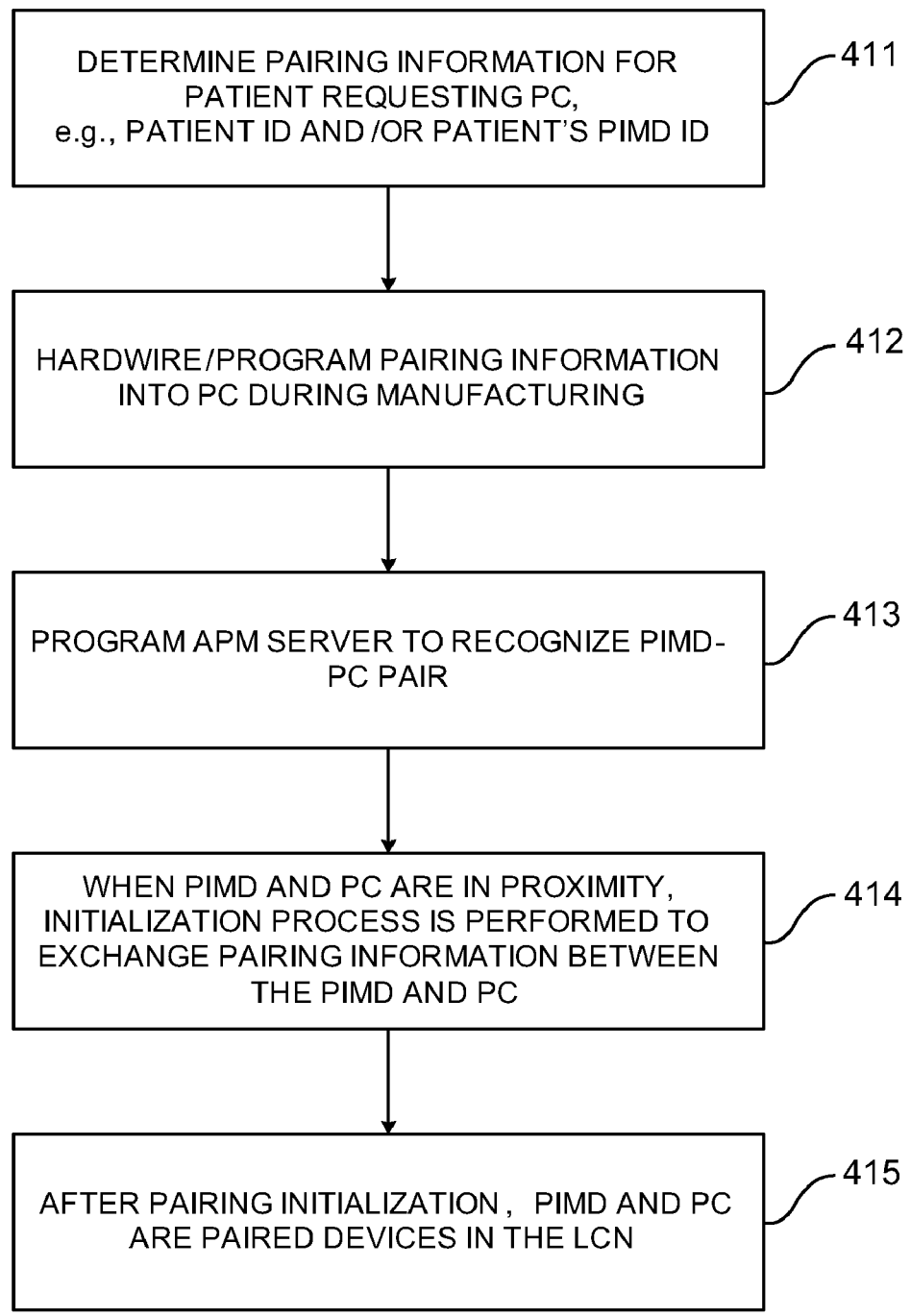
FIGS. 4B-4F illustrates various methodologies for performing pairing as between PIMDs and PPCs in accordance with embodiments of the present invention.

In one scenario, and with reference to FIG. 4B, pairing information that is used to communicatively link a particular PPC with a particular PIMD may be permanently stored in the PPC and/or PIMD. For example, as illustrated in FIG. 4A, after information about a patient and/or the PIMD of a patient requesting a PPC is determined 411, pairing information may be stored 412 in the memory of the PPC during manufacturing. For example, when the PPC is destined to be paired with a particular PIMD, the PIMD ID and/or the patient ID is hardwired into the PPC or flashed to a flash programmable ROM of the PPC. The APM server of the life critical network is programmed 413 to recognize the PIMD-PPC pair.

The PPC is then transferred to the patient that is implanted with the particular PIMD. When the patient's PIMD is in proximity with the PPC, a pairing initialization process is performed. The pairing initialization may be started, for example, by command from the APM server or by pressing a button on the PPC that puts PPC into pairing initialization mode. The PPC interrogates the PIMD to start 414 a pairing initialization process that pairs the PIMD and the PPC. During the pairing initialization, the PPC may query the PIMD requesting that the PIMD send pairing information (e.g., the PIMD ID) to the PPC. The PPC confirms that the pairing information acquired from the PIMD matches the pairing information hardwired or programmed into the PPC. If so, the PIMD and the PPC are paired by the initialization process. Additional information to facilitate secure communication between the PIMD and the PPC may be transferred from the PPC to the PIMD. If the pairing initialization is successful, a secure communication link connects the PIMD-PPC pair and establishes 415 the PIMD and PPC as paired devices in the life critical network.

One authentication mechanism that may be used to pair the PIMD and the PPC is the "challenge/response" approach. A PIMD or PPC wanting to authenticate another device creates a random challenge message and sends it to that device. The device receiving the challenge message adds a timestamp and signs it with a private key (from a public/private key pair). The signed response is returned to the challenger, who can check it with the public key. If it passes, and the time stamp is "recent," then the challenger knows that the other device really has the private key. As long as keys are secured, the receiver has to be the authentic owner of that public/private key pair. Authentication can also be performed with symmetric keys, if a means is provided to ensure that the same key is in both systems in a secure manner, but a public key infrastructure (PKI) may be preferred for some applications.

A PIMD can be manufactured to include the public certificate for the server. The server has a private key well secured, such as secured in hardware encryption modules. The PPC has a private key, and the server has the public keys for all manufactured PPCs. However, the PIMD may not have enough memory to store the public keys for all PPCs, or the PIMD may be implanted before its associated PPC is manufactured.

In a single transaction, the server can authenticate the PPC, and then provide those authentication credentials to the PIMD—there is a "chain of trust"—the PIMD can trust the server, so once the server authenticates the PPC, it can "vouch" for the PPC to the PIMD. Once the PIMD can trust the PPC, it can pair with it—they can exchange secure keys for future sessions.

Pairing information may be programmed into the PPC and/or PIMD during a clinic visit. Pairing information that is programmed in the PPC and/or PIMD at a clinic visit provides a more flexible option than programming or otherwise embedding the pairing information into the PPC and/or PIMD during manufacture of the devices. In one scenario, pairing information may be flashed to ROM in the PPC or otherwise stored in memory of the PPC while the patient is at the clinic to ensure that the PPC and PIMD devices are correctly paired. Flash programming the PPC with pairing information may be performed at a physician's office, hospital, clinic, or other medical facility having equipment for programming the PPC. In some implementations, the PIMD may also be programmed at the clinic with pairing information that corresponds to the pairing information programmed into the PPC. Programming the PPC and/or the PIMD and performing pairing initialization during a patient visit to the clinic allows the clinic to have a number of unpaired PPC's on hand which can then be provided to patients on an as-needed basis. The use of unpaired PPCs that can be later programmed to be paired with PIMDs significantly reduces the administrative effort required to ensure that a patient receives the PPC which contains pairing information that allows pairing with the particular PIMD of the patient.

Figure 4C:
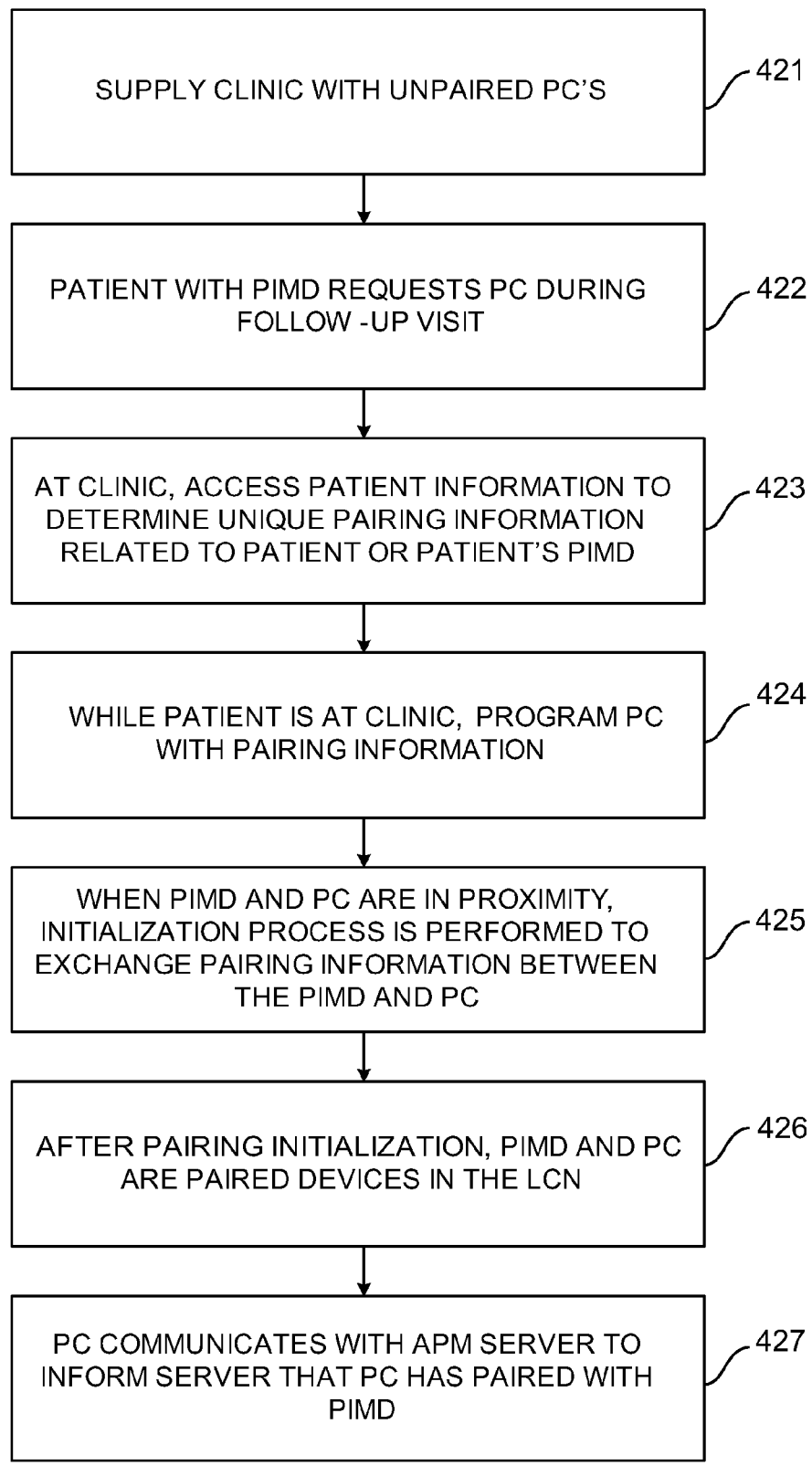

In one exemplary process, illustrated by the flow diagram of FIG. 4C, the medical facility has 421 on hand a supply of unpaired PPC's. Immediately following implantation or during a follow-up visit, the patient having a PIMD is provided with 422 an unpaired PPC. The ID of the PPC, the ID of the patient's PIMD, the ID of the patient, and/or other pairing information unique to the patient, the PIMD, and/or PPC is ascertained 423, such as by accessing the APM server where such information is stored. The ROM of the PPC is flashed 424 with the pairing information or the information is otherwise stored in the PPC memory.

When the pairing initialization mode of the PPC is activated and the PPC is in communication proximity with the PIMD, the PPC initiates 425 the pairing process. The pairing initialization process may involve providing the PIMD with the ID of the PPC, exchanging encryption keys, and/or providing or exchanging other information to form the PIMD-PPC pair.

In some implementations, the pairing initialization process may require that the PIMD also be placed in pairing mode, for example, through the use of a command issued by a device programmer which is in communication with the PIMD. During pairing mode, the PIMD is placed in a state wherein the PIMD is ready to accept communications from a PPC and/or to participate in an exchange of pairing information with the PPC to form a PIMD-PPC pair.

After the pairing initialization process is performed, the PIMD and the PPC are 426 paired devices on the LCN. The PPC may communicate 427 with the APM server to report that the pairing was successful. In the event that pairing could not be completed, the PPC would report an unsuccessful pairing attempt.

Figure 4D:
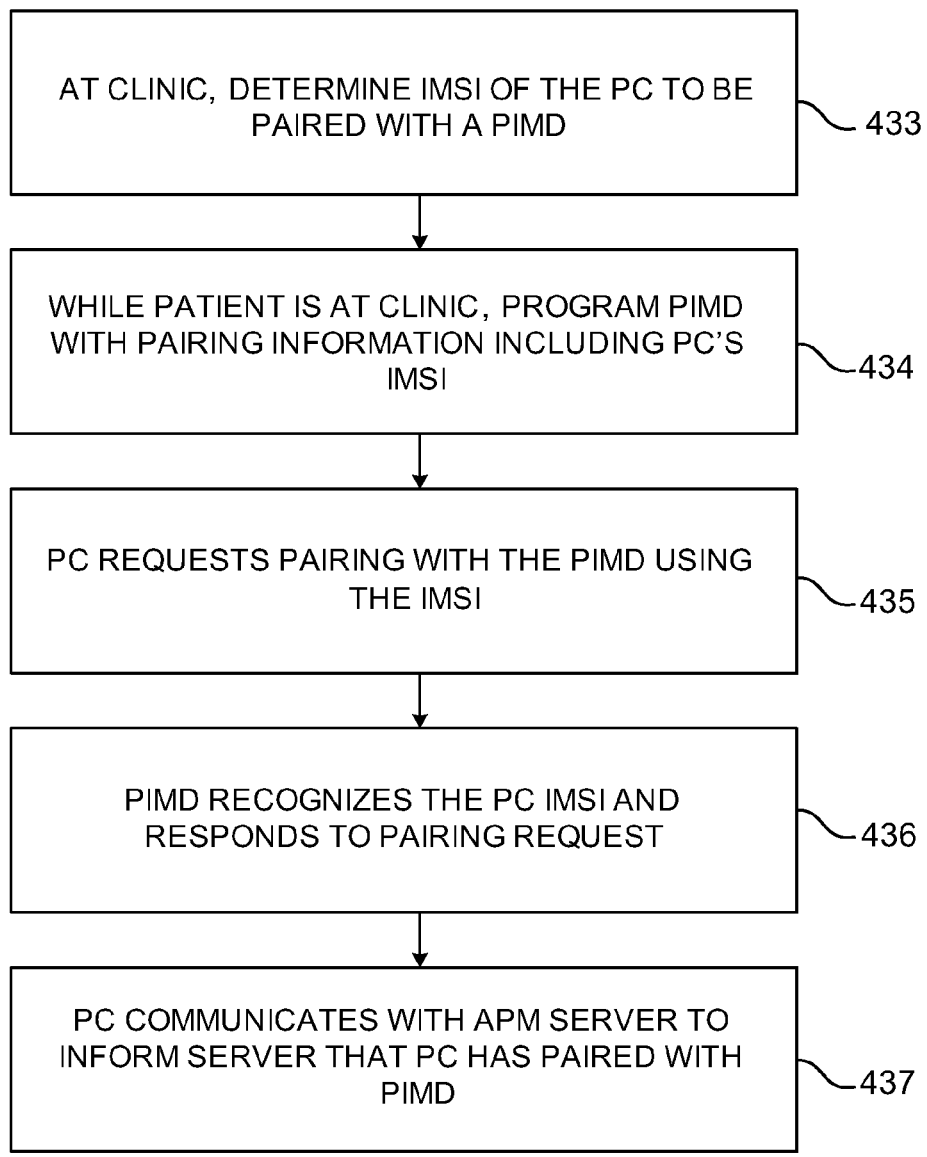

In a similar implementation, illustrated in FIG. 4D, unpaired PPC's can be paired with patient's PIMD by storing pairing information in the PIMD at the hospital or clinic, for example. The ID of the PPC, which may be the international mobile subscriber identity (IMSI) of the PPC's subscriber interface module (SIM), and/or other pairing information is determined 433. The pairing information can be programmed 434 into the PIMD via a device programmer. After programming the PIMD with the pairing information, the pairing initialization process involves a request 435 for pairing by the PPC directed to the PIMD. The PIMD recognizes 436 the ID of the PPC, allowing pairing to proceed. After pairing, the PPC notifies 437 the APM server that the pairing is complete.

The use of the SIM ID of the PPC for pairing allows pairing to be maintained even if the patient receives a new PPC. The SIM card from the old PPC can be moved to the new PPC and, through the SIM ID, the new PPC remains paired to the patient's PIMD.

Figure 4E:
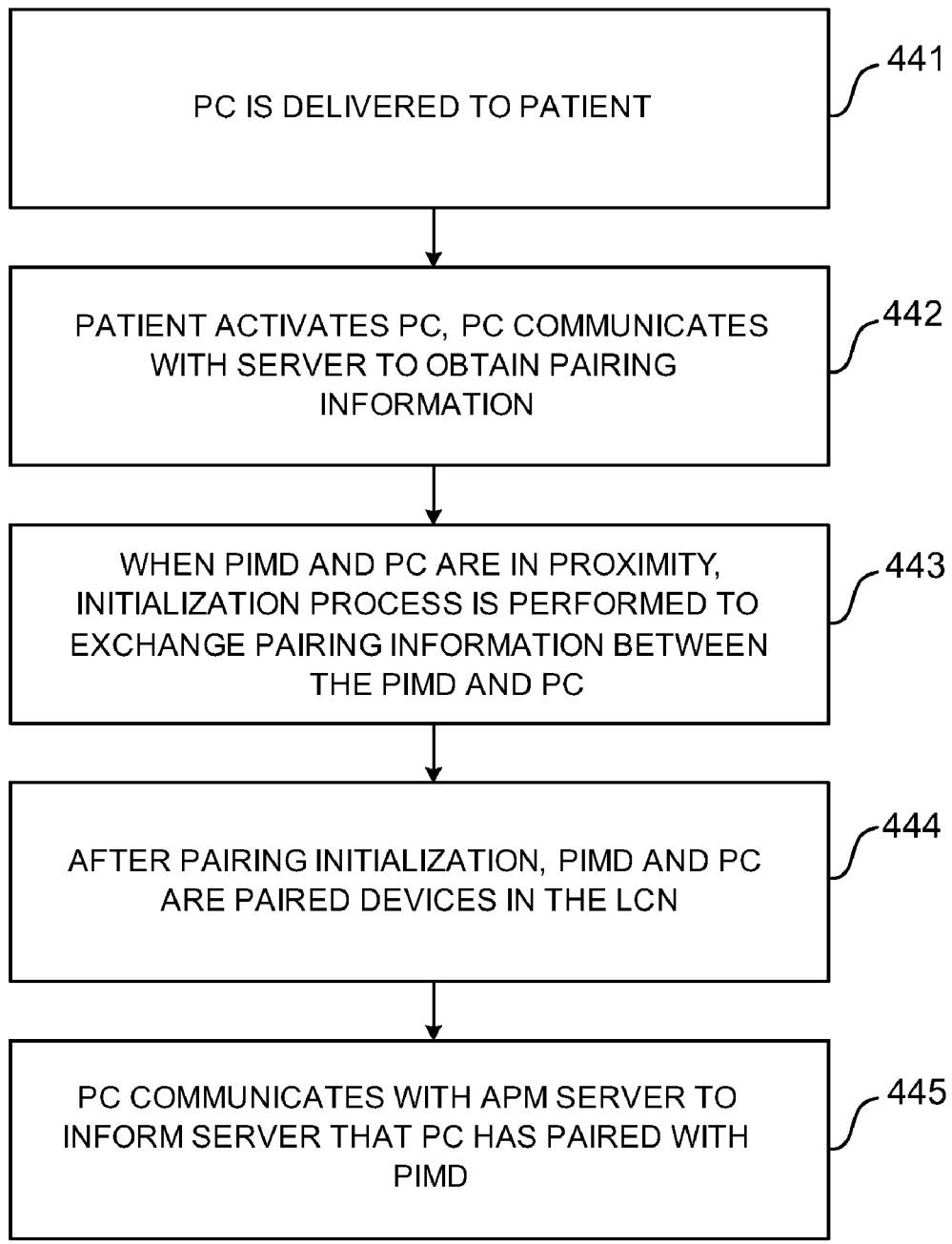

In some implementations, pairing information may be acquired by the PPC from the APM server before pairing begins. This pairing technique, which is illustrated in the flow diagram of FIG. 4E, allows for clinic- or home-based pairing. An unpaired PPC is delivered 441 to the patient's home or to the clinic. Pairing between the PIMD and the PPC may be initiated 442 by the patient or medical professional. In one scenario, pairing may be initiated by activating the PPC and/or by pressing a button on the PPC which causes the PPC to establish 442 communication with the APM server for the purpose of downloading pairing information. Alternatively, the patient may call the APM medical service center when ready to begin pairing. The server then is made to establish communication with the PPC and push the pairing information to the PPC. After receiving the pairing information, when the PPC is in communication proximity with the PIMD, the PPC initiates communication 443 with the PIMD and transmits the pairing information. If the pairing initialization process is successful, the PIMD and the PPC are paired devices 444 on the LCN. The PPC reports back 445 to the server regarding the success or failure of the pairing initialization.

The pairing scenarios illustrated in FIGS. 4C and 4D include involvement of the APM server, programmer, and/or other device communicating with the PPC and/or PIMD to assist in providing pairing information to the PPC or PIMD. It is desirable in some situations for the PPC and PIMD to be capable of autonomous pairing without involvement from an external device. Autonomous pairing is particularly useful because the PPC can be shipped directly to the patient. Autonomous pairing also allows for re-pairing between the PPC and the PIMD. Re-pairing may be performed if either of the devices lose pairing information after the initial pairing which makes a subsequent pairing operation necessary to reinstate communication between the PPC and the PIMD.

Figure 4F:
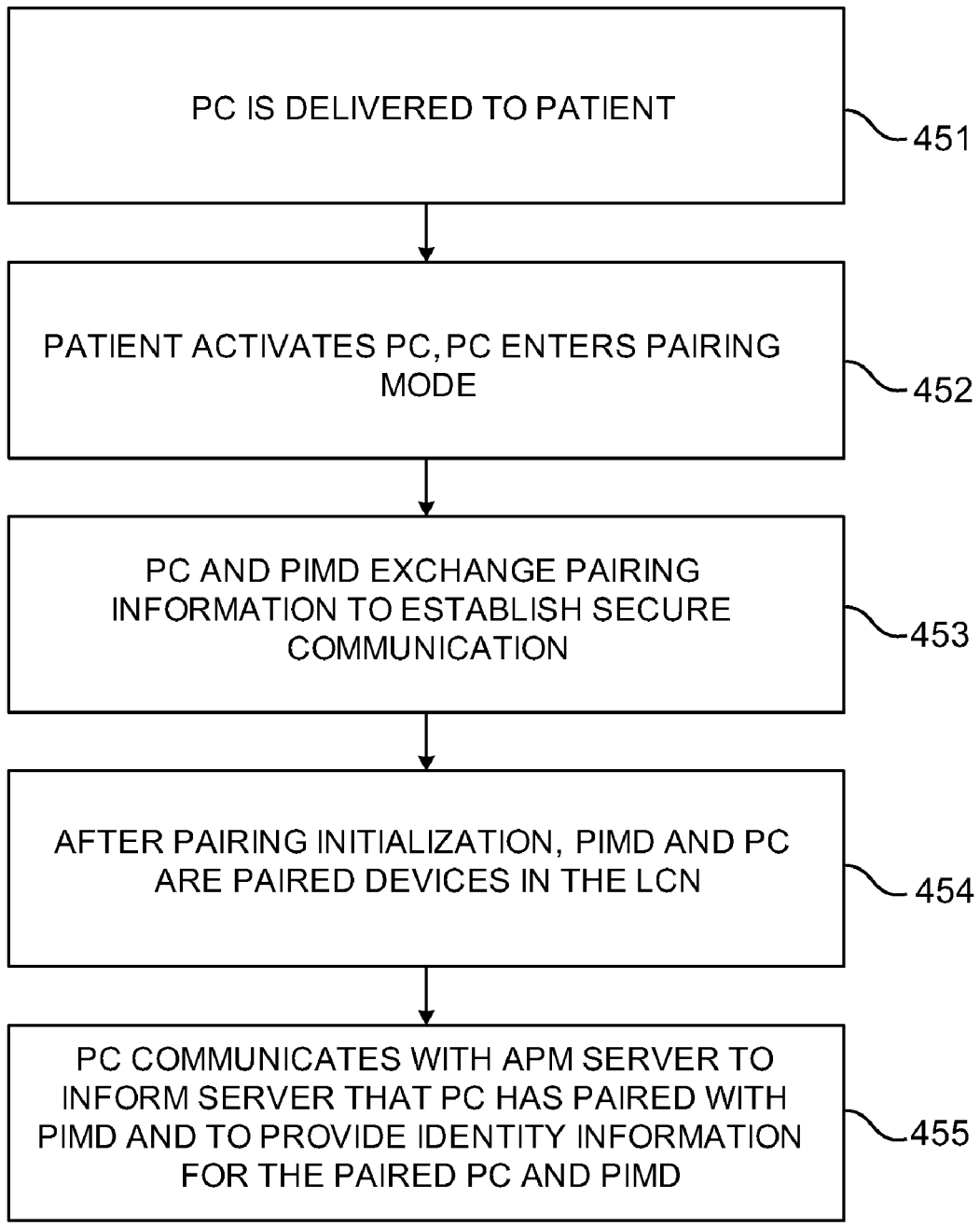

FIG. 4F is a flow diagram illustrating an autonomous pairing process between a PIMD and PPC. In this implementation, the patient receives 451 the PPC. The patient activates the PPC and the PPC enters 452 pairing mode. For example, the patient may push a button that causes the PPC to enter pairing mode. In one implementation, the PPC initiates communication with the PIMD and the PPC and PIMD exchange 453 pairing information. In some implementations, the PPC is equipped with a radio frequency identification (RFID) interrogator and the PPC reads an RFID tag in the PIMD to identify the PIMD and/or leads or other implanted hardware/sensors.

After pairing, the PIMD-PPC are 454 paired devices in the LCN. The PPC informs 455 the server that the PIMD-PPC pairing has occurred and informs the server of the specifics of the pairing, e.g., the IDs of the paired devices.

In autonomous pairing situations where there may be more than one PIMD in range of the unpaired PPC attempting to initiate pairing, it is advantageous to ensure that the unpaired PPC is pairing with the proper PIMD. Improper pairing or improper re-pairing may be avoided, for example, by acquiring physiological data from the patient via sensors on the PPC and comparing the physiological data acquired by the PPC to sensed physiological data acquired by the PIMD that is implanted in the patient.

Figure 5A:
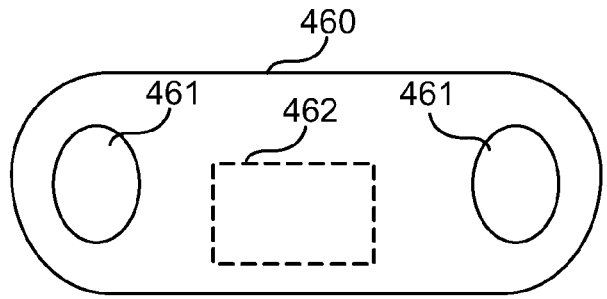
FIG. 5A shows an embodiment of a PPC equipped with one or more sensors configured to sense a physiological parameter of the patient in accordance with embodiments of the present invention.

In one exemplary embodiment, shown in FIG. 5A, the PPC 460 is equipped with one or more sensors 461 configured to sense a physiological parameter of the patient. For example, the sensors 461 may include metallic sensors for skin contact with the patient through which the patient's heartbeat is acquired. The sensors are coupled to electronics (e.g., amplifies, filters, signal processors, and/or other circuitry) that provides a heartbeat signal detector 462 within the PPC.

Figure 5B:
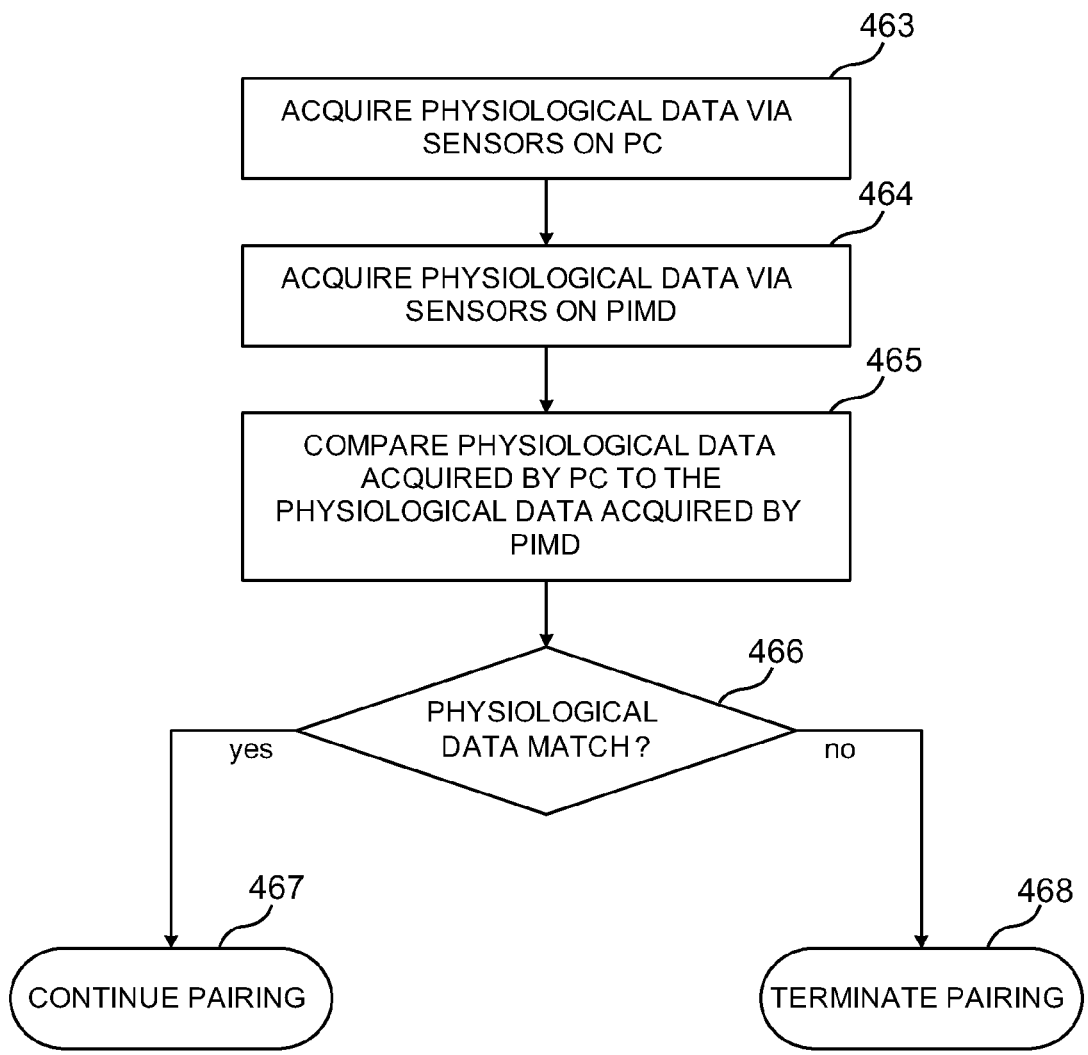
FIG. 5B is a flow diagram illustrating acquisition of physiological data for a particular parameter using sensors and/or circuitry on or in the housing of a PPC in accordance with embodiments of the present invention.

As illustrated the flow diagram of FIG. 5B, physiological data for a particular parameter (e.g., patient's heartbeat signal) is acquired 463 by sensors and/or circuitry on or in the housing of the PPC. Physiological data for the same parameter is also acquired 464 by the PIMD. The physiological data acquired by the PPC is compared 465 to that acquired by the PIMD. For example, the signal morphology, heart rate, or other characteristics extracted from the heartbeat signals acquired by the PPC and the PIMD, respectively, may be compared to check for a match. If the physiological data acquired by the PPC is consistent 466 with the physiological data acquired by the PIMD, then the pairing is proper and continues 467. If the physiological data acquired by the PPC is inconsistent 466 with the physiological data acquired by the PIMD, the PPC is most likely attempting to pair with a PIMD other than the PIMD implanted in the patient. In this situation, the pairing is improper and is terminated 468.

The PPC may be equipped with sensors for sensing any type of physiological data that can be verified by the PIMD to confirm proper pairing. For example, the PPC may include the metallic sensors for skin contact as described above and/or may include a microphone for detecting respiration sounds and/or heart sounds which may be detected if the PPC is held near the body. The PPC may alternatively or additionally include a posture sensor, motion sensor, pulse oximeter, and/or other suitable sensors that may be used to verify proper pairing through comparison of information acquired by the PPC sensors with information acquired using corresponding sensors of the PIMD. In one configuration, to verify proper pairing, the PIMD may pace at a specified rate, such as 65 ppm, during a pairing verification process. The PPC detects the heart beat, for example, by skin contact via metallic contacts on the PPC, and/or by inductively sensing the electric field generated by the pacing pulses without metal-skin contact. If the heart beat or pacing pulses occur at the specified rate, proper pairing is verified.

In one implementation, the PIMD is equipped with a light detector and the PPC includes a light source. By holding the PPC outside the patient's body but oriented with respect to the PIMD so that light emitted by the PPC can be detected through the patient's skin by the PIMD, the PPC can send an optical signal to the PIMD to verify proper pairing.

The pairing process outlined by FIG. 5B is particularly useful in autonomous pairing or re-pairing the PPC and the PIMD. As previously discussed, re-pairing may become necessary if the pairing information of either device is lost, for example, in the event that the either the PPC or PIMD have memory loss which may result from a software reset or battery depletion.

A variety of pairing scenarios are made possible by the portability and mobile connectivity features of a PPC implemented in accordance with the present invention.

Pairing between a PPC and a PIMD may be performed at different locales, each of which may implicate different levels of pairing functionality. For example, pairing that occurs at a the hospital or a physician's clinic may implicate a full range of pairing features, while pairing that occurs at the patient's home may implicate a reduced range of pairing features.

Pairing between a PPC and a PIMD may be performed wirelessly between an APM server and a PPC. The APM server can initiate the pairing operation, and authentication can be performed during initiation of the pairing, which may involve use of a pseudo certificate or other form of robust authentication that is preferably based on more that the serial number of the PIMD. A wireless pairing approach enables relatively fast paring of a PPC to its associated PIMD. A wireless pairing process provides the opportunity to have ongoing data transfer during the pairing operation.

A number of different wireless pairing scenarios are contemplated. According to one scenario, a "generic" PPC is delivered to the patient's home. This "generic" PPC can represent an off-the-shelf PPC that has not been configured or programmed for operation with a particular PIMD. Instead, configuring the PPC for use with a particular patient's PIMD occurs at the end destination (e.g., at the patient's home or a neighborhood clinic/physician's office). This scenario significantly reduces the complexity and cost of pre-configuring each PPC for use with a particular PIMD at the medical device manufacturer facility and meticulously tracking each pre-paired PPC through the delivery chain to ensure the correct PPC is delivered to the correct patient.

A pairing scenario that employs "generic" rather than preset or pre-configured PPCs typically requires a greater level of authentication to ensure an accurate and safe pairing of the "generic" PPC with a given patient's PIMD. A more robust authentication process may employ use of real-time data exchange (e.g., using private/public certificates) between the PPC and PIMD. PIMD data and SIM card data may be used as part of the initial pairing and subsequently used for authentication when the PPC connects with an APM server over the LCN. Cellular keys, encryption, and other security technology provided by the cellular network provider may also be used to provide for enhanced security.

The International Mobile Equipment Identity or IMEI may also be used to enhance authentication robustness. The IMEI is a number unique to every GSM and UMTS mobile device. It is usually found printed on the device itself, typically underneath the battery. The IMEI number is used by the network to identify valid devices and therefore can be used to stop a stolen or lost device from accessing the network. The IMEI is only used to identify the device, and has no permanent or semi-permanent relation to the subscriber. Each PPC may have an IMEI that can be used to help identify the patient who receives a particular PPC, and may be of particular use during the first pairing operation (or initial pairing for a particular patient in the case of a re-allocated PPC).

An advantage to using a SIM card in the PPC is that the SIM card can store an authentication key itself (e.g., unique information about PIMD stored in the SIM card after the first pairing). After the first pairing, the SIM card can be moved (swapped) from one PPC to another PPC (e.g., a new PPC or a "borrowed" PPC) by the patient, clinician or technician. This approach advantageously allows PPCs to retain their "generic" configurable character. According to one approach, the APM server may be used to manage inventories of SIM cards that are in use. Proper management of SIM cards allows for reuse or re-pooling of SIM cards and numbers. For example, a patient may want to keep a particular PPC that needs to be re-initialized with a new SIM card or SIM number. Re-initialization may be performed by the APM server.

Another pairing scenario involves two or more patients in the same home that have PPCs or receive PPCs around the same time. During initial pairing within a multiple-PPC environment, it may be beneficial to use patient-unique information to ensure that a given PPC is paired with the correct patient. In one approach, a physiologic signature unique to the patient may be sensed by a sensor on the PPC's housing, such as a heart rate sensor. An indicator on the PPC may indicate whether or not the correct PPC is paired with the correct patient. In another approach, it may be advantageous to permit two patient PIMDs to use either of the patient's PPCs. In this situation, a PPC may be paired with more than one PIMD.

In-clinic pairing may allow for enhanced features and functionality. Pairing a PPC with a patient's PIMD in a clinic allows for efficient input of needed PIMD, PPC, and patient data into the APM server. When creating or updating patient data stored in the APM server, identity and other information about a new or re-used PPC (e.g. model number, serial number, SIM card information IMEI number, etc.) can be entered into the APM system interface. Since data entry occurs at the clinic and is recognized as such by the APM system, security protocols need not be as stringent as in the case of non-clinic or public scenarios. If PIMD and PPC pairing involves a magnet mode, then the data can be synchronized after use of the magnet.

A unique web based PPC interface for use in the clinic or physician's office may be presented to the clinician to facilitate in-clinic programming and reprogramming of the PPC. The clinic or physician's office may be equipped with a "super" access point web facility that can eliminate the need for an in-office programmer(s). An interlock feature may be used to enable a class of commands that allows programming of the PPC based on the in-office PPC communicating with the in-clinic web laptop or computer. The PPC may pass an optical code or other security identifier to the in-clinic web laptop as a security lock. The clinic may pass an inductive or RF device in proximity to the PPC in the clinic that ensures that the PPC is, in fact, at the clinic. This may also provide a basis for indicating patient consent to make the programming changes. The physician may enter a certificate as a surrogate to make programming changes.

In one approach, signal strength between the PPC and the clinic's Wi-Fi or wireless access device (which will be high within the clinic) may be used to confirm that the PPC is indeed at the clinic during the initialization or updating procedure. The PIMD may be programmed to generate an audible or ultrasonic tone that can be detected to indicate PIMD pairing with a new PPC. A microphone on the PPC may be used to pick up an audible tone or, in an alternative approach, pick up the patient's heart rate, in which case there is no need for a PIMD generated tone.

In another scenario, it may be irrelevant which PPC is paired with which PIMD. In this scenario, all PIMD data is identified by PIMD serial number and perhaps other information so that, no matter which PPC is used, the PIMD data that is received at the APM server is properly associated with the correct patient. This "soft pairing" approach can significantly reduce the complexities of "hard" PPC pairing approaches. It is noted that the PPC through which a PIMD communicates with the APM server will still have to be properly authenticated and authorized for connection with the APM server.

Hard PPC pairing has several advantages over soft pairing. Because hard pairing involves pairing of a specific PPC with a specific PIMD, repeated or duplicative transfers of the same data from the PIMD to the PPC and from the PPC to the APM server can be avoided. PIMD power can be conserved by eliminating redundant wake-up and connection operations between the PIMD and a multiplicity of different PPCs which can occur when using soft pairing. Moreover, precious PIMD power can be conserved by eliminating duplicative signaling and data transfers between the PIMD and the PPCs. One approach to conserving PIMD power when a soft pairing approach is used involves limiting the number of signaling and data transfer event between the PIMD and the PPCs, with the exception of high priority/criticality events.

Lost or Inadvertently Exchanged PPC

Over the course of time, the patient may lose or temporarily misplace the PPC. In situations where PIMD-PPC patients live nearby or interact with other patients having PIMD-PPCs, the PPCs, which may look very similar, can be inadvertently exchanged between the patients. If the patient's PPC is misplaced, forgotten or inadvertently exchanged, this may result in loss of periodic updates from the PPC, event driven updates and/or may preclude life critical PPC alerts to the APM server if the patient experiences a significant cardiac or physiological event.

Various safeguards may be incorporated in the PPC to avoid or prevent loss or inadvertent exchange of the PPC. For example the PPC, the PIMD, or both, may include processes or mechanisms that to detect if the PIMD and PPC are out of range and to alert the patient. The possible patient alert mechanisms may include a vibratory alert, a visual alert, and/or an audible alert.

The PPC may include a proximity detector that determines if the PPC is sufficiently close to the PIMD to maintain communication between the devices. If the PPC detects that the PIMD is out of communication range, the PPC and/or PIMD may send an alert to the patient. For example, the PPC may be equipped with a beeper that is activated if the PIMD is out of range of the PPC. In another example, if the PIMD has not communicated with the PPC for predetermined time interval, the PIMD may vibrate to notify the patient. In yet another example, the PPC may send a message, such as an SMS message, to the patient's cell phone and/or may notify the APM server if the PIMD and PPC have been out of range and/or have not communicated for a period of time. The manner and extent of alerting the patient that the PPC is out of range of the PIMD generally depends on the patient and his or her condition. For example, the PPC of a typically bradycardia patient may need to communicate infrequently with the APM server. In this case, proximity alerts may be more subtle and infrequent. For a patient having severe heart failure, this patient may need to communicate frequently with the APM server, in which case proximity alerts may be more conspicuous and frequent.

The PIMD may be equipped with a beeper and/or vibrator and the PPC may be equipped with a light, beeper and/or vibrator, or other type of alert. One or more of the alert mechanisms may be activated if the PIMD is out of range of the PPC or if the PIMD and PPC are not in communication. The alert may be based on a time limit trigger, i.e., the alert is generated after the PPC and PIMD are out of communication range for more than a predetermined period of time. Any combination of stimuli perceptible by the patient that can be generated by the PPC and/or PIMD may be used to notify the patient of the out or range or loss of communication condition. Such perceptible stimuli may be coupled with messaging to the patient's cell phone, pager, or to the APM server by the PPC to indicate the out of range or loss of communication condition.

The PPC may include a global positioning system (GPS) functionality and, in the event the PPC is lost, the last known GPS address of the PPC may be used to find the lost PPC. Alternatively, if the PPC is still energized, the general location of a lost PPC may be located via pings from the base station.

The PPC and the PPC docking station or hub may cooperate to provide a locator feature. For example, to locate a lost PPC, the patient may push a locator button on the docking station which causes the PPC to emit a combination of light, tones, or vibration to assist the patient in locating a lost PPC.

Patient/System Interactions

As illustrated in FIG. 4A, the PPC is coupled through an RF telemetry link to a PIMD and is coupled through a mobile communication network, such as a mobile cellular network, to the APM server. The mobile cellular connectivity of the PPC provides for a variety of interactions between the patient and the APM system, between the patient and the PIMD-PPC pair, and/or between the patient or PIMD-PPC pair and other services accessible via the mobile cellular network.

Exemplary services that may be provided through use of the PIMD-PPC pair, involve medication management for the patient, medication schedule compliance tracking, exercise schedule compliance tracking, and/or periodic physiological test compliance tracking, compliance tracking of prescribed external therapies (e.g., patient use of CPAP or oxygen therapies), prescription refills, and/or information relayed to the patient's physician, patient advocate or APM server if patient activity, exercise or physiological tests indicate a change that needs attention.

The PPC and/or server may generate reminders to the patient to perform some action, such as take medication, perform a home-based diagnostic test, exercise, or use an external therapy device, e.g., CPAP device. The patient reminders may be based on a particular time schedule that is programmed into the PPC, for example, via website or SMS messaging. In some embodiments, the reminders may not correspond to a schedule but are event-driven based on the physiological condition of the patient.

In one configuration, the reminders may be conveyed to the patient via the PPC by a flashing light or vibration. The patient may know from observing the flashing light or vibration that it is time to take some action, such as take medication or perform a home-based physiological test. More sophisticated communication with the patient may be accomplished by using the flashing light or vibration to notify the patient to check a website where additional information can be displayed. In one approach, a laptop, PDA, cell phone or iPod, for example, can provide an extended interface for the PPC that can be used to identify drugs (by picture) and instruct the patient when to take the drugs.

Unless the patient has mobile internet service, when an active patient is away from home or office, accessing a website may not be possible immediately or within a short time after receiving a flashing light or other indicator from the PPC. If the PPC does not have a keypad or display, the user interface of the patient's cell phone may be used to facilitate interaction between the patient and the PPC. The display of the patient's cell phone can be used to display additional information from the PPC while the patient is mobile and cannot access an internet-connected computer. Communication between the PPC and the patient may be accomplished, for example, via SMS messaging between the patient's cell phone and the PPC.

For example, while the patient is out and about, he or she may receive an SMS message on her cell phone that it is time to take one or more medications. The patient may respond via SMS message to the PPC or server after taking the meds, allowing the PPC or server to track the patient's medication schedule compliance and the patient's medication inventory.

The PPC or server may be programmed to remind the patient to refill medications or may automatically contact the patient's pharmacy to request a refill when the patient's inventory of medication is low. For example, the PPC may provide a perceptible stimulus (light, sound or vibration of the PPC) or the PPC or server may send an SMS message or email to the patient reminding the patient to refill medications. In another example, the PPC or server may send an SMS message or email to the patient's pharmacy indicating that a refill is needed. Telephone numbers and/or email addresses for the patient, the patient's advocate, physician, pharmacy and/or other services may be programmed into the PPC via cellphone or website. The patient may initiate a call to the patient's pharmacy or other services by pressing a button on the PPC.

In some situations, it may be beneficial for reminders and/or other messages to be communicated to the patient by voice message. The PPC may include a speaker so that voice messaging can be used. For example, the patient's physician or advocate may record a voice message directed to the PPC. The patient, upon observing a flashing light or other indicator on the PPC, presses a button that causes the voice message to be delivered via the PPC speaker and listens to the voice message from the physician or patient advocate. Alternatively, the flashing light or other perceptible stimulus may serve as an indicator that a web site should be accessed to retrieve the voice message or text message. In another configuration, the voice message may be sent to the patient's cell phone or land line voice mail box.

Figure 6:
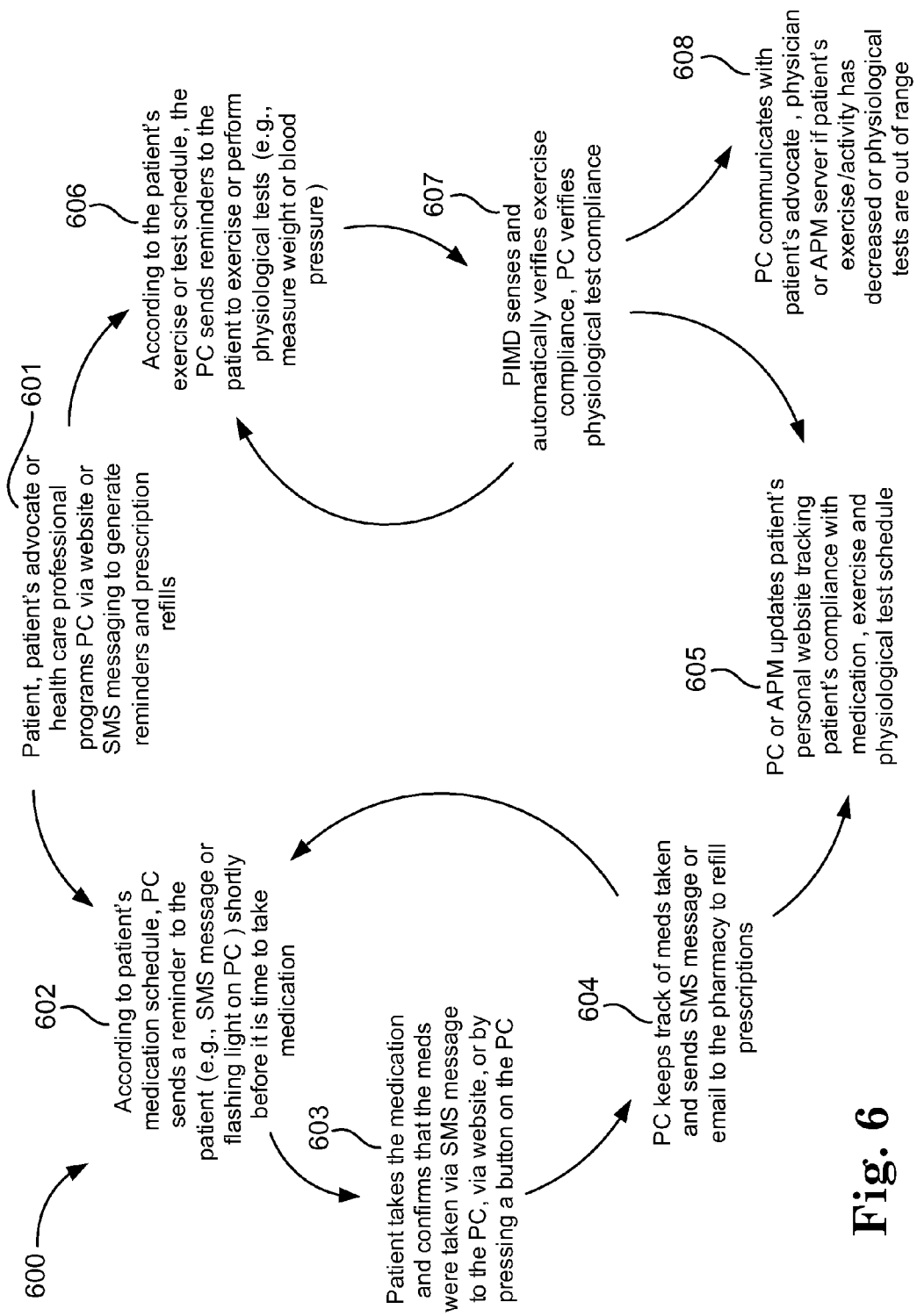
FIG. 6 is a flow diagram illustrating an exemplary set of interactions that may occur between the patient and the PPC, the APM server, and other services accessible via the PPC in accordance with embodiments of the present invention.

FIG. 6 is a flow diagram illustrating an exemplary set of interactions that may occur between the patient and the PPC, the APM server, and other services accessible via the PPC. The patient, the patient's advocate, or health care professional programs 601 the PPC via a website or SMS messaging to generate reminders for the patient, track patient compliance, and initiate prescription refills. In accordance with the patient's medication schedule, the PPC sends 602 reminders to the patient, e.g., via SMS message delivered to the patient's cell phone, or by a perceptible stimulus generated by the PPC shortly before the scheduled time for the patient to take medication.

The patient takes the medication and confirms 603 that the meds were taken, e.g., via SMS messaging from the patient's cell phone to the PPC, by pressing a button on the PPC, or via interaction with a website. The PPC keeps track 604 of the patient's medication schedule compliance and/or the patient's medication inventory. The PPC may be programmed to send an SMS message or email to the patient's pharmacy to order prescription refills. The PPC or APM updates 605 the patient's personal website that tracks the patient's compliance with the medication schedule.

The PPC may also be used to help the patient comply with an exercise schedule or to perform scheduled physiological tests such as weight and/or blood pressure tests. According to the patient's exercise and/or test schedule, the PPC sends 606 reminders to the patient shortly before the scheduled time to exercise or perform the test. The PIMD senses 607 the patient exercise and verifies exercise schedule compliance. The output from physiological testing equipment, such as a weight scale and/or blood pressure cuff, may be coupled to the PPC directly or through another device such as the PPC docking station, for example. When the patient performs the scheduled physiological tests, the PPC verifies compliance with the physiological test schedule. The PPC or APM server updates 605 the patient's personal website that tracks the patient's compliance with the exercise or physiological testing schedule. The PPC may message the patient's advocate or physician if the patient's exercise/activity has decreased significantly, or if the patient's physiological tests are out of range.

The physician may require the patient to assume various positions for certain diagnostics. In one approach, the physician talks to the patient over the phone, and real-time EGM and other data is streamed to the APM server via the PPC for presentation on the APM server web site. In this manner, the physician can collect the desired data for each necessary patient position. Alternatively, positioning instructions can be communicated to the patient via the APM server web site or broadcast to the patient over a speaker provided on the PPC. The patient follows the instructions, and data is collected by the PPC. This data can be communicated in real-time or at a later time (e.g., during off-peak times).

PPC Employing External Noise Detection

According to some embodiments, the PPC may be equipped with circuitry to sense magnetic and/or electromagnetic leaks or fields as noise that can potentially interfere with PIMD operation (e.g., falsely sensing an externally generated e-field or b-field as a tachycardia event and attempting to treat the falsely detected event). For example, detectors used in stores for detecting active merchandise sensors for theft control may undesirably interfere with PIMD operation. The PPC can be configured to sense such externally generated fields and, when detected, transmit a signal to the PIMD indicating that a shock or other cardiac electrical therapy is not to be delivered because of the "noise" detected by the PIMD.

In another approach involving the APM system 850, and with reference again to FIG. 9A for example, the "noise" data sensed by the PPC 800 and the PIMD data may be uploaded or streamed to the APM server 850, and the APM server 850 can assess these data and determine whether any PIMD action is required. The PPC 800 may provide a visual, audio, or tactile indication to the patient that the patient has entered a "bad area" in which extraneous and problematic noise has been detected. The indicator may continuously alert the patient with the "bad area" warning until the patient has left the "bad area," which results in termination of the warning. As was discussed previously, a dashboard application may allow an authorized user to command the PPC 800 to effect a scan of the PPC's local environment for RF interference. Data acquired from this scan can be shown on an "interference" indicator of the dashboard.

Various medical diagnostic procedures may require that the PIMD 802 switch to a "safe mode" of operation, which typically involves continuance of basic necessary functions and temporary discontinuance of extra features. For example, a patient with a pacemaker or ICD may require an MRI or other procedure that can adversely interfere with PIMD operation. The PPC 800 may send a command signal to the PIMD 802 to switch to a safe mode, such as a magnet mode of operation, for the duration of the diagnostic procedure, during which temporary settings are typically used by the PIMD 802. For example, the PPC 800 may be enabled by the APM server 850 to command the PIMD 802 to switch to the safe mode. After completion of the diagnostic procedure, the PPC 800 may transmit a command to cause the PIMD 802 to switch to a normal operating mode. Transmission of this command from the PPC 800 to the PIMD 802 may be instigated by communication of a command from the APM server 850 to the PPC 800. As a fail-safe, a timer that is set to expire well after completion of a typical diagnostic procedure (e.g., 2-4 hours) may be used to ensure that the PIMD 800 switches back to a normal operating mode.

Patient Incentives to Use the PPC

Some patients having a PIMD may be relatively mobile and healthy, leading them to be less cognizant of the need to carry the PPC to allow for periodic or event-driven communication to the APM server. For these patients, it may be desirable to provide various incentives to encourage them to keep the PPC charged and/or to carry the PPC with them as they go about their daily activities. The PPC may be made more attractive to the patient by making "skins" for the PPC case available, allowing the patient to personalize the PPC in accordance with a particular interest or aesthetic taste. The PPC skins may additionally serve as a mechanism to identify the PPC as the patient's device, avoiding inadvertent exchange of the patient's PPC with the PPC of another patient.

The form factor of the PPC allows the PPC to be carried easily carried, and may include a clip, a lanyard, or other attachment mechanism. The PPC may be configured to clip or otherwise attach to an object that the patient always or usually carries, such as the patient's cell phone, watch, or other object.

The PPC may include functional features that provide incentives for the patient to carry the PPC. As described herein, the PPC may generate reminders to the patient in accordance with the patient's medication schedule, exercise schedule, or physiological testing schedule. If the patient finds these reminders to be useful, the feature may incentivize the patient to carry the PPC.

Another example of enhanced PPC functionality providing patient incentives involves the use of the PPC as an exercise or activity monitor. Many people are interested to know how many calories they burn as they exercise or go about their normal daily routine. The PPC may provide this type of feedback to the patient, thereby producing an incentive to the patient to keep the PPC charged and carry the PPC during day-to-day activities. For example, accelerometer data acquired by the PIMD and relayed to the PPC may be converted to calories, metabolic equivalents (METS) or other convenient units that the patient can use to track their activity level. Additionally, a pedometer may be provided on the PPC itself to measure the number of steps taken or miles walked or run during the day. The information can be communicated to the patient via website, or by SMS message from the PPC.

Remote Programming

The ability of the PIMD-PPC pair to provide event-driven updates, real-time waveform viewing and nearly instantaneous command access to the PIMD for modifying device parameters facilitates remote testing and remote PIMD programming through the LCN. Although remote PIMD testing and programming for various therapy parameters can be envisioned, remotely commanded capture threshold testing and remote programming for pacing energy are used as illustrative examples. Remote programming preferably involves a ping from the PPC to indicate to the PIMD that the PPC is close to patient's chest and ready to perform remote programming.

Figure 7A:
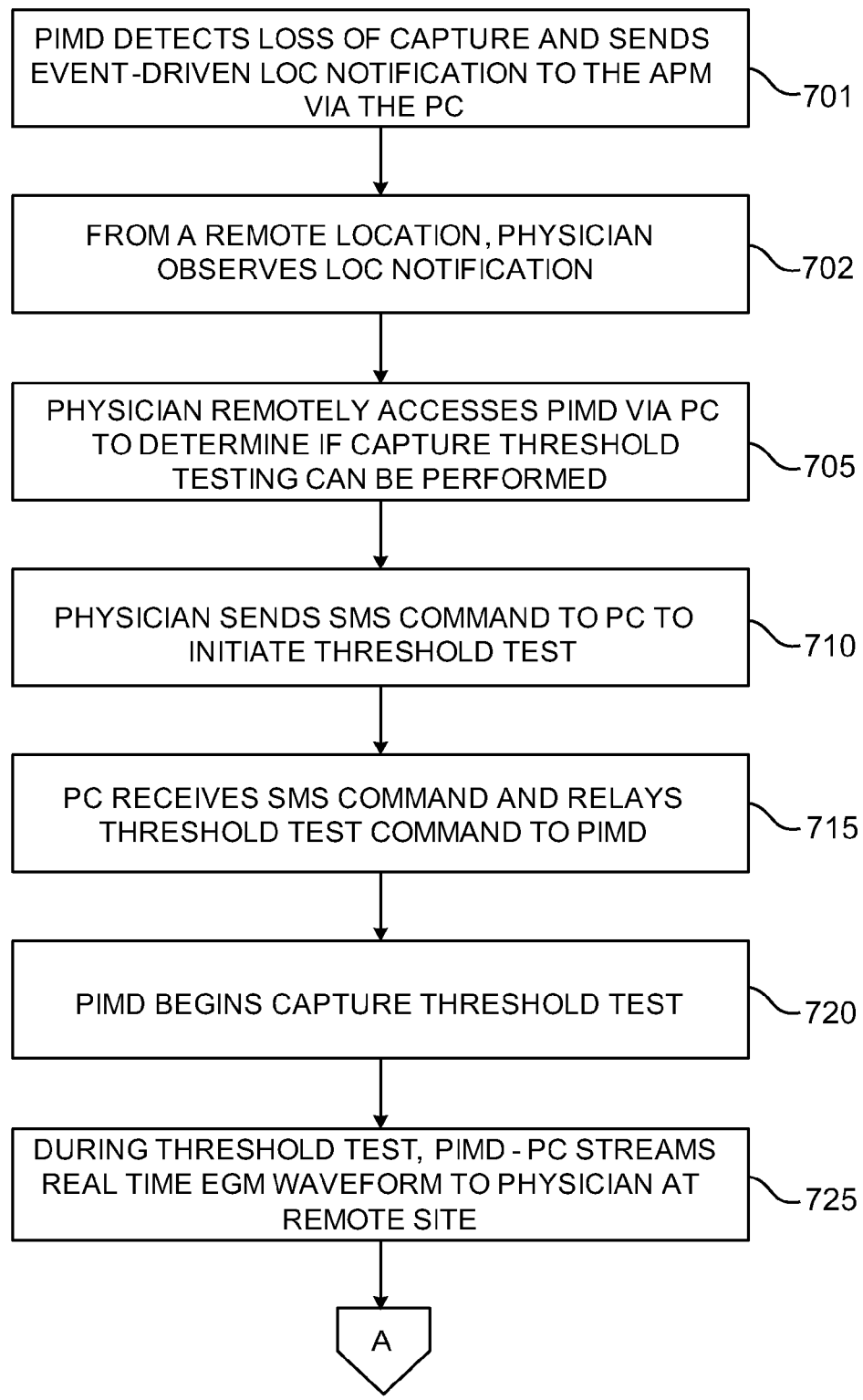
FIGS. 7A and 7B are process flow diagrams describing various processes for performing a remotely initiated and controlled capture threshold test using an APM server and a PPC in accordance with embodiments of the present invention.
Figure 7B:
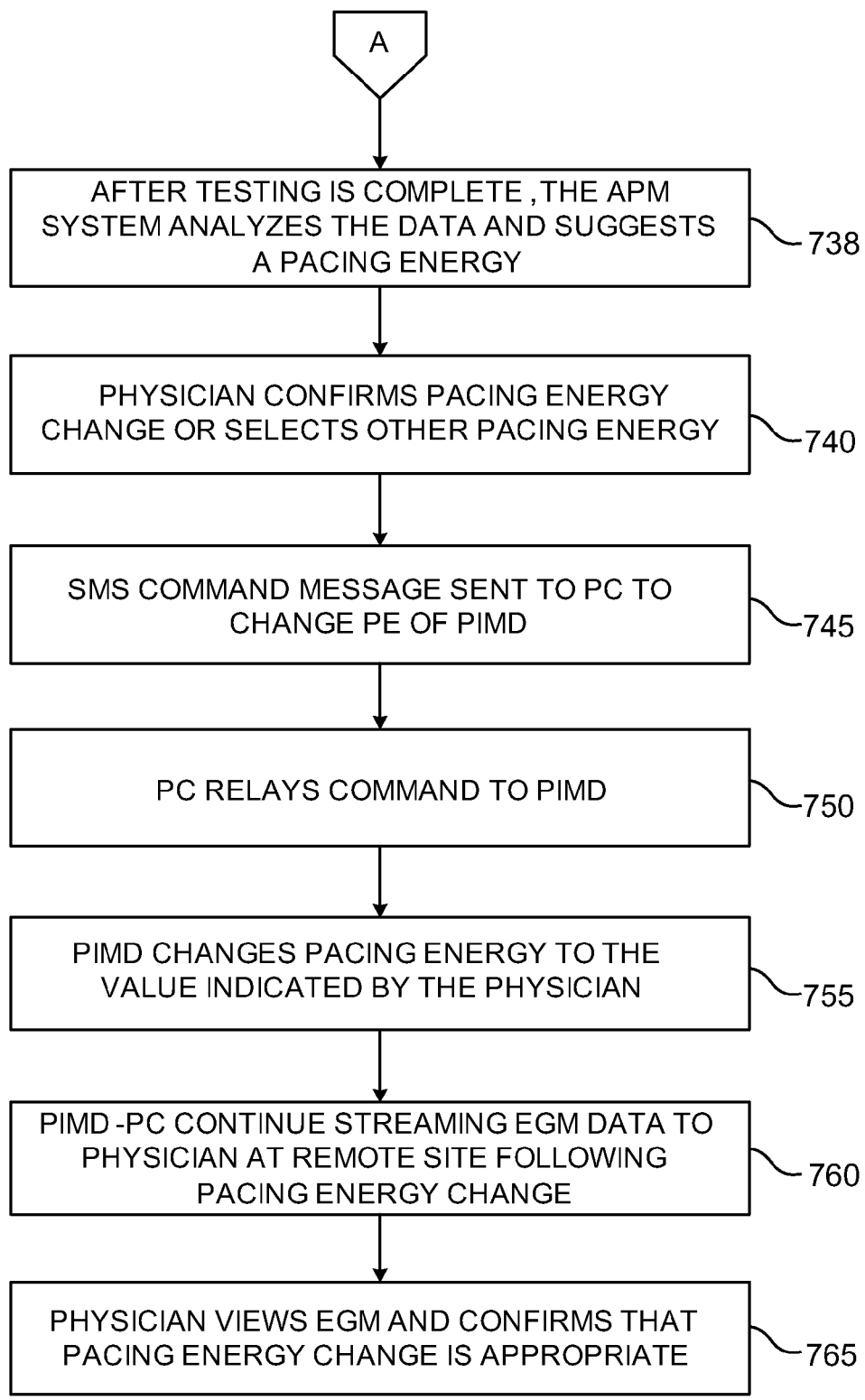

FIGS. 7A and 7B show a flow diagram illustrating remote capture threshold testing and pacing energy programming via the PIMD-PPC pair. The PIMD monitors paced cardiac cycles that do not produce capture and detects loss of capture (LOC) after a predetermined number of non-captured pacing cycles. The PIMD sends 701 an event-driven LOC notification to the APM server. The patient's physician observes 702 the LOC notification from a remote site. The physician remotely accesses 705 the PIMD via the PPC to determine if conditions are appropriate for performing a capture threshold test. If so, the physician sends 710 an SMS message command to the PPC initiating the capture threshold test. The PPC receives 715 the SMS message command and relays the command to the PIMD. The PIMD begins 720 the capture threshold test. During the threshold test, the PIMD-PPC pair streams 725 real-time EGM waveforms to the APM server and the physician observes the EGM waveforms from the remote site.

After threshold testing is complete, the APM system analyzes 738 the threshold test data from the PIMD and may suggest a pacing energy modification. The physician confirms 740 the pacing energy modification or selects another pacing energy. An SMS command is sent 745 to the PPC to change the pacing energy of the PIMD. The PPC relays 750 the pacing energy command to the PIMD. The PIMD changes 755 the pacing energy to the value indicated by the physician. If desired, the PIMD-PPC pair continue 760 streaming EGM data which is observable by the physician at the remote site. The physician observes 765 the streaming EGM data and confirms that the pacing energy change is appropriate for the patient. It is noted that these operations may involve real-time pinging from the PPC to the PIMD as a feedback mechanism, and may involve out of band signaling during the connection.

A precursor capability to remote programming that does not directly involve changing of PIMD pacing parameters or delivery of therapy is remote programming of PIMD diagnostics. For example, a number of PIMD alerts are typically programmed to provide diagnostics on leads, pulse generators, and arrhythmias, among others. When the PIMD detects a predetermined event, the occurrence of this event is recorded as an increment of binned events associated with a specific alert. When the number of binned events reaches a predetermined value, the alert is tripped. Attributes of the alerts (e.g., event detected, alert trip count, etc.) may be modified via remote programming. Other operations that can be effected by the physician that do not involve changing of PIMD pacing parameters or therapy delivery include resetting of diagnostic information, clearing faults, clearing buffers, and redoing detection.

Flexible alerts can be dynamically changed, and the number of alerts can grow as the patient's specific pathology is more thoroughly investigated and understood. By way of example, if the patient has atrial fibrillation (AF), then an initial set of alerts (e.g., 6 alerts) are made available for assessing the patient's AF condition. If a certain type of AF is detected, such as persistent AF, then additional alerts (9 alerts) can be programmed for the PPC that are targeted to enhance persistent AF detection and evaluation. Groups of alerts can be configured for each type of patient condition.

Delivery of inappropriate shocks to treat tachycardia is a significant concern for patients that have an implanted ICD. Remote programming of alerts associated with arrhythmia detection by the ICD may be performed by a physician via the PPC in order to better evaluate the patient's cardiac activity and the ICD's detection of same. Tailoring the alerts by use of PPC-enabled remote programming for a specific patient's ICD allows the physician the opportunity to more optimally program the ICD's arrhythmia detection criteria that directly impacts delivery of shocks to the patient's heart. This can result in a reduction in the number of unnecessary shocks delivered to the patient, which reduces patient distress and ICD power consumption. Although it is envisioned that the physician could modify the ICD's arrhythmia detection criteria remotely (i.e., technically feasible), it may be necessary to use a programmer at a clinic should induction testing be needed.

Another illustrative example of remote programming of a patient's ICD via the PPC involves physician commanded atrial shock therapy. A physician may view a patient's cardiac activity from a remote location via the APM server. The patient's PPC may, for example, stream real-time EGM data to the APM server. Alternatively, the patient can communicate to the physician (via a button push on the PPC or via a phone call) that an atrial shock is desired.

Should the physician determine that an atrial shock is appropriate, a command can be generated by the physician's laptop that instructs the APM server to transmit a command to the ICD via the PPC to initiate delivery of an atrial shock. The physician may view the patient's cardiac activity to determine if the therapy was successful in converting the atrial arrhythmia. Patient-initiated atrial shock therapy may also be enabled by providing an appropriate button on the PPC. It may be desirable to have the patient step through a sequence of button pushes or other steps to ensure that the patient does not mistakenly initiate delivery of an atrial shock therapy.

Cooperative communication between the APM server, PPC, and ICD can facilitate remote programming of a variety of ICD parameters. For example, remote programming can allow a physician to change ICD parameters that can improve or optimize shock therapy by modifying one or both of sensitivity and specificity parameters that influence the ICD's arrhythmia detection behavior. Changes to ICD parameters that may be effected by physician remote programming include increasing shock energy output, adjusting detection rate, modifying ATP parameters, and adjusting the number and range of detection zones, for example. The physician may remotely enable and disable detection enhancements, and may change parameters of such detection enhancements. In the case of a pacemaker or CRT device, the physician may adjust V-V timing, A-V interaction with ventricular pacing, and basic lower rate limit or upper rate limit parameters, among others.

Remote programming can involve providing the physician with options for changing parameters and perhaps providing recommendations for making changes, and then allow the physician to manually select parameter values. In general, the PPC has more data that the PIMD, and this additional data may be used by the PPC to make or recommend programming changes, similar to the way the PIMD automatically changes certain pacing and therapy parameters.

The additional information available to the PPC, such as from sensors and the APM server, can be used to optimize changes to pacing and therapy parameters. This additional programming intelligence provided by the PPC may be particularly useful in cases where the APM server can become overloaded. It can be appreciated, for example, that optimizing pacing parameters by the APM server for thousands of patients may be taxing or infeasible. Offloading some or all of the pacing parameter optimization burden onto the PPC can significantly reduce the traffic to and from the APM server.

Different workflows may dictate different manners of PPC-APM server interaction. When making a programming change to the PIMD, for example, a message can be sent to the PPC, the PPC can establish a "live" connection with the APM server, and the APM server can alter the PIMD programming. In a delayed workflow model, such as one involving quarterly reporting, the physician can take time to make a PIMD programming change. In another workflow involving an intermediary, such as a registered nurse, the RN may visit a nursing home on a quarterly basis, and be an intermediate between the APM server and a low-level clinician, such as one at a neighborhood clinic that does not require a physician.

Prior to, or during, remote programming, the physician may need to know what the patient is doing in order to give context to the data. For example, it may be important for the physician to know that the patient is sleeping or engaged in strenuous activity prior to effecting a change to the patient's PIMD via remote programming. Various physiologic and patient-condition sensors may be used to determine the present status of the patient. Such sensors may be configured to sense one or more of cardiac electrical activity, cardiac mechanical activity, posture, acceleration or motion, respiration, minute ventilation, neural activity, brain activity, and muscle activity, for example. The sensors may be external or internal sensors (e.g., intra-body sensor network).

The data produced by the sensors may be transmitted to the PIMD and then to the PPC or directly from the sensors to the PPC. The PPC can stream data from any of these or other sensor to provide the physician with data concerning the patient's present condition or status. It may also be useful to know if the PPC is mobile or in its docking hub. Voice output from the PPC may be used to time-correlate sensor data (e.g., EGM data) so that the physician knows what to look for and the patient's reaction. Also, time stamp data may be appended to sensor data and/or an event marker may be appended to sensor data that results from patient actuation of a PPC button when an event is felt by the patient.

The above discussion of remote testing to determine capture threshold and remote programming to set pacing energy illustrates concepts of remote testing and remote programming which are equally applicable to other therapy parameters. Many applications for remote testing, remote programming, and/or event-driven remote testing and programming can be envisioned. Streaming data from the PIMD available over the LCN allows the physician to observe in real time the progress of testing or the results of a programming change. Similar approaches for remote testing and programming are applicable to many parameters used for electrical stimulation therapy, such as testing and/or setting A-V delays, V-V delays, refractory periods, selection of pacing modes, pacing rates, selection of the heart chamber to pace or the order in which heart chambers are paced, selection of pacing sites within a heart chamber or the sequence of pacing pulses delivered to the sites, and/or a variety of other therapy or diagnostic parameters.

Figure 7C:
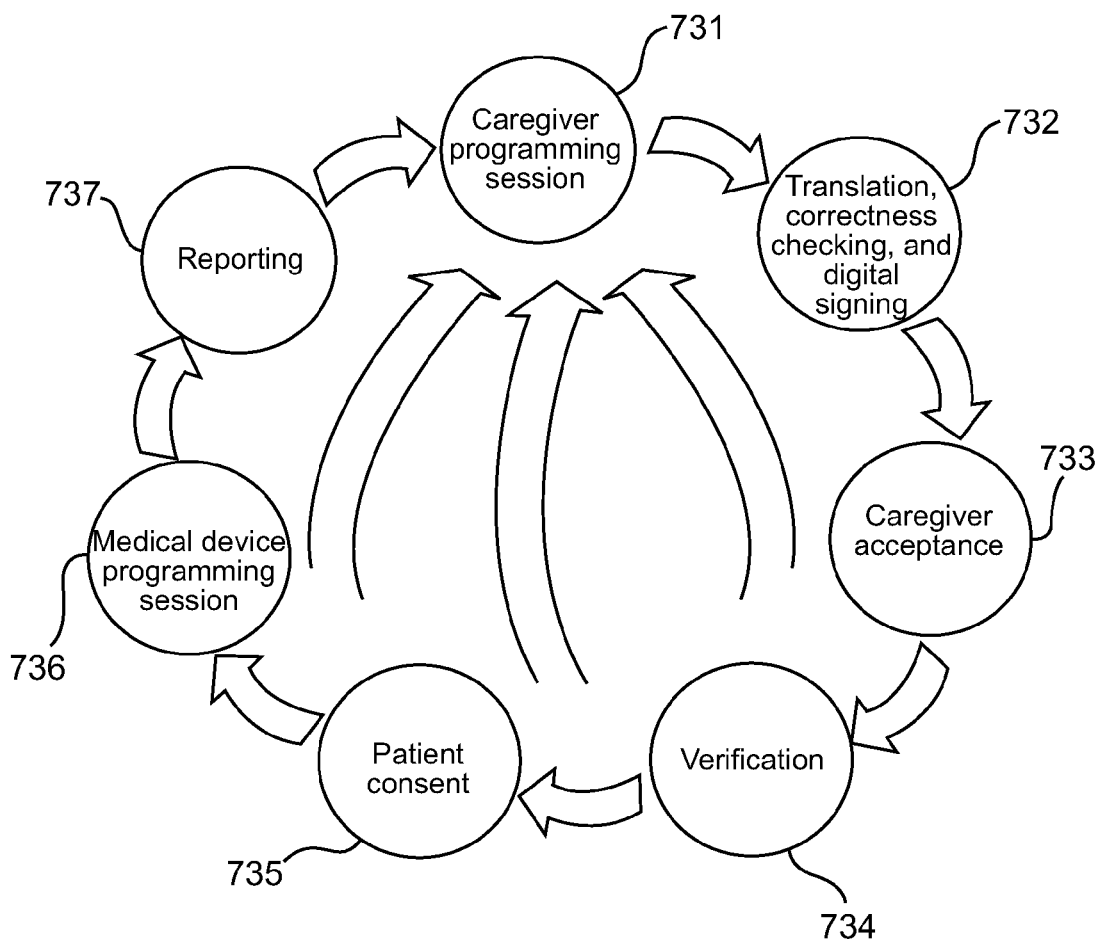
FIG. 7C is a process flow diagram showing a method for remotely programming a PIMD in accordance with embodiments of the present invention.

Remote programming may be initiated by caregiver action and may end with the reporting of the success or failure of the application of the programming to the intended PIMD back to the caregiver. FIG. 7C is a process flow diagram showing a method for remotely programming a PIMD, in accordance with one embodiment. Remote programming is performed as a sequence of operations, which, in specific instances, can be suspended or broken at specific points as necessary.

Initially, a caregiver performs a remote programming session (operation 731) through a data entry mechanism. Caregiver-selected programming instructions and parameters are translated by a regulated server into PIMD-formatted commands, which are checked for correctness and digitally signed (operation 732). The PIMD-formatted commands are also reverse translated and provided to the caregiver in displayable form for acceptance or rejection (operation 733). If the translated programming is rejected by the caregiver, control reverts back to the caregiver programming session (operation 731). Otherwise, the PIMD-formatted commands are marked for delivery to the server and, following receipt by the server, are verified for authenticity and integrity (operation 734).

In a further embodiment, the PIMD itself also performs verification of the commands, either in addition to or in lieu of the server. Assuming the commands are verified, the patient consent is confirmed (operation 735) prior to application of the commands. However, if the patient does not provide consent, control again reverts back to the programming session (operation 731). Upon consent, the server performs a programming session (operation 736). If the session is interrupted and not resumed, or abnormally terminates, the original PIMD programming is restored and control reverts back to the programming session (operation 731). Upon successful programming, the server interrogates the PIMD following programming session completion to report post-programming results to the caregiver (operation 737) for review and evaluation. Additional implementations for remote programming, aspects of which may be used in conjunction with various embodiments discussed herein, are described in commonly owned U.S. Patent Publication No. 20070185547 and U.S. Pat. No. 7,710,648, which are incorporated herein by reference.

PPC with Reduced Feature Set

Figure 8:
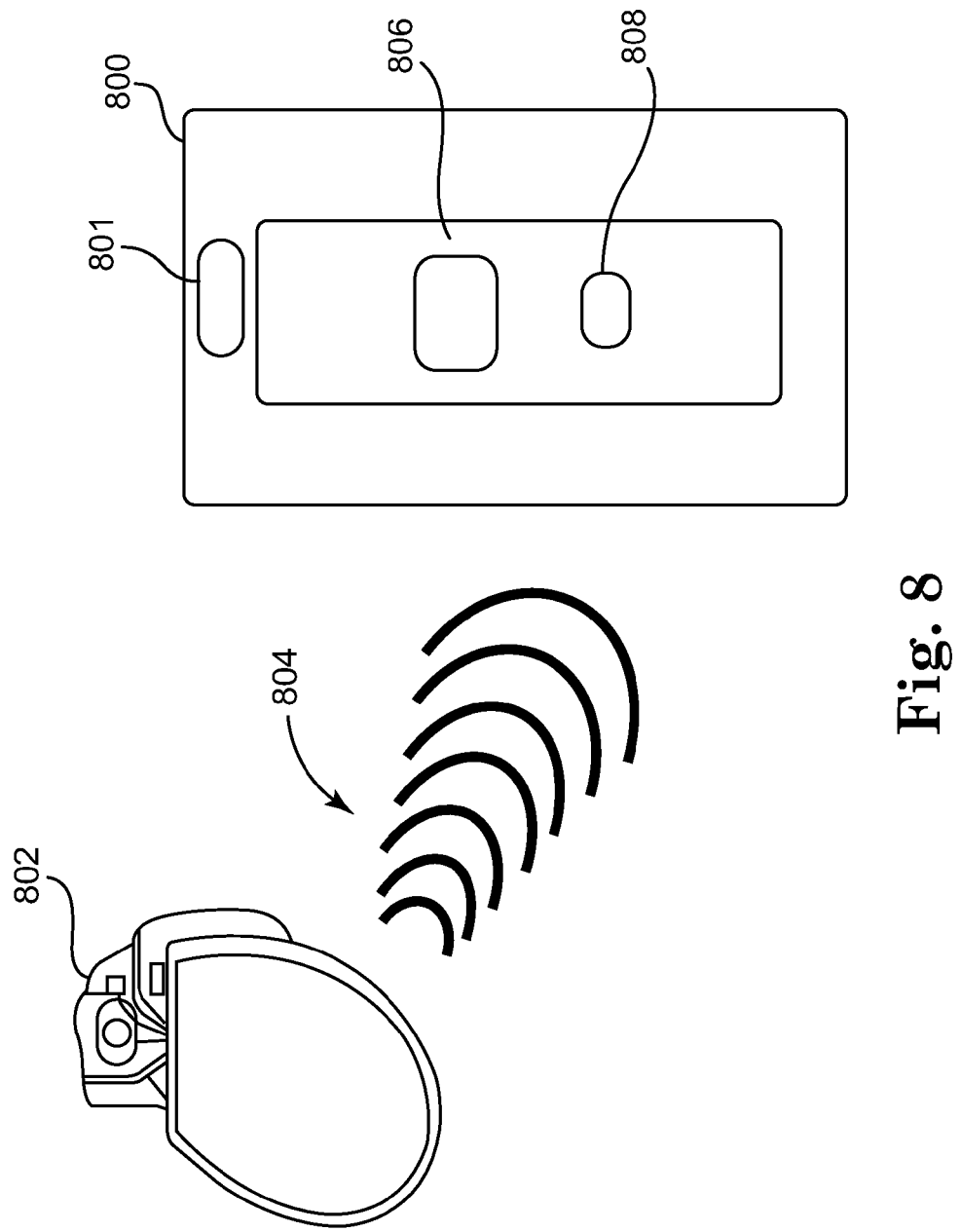
FIG. 8 illustrates a PPC having a reduced feature set and a relatively small form factor in accordance with embodiments of the present invention.

FIG. 8 shows a PPC 800 paired with a PIMD 802 and communicatively coupled thereto via a communications link 804. The PPC 800 may be implemented to provide a wide spectrum of capabilities and functionality. Within this spectrum, the PPC 800 may be configured to provide a variety of features or a limited number of features. In some implementations, for example, the PPC 800 may be configured to have a reduced number of features and capabilities (e.g., a reduced feature set PPC). A PPC 800 configured to have a reduced set of features advantageously reduces the complexity and cost of the device, and enhances acceptance of the device by less sophisticated users. A PPC 800 having a reduced set of features also provides for lower power consumption, such as by minimizing or eliminating a display or other user interface components. The PPC 800 may also be implemented to incorporate a variety of features and capabilities that provide for a wide range of functionality, as will be discussed below with reference to other embodiments.

FIG. 8 illustrates a PPC 800 having a reduced feature set and a relatively small form factor. For example, the PPC 800 shown in FIG. 8 may weigh less than about 6 ounces, and be small enough to fit easily in a purse or pocket. The PPC 800 has a simple user interface (U/I), which is shown to include a single button 801, a small LCD 806 that can provide basic status information (e.g., date, time, signal strength, and battery status), and an LED 808. The LED 808 may indicate ON status of the PPC 800 or other operational status indication. In one implementation, illumination of the LED 808 (or illumination of a green color for a multi-color LED 808, for example) may indicate that the PPC's battery is sufficiently charged to provide at least 24 hours (or other duration) of continuous service. The LED 808 may be controlled to implement a flashing scheme, which may include different colors, that communicates information to the patient. For example, a green ON color may indicate acknowledgement that interaction with the user was successful (e.g., a quick flash green light).

The button 801 may provide basic functionality, such as for initiating patient-interrogated transmissions and pairing/re-pairing procedures. The button 801 may also be actuated by the patient for indicating a distress condition of the patient, to which an emergency service may respond (e.g., 911 alert/call). In this regard, the PPC 800 may be configured to include a GPS transponder or transceiver, or provide location information via other approaches used for locating cellular phone users, which may be used to locate the PPC 800 and, therefore, the patient in an emergency situation. In addition to GPS or other location information, the PPC 800 may communicate patient information obtained from the PIMD 802, which can provide important information about the condition of the patient (e.g., the patient's vital signs obtained remotely by the emergency response service/technician, in addition to location information).

The PPC 800 may have a reduced feature set that excludes a keypad or other more sophisticated user input device, and may also exclude voice channel components associated with conventional cellular phones, for example. The PPC 800, in this configuration, preferably utilizes data or signaling channels of the cellular infrastructure to facilitate communications with remote services and systems.

In some configurations, the button 801 may be a multifunctional button (e.g., contact sensitive switch, multi-state switch or rocker switch). Button activation for controlling PPC functions may include one or more of a quick click, a double click, and a long hold. A button clicking scheme may be developed to perform a variety of operations, including initiating a PIMD 802 interrogation when the patient feels poorly, calling the APM server, and initiating delivery of a pre-configured SMS message to pre-determined parties (e.g., physician, neighbors, friends, children, relatives, emergency response service) to alert the recipient that the patient is in distress or need of attention.

If the PPC 800 detects a condition necessitating a shock and the shock is delivered, the PPC 800 may be programmed to automatically upload data to the APM server, which updates the APM server web site. Detection of the event, remedial action taken by the PPC/PIMD, and initiation of the automatic upload process should be communicated to patient, such as by a flashing LED sequence, so that the patient knows the event has been addressed and recorded. In cases where the APM server needs the patient to perform a function using the PPC 800, the APM server may initiate a phone call to the patient, and request that the patient activate an appropriate button click.

The PPC 800 may incorporate a speaker (preferably without a microphone in the case of a reduced feature set PPC 800, but a microphone can be included on a more robust PPC configuration). An audible feedback mechanism may be implemented as another means of communicating with the patient. The audible output from the speaker is preferably tonal, but voice output can also be employed. A "quiet mode" can be activated, such as by a 5 second button hold, to disable the speaker and, if desired, transition to a vibration/silent mode, if the PPC 800 is equipped with a vibrator device. The PPC 800 may be programmed to produce tones that can be used to transfer data via a TTM scheme, which can be a backup way of communicating to the APM server if cellular network service is unavailable. The speaker may produce a beeper sequence that can be used as a locator (via a button on the PPC's docking hub).

Configurable PPC

A PPC implemented in accordance with embodiments of the present invention may be dynamically configurable via interaction with an APM server and/or a PIMD. This capability of dynamically altering the configuration of a PPC serves to enhance cooperative operation between the PPC, PIMD, and APM system.

FIG. 9A shows an illustration of a multiplicity of PPCs 800 communicatively coupled to an APM server 850 via a network 830. According to the embodiment shown in FIG. 9A, the APM server 850 is coupled to a metadictionary 852. The metadictionary 852 stores information concerning the various types of PIMDs that are supported by the APM server 850. For example, the metadictionary 852 may store detailed information about the serial number, make, model, software/hardware, features, device type or family, etc. about each PIMD that is supported by the APM server 850. The metadictionary data, in short, identifies the capabilities of each PIMD of the system. This information has a number of uses, such as facilitating dynamic configuring of the PPCs 800.

According to one approach, a PPC 800 is paired with its corresponding PIMD 802, such as the paired devices shown in FIG. 8. The PPC 800 preferably receives identification information from the PIMD 802 that uniquely identifies the PIMD 802, such as the model and serial number (e.g., concatenated or combined) of the PIMD 802. The PPC 800 may then communicate this identification information to the APM server 850, which accesses the information for the particularly PIMD 802 stored in the metadictionary 852. Using this information, the APM server 850 may send data to the PPC 800 that configures the PPC 800 to cooperatively operate with the PIMD 802 in accordance with the metadictionary data. In this manner, an "off-the-shelf" PPC can be dynamically configured for use with a particular PPC during a pairing operation via the APM server 850.

For example, the metadictionary data for a particular PIMD 802 may include power capacity and consumption data for the PIMD 802. In response to this data, the PPC 800 may adjust the manner in which it effects communications with the PIMD 802, such as by increasing or decreasing the frequency of non-life critical data from the PPC 800 to the PIMD 802 for transfer to the APM server 850. Various data compression schemes may be used to reduce the volume of data transferred between the PIMD 802 and the PPC 800. In one approach, a number of data compression schemes are available for effecting data transfer between the PIMD 802 and the PPC 800. Metadictionary data may be communicated from the APM server 850 to the PIMD 802 for purposes of substituting or modifying the data compression scheme used by the PIMD 802 and/or PIMD 802, such as for power conservation purposes or for enhancing compatibility with the particular networking protocol.

By way of further example, metadictionary data may be transferred from the APM server 850 to the PPC 800 that modifies a data interrogation routine of the PPC 800, thereby altering the type (and format, if appropriate) of data to be acquired from the PIMD 802 by the PPC 800. This may be particularly useful when conducting research or developing clinical trial protocols. The type of data to be acquired from the PIMD 802 of a particular patient may change as the patient's status (e.g., heart failure status or tachyarrhythmia status) changes over time. The volume of data acquired from the PIMD 802 and/or timing of data transfers may be modified using the PPC 800 in response to metadictionary data received from the APM server 850.

The PPC 800 may also receive a decoder ring associated with its paired PIMD 802 from the metadictionary 852 via the APM server 850. A decoder ring is associated with the particular decoding scheme or logic used by a type or family of PIMDs. Every PIMD has a unique decoding scheme that is identified by the decoder ring associated with the particular PIMD. The decoder ring for a particular PIMD 802 may be transferred from the APM server 850 to the PPC 800 that is paired with the particular PIMD 802. For example, the decoder ring for a particular PIMD 802 may be stored in a SIM card of the PPC 800. Transferring the decoder ring to the PPC 800 at the time of pairing with its associated PIMD 802 advantageously allows a "generic" PPC 800 to be used for effecting communications between a wide variety of PIMDs and the APM server 850.

Firmware of the PPC 800 may be updated by the APM server 850. For example, the metadictionary 852 may identify a number of PPCs 800 that require a particular change in firmware. Version updates and patches may be distributed by the APM server 850 to appropriate PPCs 800 identified by the metadictionary data. By way of further example, communications firmware updates may be distributed to appropriate PPCs 800 to update the PPCs 800 capability to communicate over one or more cellular networks as such networks evolve over time.

In some configurations, the PPCs 800 may incorporate a multi-band radio, such as a quad-band radio. The PPCs 800 may also include multiple short-range radios, such as ISM and SRD radios). The PPCs 800 may switch to different radios depending on the geographical location of the PPCs 800 and the available cellular service (e.g., when traveling from the US to Europe). The PIMD 802 may also change radios, such as in accordance with radio changes made by the PPCs 802 (e.g., ISM to SRD). The PPCs 800 may also include an inductive coil that can be used to establish an auxiliary or backup link between the PPCs 800 and the PIMD 802. In this regard, the PPCs 800 may be used in the similar manner as a conventional wand.

According to one implementation, PPCs 800 may incorporate a software defined radio (SDR) device or module (permanent or replaceable) that can be configured to dynamically define and redefine the communications capabilities of the PPCs 800. An SDR device is a radio communications device that can be programmed to tune to any frequency band and receive any modulation across a large frequency spectrum by means of programmable hardware which is controlled by software.

According to one implementation, the hardware of an SDR incorporated in the PPC 800 may include a superheterodyne RF front end that converts RF signals from and to analog IF signals, and an analog-to-digital converter and digital-to-analog converters which are used to convert a digitized IF signal from and to analog form, respectively. An SDR performs signal processing using a generally purpose CPU or a reconfigurable piece of digital electronics. Incorporating an SDR in the PPC 800 advantageously provides for a radio that can receive and transmit a new form of radio protocol simply by running new software that can be distributed to the PPC 800 from the APM server 850. An SDR may be configured to operate with different modalities, including short range modalities (e.g., Bluetooth, Zigbee, FM) and long range modalities (e.g., RF telemetry utilizing MICS, ISM or other appropriate radio bands). A more advanced SDR may support multiple communications modalities as selected by the PPC 800 or APM 850. These various modalities typically differ in terms of power consumption and transmission range, and may be programmed, enabled, and/or selected based on these and other considerations.

PPC Diagnostics

The PPC 800 preferably has a "Built-In Self Test" mode for performing various diagnostics. Because the PPC 800 preferably has at least two radios (e.g., cellular and ISM/SRD), these radios may be used to perform various diagnostics. For example, one radio of the PPC 800 can be used to transmit over a network connection, and the other radio can listen and verify that the received power is as expected. The same can be repeated, but with the two radios swapping transmission and reception roles. This test can be done at a reduced power mode and at a frequency of interest as the RF regulations allow. Also, the cellular radio gets information back from the tower about the PPC signal strength at the tower, and the PPC 800 sees the power of the tower signal as received.

By way of example, the transmitter of a first radio of the PPC 800 may be set to a frequency which a second radio of the PPC 800 can receive. A signal transmitted from the first radio is coupled to the second radio via the PPC's antenna system or via an RF coupler, an RF switch, or an attenuator. A simple diode receiver can also be used to provide a second measurement of transmission power to eliminate ambiguity. The preferred approach is to use the PPC's existing antenna system so that the complete RF path can be verified.

Functional testing may be performed using a first configuration by which the first radio operates as a transmitter and the second radio operates as a receiver. Functional testing may be performed using a second configuration by which the second radio operates as a transmitter and the first radio operates as a receiver. According to one approach, functional testing is performed using one of the first and second testing configurations to detect a performance deficiency, and functional testing is performed using the other of the first and second configurations only in response to detecting the performance deficiency. Functional testing may be terminated (and a message generated) upon detecting a performance deficiency using only one testing configuration in order to preserve PPC and/or PIMD power. A detected performance deficiency may be verified using the other testing configuration if desired.

The transmit power/receive sensitivity can be measured, data or modulation can be verified, and frequency accuracy can be measured by varying either or both of the receiver and transmitter frequency. Out of band rejection can be measured also by varying the transmitter frequency to a known "out of band" frequency. This testing approach may be performed or repeated by using the second radio as the transmitter and the first radio as the receiver.

If PPC location information is available, the data may be stored on the APM server to verify that the PPC 800 is the same one that performed previous tests from that location. If the ISM/SRD radio is used to scan the local environment and again using location information, it is possible to verify that the environment is still favorable for PIMD data transmission or when that location is clean for such traffic. This provides a mechanism to optimize connections for PIMD data traffic.

A appropriate pause in PIMD telemetry may be necessary to allow the cellular connection to remain alive. This is needed so that a ping can get through and the cellular connection stays open, to stay connected via the tower or to keep a communication session open. If necessary, it may be useful to briefly hold off PIMD communication during an open session to allow the cellular connection to stay associated with its tower as required. Also, PIMD communication can be adjusted to interleave an active cellular data call so that both can be active in different time slots. This would allow use of a common antenna multiplexed between the two radios when both are active.

Streaming data may be accomplished by operating in a burst mode (intermittent mode). For example, data is first transmitted from the PIMD 802 to the PPC 800 via ISM/SRD/MICS, and then to the cellular network. According to another approach, it is possible for the cellular radio of the PPC 800 to communicate directly with the PIMD's transceiver. This can be accomplished by pushing a communications protocol stack to the processor of the cellular radio of the PPC 800 to access the ISM, SRD, or MICS radio bands.

When traveling abroad, the PPC 800 is configured for use in accordance with its physical location. This may involve setting the ISM/SRD radio bands based on cell phone frequency. Also, the PPC 800 adjusts to ensure compliance with privacy requirements for each location. In Japan, for example, this may involve turning off/on the RF radio based upon location as determined from a cell tower (or absence of a tower).

Expanded PPC User-Interface using Separate Communications Device

Figure 10:
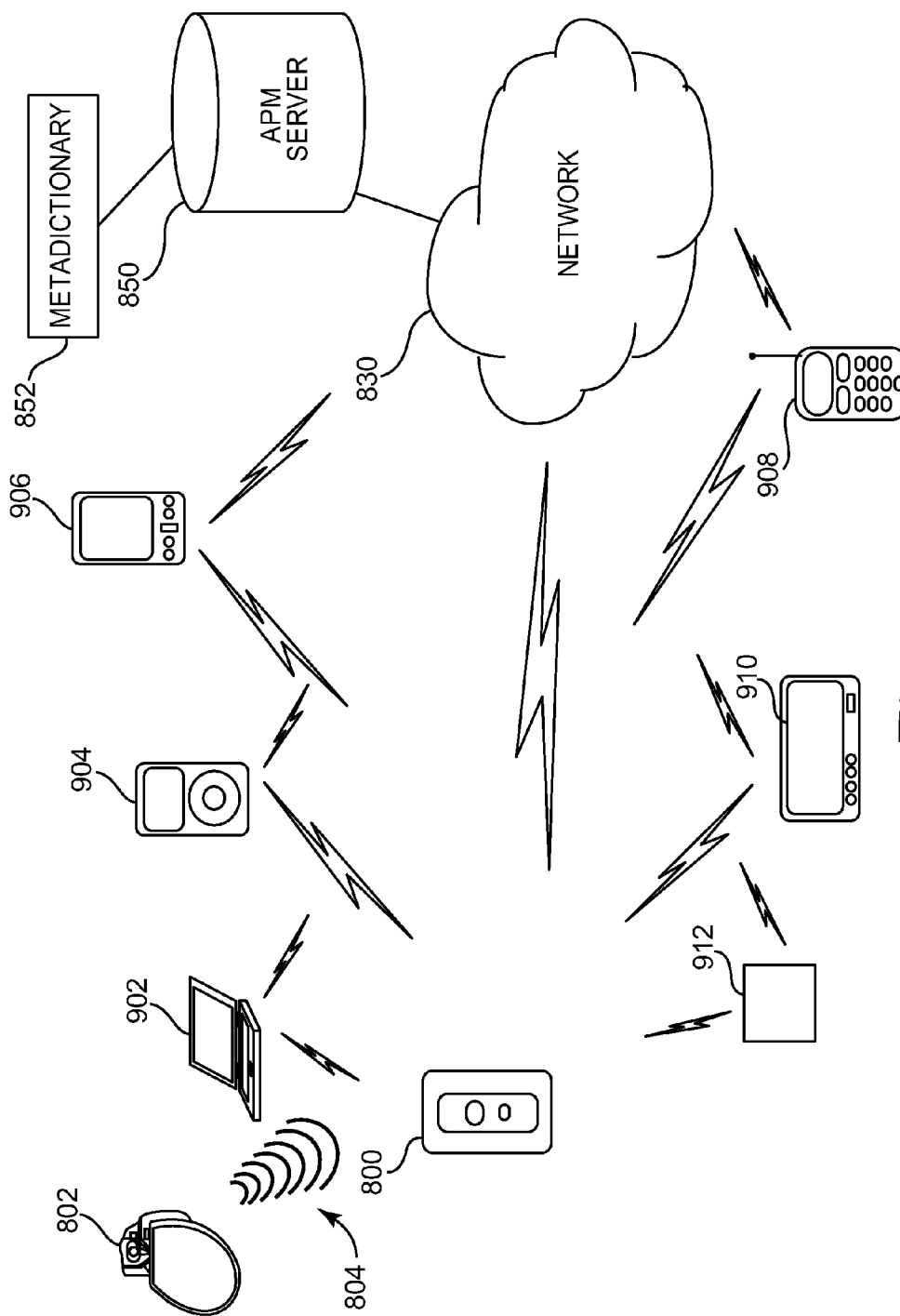
FIG. 10 illustrates a PPC configured with a reduced feature set, and various generic network access devices whose user interface capabilities can be exploited to expand the user interface features of the PPC in accordance with embodiments of the present invention.

FIG. 10 illustrates a PPC 800 configured with a reduced feature set, as discussed above. Although the PPC 800 shown in FIG. 10 may have a minimum of features, enhanced user interface capabilities may be provided via cooperation between the reduced feature set PPC 800 and a wireless (or wired connected) device configured to communicate with the PPC 800. For example, the PPC 800 may be configured to communicate with one or more local devices, such as cellular phones 908, portable computers 902, personal digital assistants (PDA) 906, digital music players 904, tablet computers 910, or any other device represented by generic device 912. Many of the user interface/user input facilities (e.g., LCD displays, keypads, mouse, stylus) provided by these devices may allow the patient or clinician/caregiver to interface with the PPC 800, as if these facilities were otherwise built into the PPC 800 and APM server 850. For example, data and graphics indicative of physiologic signals and information may be presented on a display of such local devices. The patient may also interact with the PPC 800 via the user interface devices of a local communication device (e.g., PC or PDA) via a hub or docking station configured to cradle the PPC 800, such as that shown in FIG. 14.

Expanded interfacing capabilities between the PPC 800 and external device(s) may be effected with or without involvement of the APM server 850. For example, the local interfacing device (e.g., laptop) may communicatively couple wirelessly or via hardwire connection (e.g., USB or FireWire) with the PPC 800 and acquire data from the PIMD 802. The local device may display various types of data acquired from the PIMD 802, such as ECG waveforms, sensor data, event counters, histograms, and other information of interest. Generally, view-only access to the PIMD is preferably granted to local devices such as those shown in FIG. 10. It is noted that an appropriate local device, such as a laptop, may be configured to emulate a PIMD programmer, and that an authorized clinician may interrogate or program the PPC 800 locally using such local device. The data associated with local PIMD programming and/or interrogation may be uploaded to the APM server 850 via a wireless connection or hardwired connection.

This system configuration is particularly useful in the context of emergency response, such as by allowing ambulance EMTs the capability to evaluate PIMD information for a patient that may be impaired, distressed or unconscious, for example. The local device may also be configured to interface with the APM sever 850, and may effect a life-critical connection between a clinician communicating via the APM server 850 and the local device via PPC 800. In an emergency room scenario, PIMD data may be transferred to a laptop or other computer system in the ER to allow physicians to quickly evaluate real-time and stored physiologic data for the patient.

Emergency Calling and Response

It may be important to ascertain the present location of a patient who may be in distress or requires emergency attention. The PPC 800 may be used to locate the patient, such as by using a known triangulation locating technique that uses the PPC 800 and a multiplicity of cell towers. Such techniques may determine the location of the PPC 800 by measuring and comparing signal strengths or other parameter of signals communicated between the PPC 800 and a multiplicity of cell towers. Preferred techniques are those that do not require additional PPC hardware, such as an additional dedicated antenna or a GPS or other satellite receiver, for example. It is understood, however, that some embodiments may include such additional components.

Various known techniques may be employed to locate the PPC 800 and, therefore, the patient (or provide a good estimate of patient location). Examples of PPC location techniques that may be employed in accordance with embodiments of the present invention are disclosed in U.S. Pat. Nos. 5,293,642; 5,873,040; 6,088,594; and 6,477,363, all of which are incorporated herein by reference.

The PPC 800 may be configured to initiate an emergency call for assistance, such as by initiating a 911 call. The PPC 800 may be programmed to automatically place a 911 or other emergency call based on predetermined conditions, such as when the PIMD 802 detects a potentially life-threatening condition (e.g., VT, VF, asystole, abnormally low or absent respiration rate) and communicates this condition to the PPC 800. Classes of events that, if detected, warrant immediate initiation of a 911 or other emergency call include: 1) myocardial infarction; 2) prediction of myocardial infarction; 3) pre-event identification of a serious or life-threatening upcoming event; 4) VF/SCD (sudden cardiac death); and 5) specific request by the PPC 800 (via an indicator or synthesized voice message broadcast via a PPC speaker) to call 911 and, if applicable, a request for use of an AED or CPR on the patient. In some embodiments, the patient's cardiac rhythm acquired by the PIMD 802 may be transmitted to the PPC 800 which then broadcasts the patient's rhythm to help an emergency responder synchronize chest compressions during delivery of CPR. The PIMD 802 may attempt to initiate an autocapture procedure in an attempt to increase the patient's heart rate during attempted resuscitation, and an audible or visual alert may be generated by the PIMD in the event that the PIMD cannot effect capture and to indicate that immediate assistance is needed.

The patient may be permitted to initiate a 911 or other emergency call, such as by actuation of a button reserved for emergencies on the PPC 800. In cases where an emergency call is manually initiated by the patient, the PPC 800 may be programmed to verify presence of a patient condition warranting an emergency response. For example, the PPC 800 may interrogate the PIMD 802 prior to initiating an emergency call in response to patient actuation of an appropriate "emergency" button. The location of the PPC 800 may also be determined using triangulation or other technique discussed herein, and the PPC 800 may communicate with the PIMD 802 as a confirmation that the computed or estimated location of the PPC 800 is where the patient actually is.

Upon verifying presence of a patient condition warranting an emergency response, the PPC 800 initiates a 911 or other emergency call. As part of the PPC's emergency protocol, the PPC 800 may initiate a call to the patient's home phone or other advocate's phone to provide status to the patient's family or advocate after placing the emergency call. A call may also be made to the APM server 850, which may provide voice information as well as patient data, printouts, real-time ECG and other information to the EMT, ambulance, and/or hospital that is useful for treating the patient. This data may include, for example, the patient's drug regimen, allergies, recent medical evaluation data, physician information, and medical ID information.

In response to the PPC 800 determining that the patient condition does not warrant an emergency response based on the PIMD information, the PPC 800 may indicate to the patient that, although a request for emergency services has been requested by the patient, the condition does not warrant initiation of a 911 or other emergency call. The patient may be given the opportunity to manually initiate the emergency call after considering this information from the PPC 800, notwithstanding the "recommendation" by the PPC 800 that such emergency attention is not warranted based on the PIMD information. These features can aid in reducing false-alarms and unintended and/or unnecessary calls to 911 services or other emergency service providers.

According to other embodiments, the APM server 850 may implement an emergency response methodology in response to information received from the PPC 800. The APM server 850 may first determine if the PPC 800 is paired with its associated PIMD 802. According a tiered response approach, the APM server 850 may assess PPC information and determine the level of patient risk. Based on the level of patient risk, the APM server 850 may take appropriate action. For example, the APM server 850 may determine the patient is at high risk and that immediate attention is warranted. For high risk situations, the APM server 850 may initiate a 911 or other emergency call. The APM server 850 may also initiate a patient location assessment using the PPC 800 and cellular infrastructure (or other technique as discussed herein) to locate the patient. This patient location assessment may also be initiated or requested by the emergency response service.

In medium risk situations, the APM server 850 may take time to evaluate the various data available for assessing the patient's present condition. This may involve acquiring additional PPC data, such as surface ECG or EMG data, and/or running particular algorithms to evaluate patient condition and the patient's risk level. Medium and lower risk situations may be resolved by communicating assessment information to the patient via the PPC 800 or by follow-up phone call (automated or personal) or other messaging resource. For example, the PPC 800 may provide "reassurance" or validation information to the patient that emergency services are needed or not needed, and/or to instruct the patient to contact the patient's physician or an emergency room, for example.

In some embodiments, the PPC 800 is programmed to evaluate patient risk based on all available information it has received from the PIMD 802 and/or the APM server 850. The PPC 800 may implement a similar protocol as discussed above for the APM server 850. For example, the PPC 800 may collected data from the PIMD 802 and determine the number of shocks delivered over a given time period. Based on the number of shocks delivered within a specified time range, the PPC 800 may distinguish a high risk situation from a medium risk salutation. If, for example, the PPC 800 determines that three shocks were delivered within the last 3 minutes, the PPC 800 may consider this a high risk situation and initiate a 911 call. If only a single shock has recently been delivered, then this event and the medium to low risk associated with it can be communicated to the patient in some form to reassure the patient. For example, this data and other relevant information may be communicated to the patient via a voice synthesizer and speaker provided in the PPC 800. In either situation, this data is preferably communicated to the APM server 850.

In other embodiments, the PIMD 802 is programmed to evaluate patient risk based on all available information it has acquired from the patient and/or received from the PPC 800 and/or the APM server 850. The PIMD 802 may implement a similar protocol as discussed above for the APM server 850, and cooperate with the PPC 800 and/or APM server 850 to implement an appropriate response protocol.

It is noted that real-time monitoring is preferably implemented during high and medium risk situations. During such situations, the data collected from the PIMD 802 may be dynamically changed to accommodate an increased or decreased need for PIMD data. Dynamically adjusting the type and quantity of PIMD data needed to evaluate a patient's condition is preferably implemented to conserve PIMD power, it being understood that this approach to changing the type, quantity, and frequency of PIMD data may be implemented in other situations in order to optimize PIMD power conservation.

PPC and APM System

Figure 11:
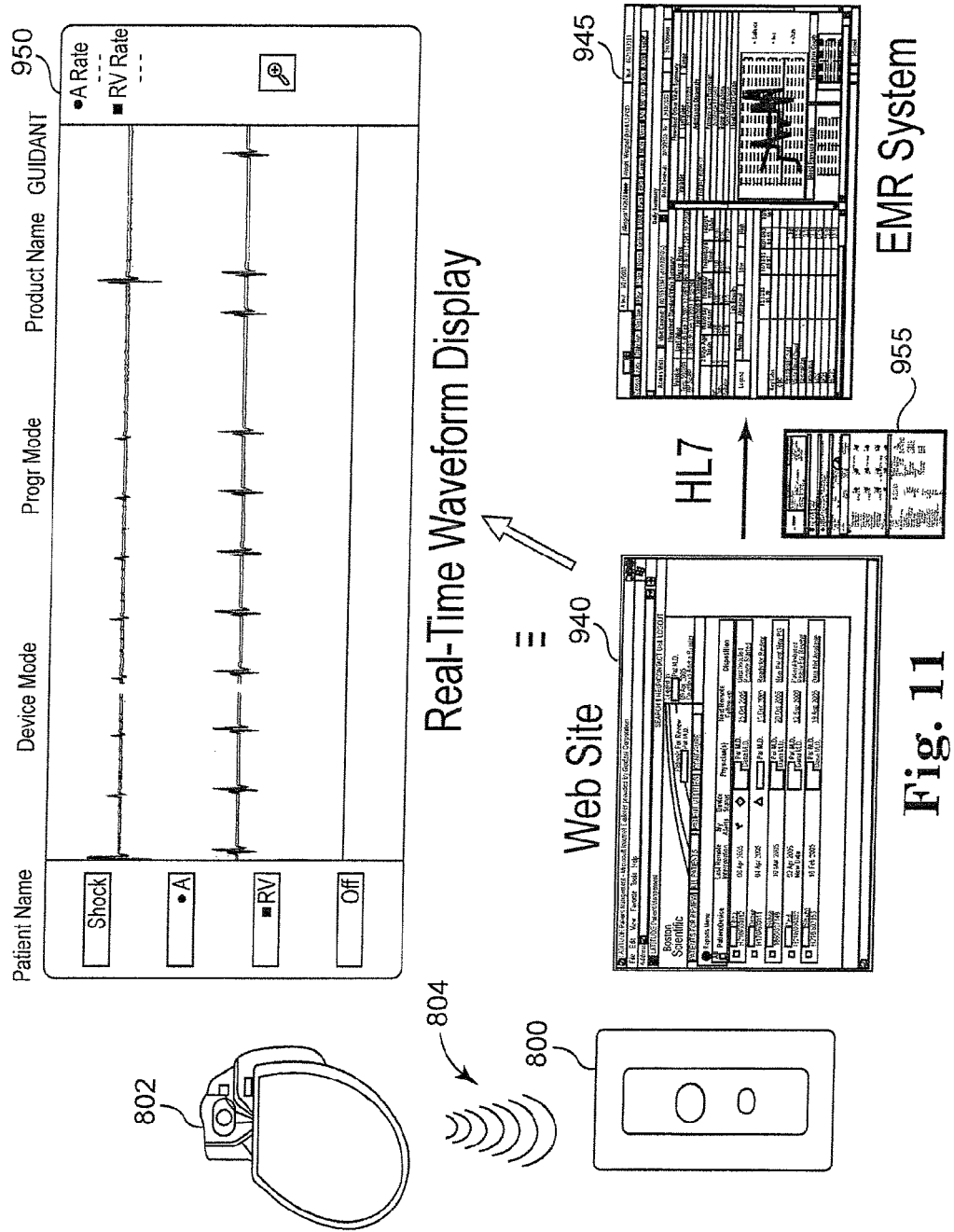
FIG. 11 illustrates various types of PIMD data that can be transferred from a PIMD to a PPC, from the PPC to an APM server, and from the APM server to the clinician or other user in accordance with embodiments of the present invention.

FIG. 11 illustrates various types of PIMD data that can be transferred from a PIMD 802 to a PPC 800, from the PPC 800 to an APM server 850, and from the APM server 850 to the clinician or other user. As is depicted in FIG. 11, various physiological data acquired by the PIMD 802 are transferred to the PPC 800. This data may be transferred by the PIMD 802 to the APM server 850 in real-time mode or batch mode. For example, occurrence of a predetermined event may trigger a data transfer operation from the PIMD 802 to the PPC 800. Based on the criticality of the event, the event data may be temporarily stored in the PPC 800 for later transmission to the APM server 850, in the case of less critical events. In the case of critical events, immediate connectivity may be made between the PPC 800 and the APM server 850, and PIMD data may be communicated to the APM server 850 in real-time (e.g., real-time streaming of PIMD data from the PIMD 802 to the APM server 850 via the PPC 800). It is understood that the term "real-time" connotes a manner of communicating data as fast as is practicable from a transmission source to a receiving device given real-world (i.e., non-ideal) technological practicalities, such as connection and transfer delays, among others.

In accordance with embodiments of the present invention, PIMD interrogation, programming, data transfer operations (e.g., incremental data transfers), and query/response protocol operations need not be subject to a predefined schedule (e.g., between nighttime hours of 1-3 AM), but may be event based. Events detected by the PIMD 802 or actions initiated by the patient (e.g., pushing a button on the PPC 800) may trigger cooperative operation between the PIMD 802 and PPC 800 or between the PIMD 802, PPC 800, and the APM server 850. Certain events may trigger real-time connectivity between the PPC 800 and the APM server 850, while others may trigger store-and-forward data transfer operations. It is noted that it may be desirable to limit patient interaction with the PIMD 802 in non-critical situations, such as for conserving battery power.

Cooperative operation between the PIMD 802, PPC 800, and the APM server 850 provides for a number of useful real-time capabilities. For example, real-time monitoring of patients by remotely located clinicians may be realized, which may include real-time waveform display, real-time physiological monitoring for remote triage, real-time physiological monitoring and display at a remote clinician location, and real-time leadless ECG waveform viewing. Real-time clinical alerts for high risk patients may be generated at a remote location in response to predetermined patient events. Patient data may be streamed to the APM web site and displayed within a browser plug-in, which may include smoothed anti-aliased display of physiological waveforms at 24 frames per second or higher. In this regard, cooperative operation between the PIMD 802, PPC 800, and the APM server 850 may facilitate implementation of an "always on" or at least an "always available" life critical network when the PPC 800 establishes a network connection.

Figure 12B:
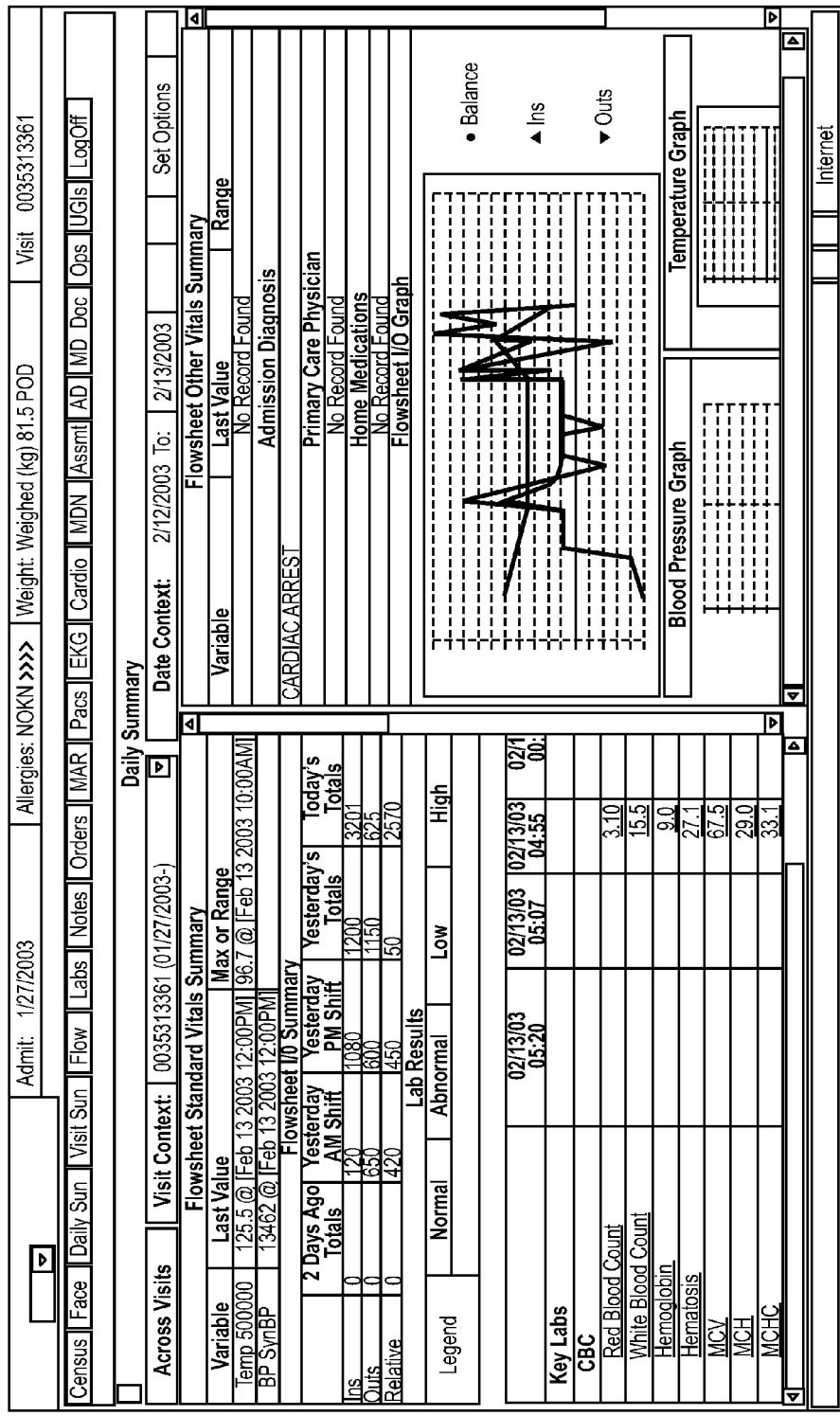

FIG. 11 shows data transferred from a PIMD 802 and PPC 800 to a website 940 supported by an APM server 850. Data acquired from the PIMD 802 may be organized in the manner shown in FIG. 11, an expanded view of which is shown in FIG. 12A for illustrative purposes. Data acquired from the PIMD 802 and stored in the APM server 850 may be transferred to, and incorporated within, an electronic medical records system 945, summary data from which is shown in FIG. 12B for illustrative purposes and additional details of which are disclosed in commonly owned U.S. Patent Publication No. 20070226013, which is incorporated herein by reference.

FIG. 11 also shows real-time PIMD 802 data displayed graphically. In this illustrative depiction, real-time EGM data for multiple channels (RV, atrial, and shock channels) is displayed. Atrial and ventricular rates, along with other data, may also be displayed. Date regarding the patient, device mode, programmer mode, and the PIMD 802 may be displayed. Detailed data 955 concerning the PIMD 802 may be displayed in real-time and/or output in report form, an example of which is shown in FIG. 12C for illustrative purposes.

PPC Communications Interfaces

The PPC 800 preferably incorporates a built-in transceiver that may be configured to establish bi-directional communication with a network utilizing various known communication protocols, such as those used in cellular networks. The PPC 800 also incorporates a short range transceiver for establishing a local communication link 804 between the PPC 800 and PIMD 802, and, in some embodiments, between the PPC 800 and one or more sensors disposed on the PPC 800 (or other patient sensors in proximity to the PPC 800). The local communication link 804 may be established in accordance with a variety of known protocols, such as MICS, ISM, or other radio frequency (RF) protocols, and those that confirm to a Bluetooth standard, IEEE 802 standards (e.g., IEEE 802.11), a ZigBee or similar specification, such as those based on the IEEE 802.15.4 standard, or other public or proprietary wireless protocol.

The PPC 800 may incorporate a communications port 814 that may be configured to receive a connector for a hardwire communication link. In such a configuration, a conductor (electrical or optical) may be connected between the hardwire connector or communication port 814 of the PPC 800 and an appropriate connector of a patient-external system, such as a laptop. The hardwire connection port 814 of the PPC 800, and any necessary interface circuitry, may be configured to communicate information in accordance with a variety of protocols, such as FireWire™ (IEEE 1394), USB, or other communications protocol (e.g., Ethernet). It is understood that various hardwire connection protocols allow for the transmission of power in addition to data signals (e.g., USB), and that such connections may be used to recharge an internal or backup battery source 812 of the PPC 800.

PPC Power Features

According to various embodiments, the PPC 800 may include a rechargeable battery 821 having a relatively high capacity. For example, the rechargeable battery 821 of the PPC 800 may have a capacity of 1200 milliamp hours (e.g., 120 days standing time, 8 hours transmission). The PPC 800 may include a secondary battery 812 as fail-over mechanism or to increase the capacity of the battery resources of the PPC 800. In certain configurations, the PPC 800 may include a capacitor or battery that is rechargeable by turning a crank that turns a dynamo coupled to the capacitor or battery. The PPC 800 may incorporate an integral crank or a socket that receives an integral or detachable crank. Other manual recharging mechanisms may include a generator coupled to a displaceable mass.

Various kinetic energy harvesting mechanisms may be incorporated that harvest kinetic energy resulting from PPC movement which can be stored in a battery of the PPC 800. Patient movement of the PPC 800 from walking, for example, may cause movement of a displaceable mass that mechanically activates a generator, which converts the kinetic energy imparted by the displaceable mass to a DC recharge signal. The PPC's battery may be recharged inductively, such as by use of a tank circuit. A manual or automatic-mechanical recharging capability may be particularly useful in regions of the world that have sparse or unreliable power distribution systems. The PPC 800 preferably generates an alert to indicate when main rechargeable battery 821 power is low.

Management of the PPC's battery status may be monitored and managed via the web site of the APM server (e.g., via a dashboard application/interface). PIMD battery life may be optimized or extended by properly coordinating data transfers between the PIMD 802 and the PPC 800. It is known that a significant amount of PIMD power is consumed during active use of the wireless transceiver of the PIMD 802. This usage of power may be reduced or optimized by proper coordination of the data transfer operations between the PIMD 802 and PPC 800. According to one approach, predefined clinical events as detected by the PIMD 802 may be categorized in terms of criticality. The manner in which data associated with these events is transferred from the PIMD 802 to the PPC 800 may be dependent on the level of event criticality. For example, data associated with less critical events may be transferred to the PPC 800 with less frequency than data associated with events of higher criticality. Real-time connectivity between the PIMD 802, PPC 800, and APM server 850 may be reserved for events of highest criticality, such as life-threatening tachycardia events (e.g., VT or VF episodes). Data for less critical events may be batch transferred, for example, to reduce power consumption by the transceiver of the PIMD 802.

Managing PIMD Power using High Frequency Polling

According to some embodiments, the PPC 800 may be programmed to implement a high frequency polling protocol that effects necessary interrogations of the PIMD 802 while doing so in power efficient manner. High frequency polling according to embodiments of the present invention can be viewed as simulating event driven pushes by the PIMD 802 by high frequency polling by the PPC 800. It is understood that the term "high frequency" as applied to polling by the PPC 800 refers to the number of times (e.g., frequency of occurrence) the PPC 800 polls the PIMD 802 within a specified time period. A high frequency polling approach of the present invention may be implemented to acquire necessary data from the PIMD 802 in a power efficient manner. For example, a high frequency polling approach of the present invention may be implemented to facilitate acquisition of a requisite volume of timely data from the PIMD 802 to address the patient's present condition while using as little PIMD power as is practicable under present conditions.

High frequency polling according to the present invention effectively transfers at least some of the power burden (and preferably as much of the power burden as possible under the circumstances) from the PIMD 802 to the PPC 800 when effecting communications between the PIMD 802 and the PPC 800. High frequency polling according to embodiments of the present invention exploits the uniqueness of the source of data (i.e., the PIMD 802), PPC interaction with the PIMD 802, and APM server interaction with the PPC 800. The time and need for high frequency polling is dependent on a number of factors, including the type of PIMD 802 (e.g., anti-bradycardia device vs. CRT device), the type and volume of data needed over a given time period, and the various needs for communicating with the PIMD 802, among others (e.g., when the PPC 802 is sensing PIMD problems).

High frequency polling is particularly useful for reducing excessive power consumption by the PIMD 802 associated with PIMD "wake up" and other status inquiry events. Implementations of the high frequency polling according to the present invention exploit the PIMD's use of lower power when "listening" to an external device in comparison to the PIMD's need for higher power when "squawking" to an external device. The status and/or wake-up strategy implemented by the PPC 800 and PIMD 802 (or by the combination of the PPC 800, PIMD 802, and APM server 805) preferably moves the power burden from the PIMD 802 to the rechargeable PPC 800 as much as possible.

For example, a PIMD 802 may be operating at a low power level and awakened by the PPC 800 when needed. After the PIMD 802 is awakened, polling of PIMD data may be increased, resulting in a corresponding increase in PIMD power consumption. According to one approach, a two-mode wake-up strategy may be implemented based on a "status" mode and an "interrogation" mode. A status wake-up event preferably occurs relatively frequently, such as once per n hours, where n typically ranges between 1 and 6 hours, for example. This status wake-up event is preferably a low power event that involves transmission of a short duration message from the PIMD 802 to the PPC 800 indicating that the PIMD 802 has nothing to report (which may also be reported to the APM server 850). An interrogation wake-up event preferably occurs relatively infrequently, such as once per day, for example. This interrogation wake-up event is typically a higher power event that involves a PIMD interrogation and transmission of interrogation data from the PIMD 802 to the PPC 800 (and subsequently to the APM server 850).

A tiered PIMD polling methodology may be employed in accordance with embodiments of the present invention. According to some embodiments, a tiered polling approach involves the PPC 800 (by itself or in response to a command signal from the APM server 850) transmitting a ping to the PIMD 802. In response to the ping, the PIMD 802 transmit a signal indicating (1) that the PIMD 802 does not need to establish a communications/interrogation link or require a status check, or (2) the PIMD 802 needs to be interrogated, in which case a communications link is established between the PPC 800 and the PIMD 802, which requires powering up of the PIMD's transceiver and other necessary components.

If the result of the ping indicates that the PIMD 802 cannot be located or the PPC 800 is out of range, then a message is preferably sent via cell or land phone, email, or otherwise to the patient that the PPC 800 needs to be carried to establish required communication with the PIMD 802. If the result of the ping indicates that all is nominal, and that this nominal status is confirmed n times over m hours (e.g., 10 times over 10 hours), then it is assume that all is nominal. In this scenario, it is the PPC 800 that is predominately consuming power rather than the PIMD 802, which is preferred since the PPC's power source is typically rechargeable. If it is determined from historical data that the patient almost always carries the PPC 800, such as by repeated successful receipt of a signal from the PIMD 802 in response to a ping, the polling strategy may be modified from a pinging strategy to some other lower power strategy, such as scheduled strategy via remote programming by the APM server 850.

According to another approach, a hybrid ping methodology may be implemented in which the PIMD 802 performs some level of pinging and the PPC polls on a regular basis. By way of example, the PIMD 802 may be programmed to transmit a ping signal on a regular basis (e.g., every hour or few hours) in order to determine if the PPC 800 is in range. The PPC 800 may be programmed to poll the PIMD 802 on a regular basis, as discussed previously. To combined approach of limited PIMD pinging and PPC polling provides for increased opportunity to determine PIMD status and, if necessary, establish connectivity between the PIMD 802, PPC 800 and/or the APM server 805.

A pinging methodology may also be used to assess the signal strength by the PIMD 802 or the PPC 800. This assessment may be used by the PIMD 802 and secondarily the PPC 800 to dynamically modify the device's network interface transmission power. For example, a ping transmitted by the PPC 800 may be assessed by the PIMD 802 to determine the amount of power needed for the PIMD 802 to effect communications with the PPC 800 (if needed). The ping may be assessed by the PIMD 802, for example, to determine the minimal amount of power needed for the PIMD 802 to transmit a signal responsive to the ping that will be received by the PPC 800. It will be appreciated with the PIMD 802 can dynamically assess its transceiver power needs based on each ping or other type of signaling generated by the PPC 800. In a similar manner, the PPC 800 can regulate its transceiver power as needed, although PIMD power conservation preferably predominates over that of the PPC 800.

Other methods of implementing PIMD wake-up strategies are contemplated. For example, acoustic signals generated from a source outside the patient's body may be detected by the PIMD 802 (e.g., via an accelerometer or microphone). An acoustic signal have particular characteristics that are recognizable by the PIMD 802 may be generated by the PPC 800. For example, the acoustic signal may be encoded with a command signal and/or be of a particular frequency that would make this signal relatively unique yet detectable by the PIMD 802. An ultrasonic signal or an inductive signal, for example, may be used for this purpose. In one approach, the PPC 800 may be equipped with a sensor that senses a physiologic parameter of the patient when holding, or is in proximity with, the PPC 800. A heart rate sensor of the PPC 800, for example, may detect an abnormal heart rate and, in response, the PPC 800 may transmit a wake-up signal to the PIMD 802.

In another approach, the PPC 800 generates a signal that can be sensed by a lead/electrode arrangement of the PIMD 802. For example, a coded signal transmitted by the PIMD 802 may be sensed by the PIMD 802 via the PIMD's lead/electrode arrangement, filtered, and detected by the PIMD 802 as a wake-up signal. This approach has the advantage of not requiring any additional sensing or power usage by the PIMD, since sensing via its lead/electrode arrangement is a normal function.

A tiered wake-up/interrogation strategy may be implemented depending on needs of the particular patient or present condition of the patient. For example, one approach involves the PIMD 802 waking up in response to a fault condition or detection of a serious patient condition. Another approach involves establishing a PIMD/PPC connection whenever possible and terminating the connection after needed data is exchanged. A more power consuming approach involves maintaining a continuous connection between the PIMD 802 and PPC 800 whenever possible.

A wake-up or interrogation strategy may be implemented that involves determining the current status of the patient and/or time of day prior to effecting PIMD wake-up. For example, the PIMD 802 may detect patient sinus tachycardia indicative of normal elevated heart rate, such as due to exercise. An accelerometer of the PIMD 802 may detect patient activity level and/or posture. These and other sensors may be used by the PIMD 802 to determine whether effecting PIMD wake-up or interrogation would be appropriate based on the sensed status of the patient. This sensor information provides contextual information about the patient's current status that may indicate that PIMD wake-up/interrogation is or is not desirable or useful. For example, it may be necessary to obtain PIMD data each day when the patient is at rest. PIMD power may be conserved by the PIMD 802 first detecting when the patient is at rest prior to establishing a connection with the PPC 800, even if prompted by the PPC 800 or by a pre-scheduled timer signal.

PPC with SIM Card

A SIM card used in a PPC of the present invention may be configured to enhance manipulation by the patient. Today's SIM cards used in conventional cell phones are typically difficult to grasp and manipulate, particularly by older, impaired patients. A sleeve or carrier that engages or encompasses the SIM card may be used make the SIM card easier to handle. In another configuration, the SIM card or circuit may be permanently soldered to the PPC circuitry, thus preventing removal and/or swapping of the SIM cards from their designated PPCs. In one configuration, a silicon SIM card may be used, in which case stored SIM card data can be mapped to a SIM card of another PPC by the APM server.

Use of a SIM card in a PPC provides a convenient way for tracking PPC usage, allowing cellular network operators to bill for PPC usage based on SIM card usage information. There are a number of ways in which a PPC that incorporates a SIM card can be initiated into service. One approach involves forcing the SIM card into service on a specified date and time. Another approach involves activating SIM card usage the first time the SIM card detects a network connection. According to one automatic provisioning approach, a number of pre-activation processes involving the SIM card may be enabled by the cellular network provider on a no-charge basis.

For example, installation and testing of a SIM card with a PPC during manufacturing or distribution is preferably enabled by the cellular network provider without incurring charges. This allows the medical device manufacturer increased flexibility during build, installation, testing, and distribution phases. Another approach involves granting a "free" number of minutes to accommodate the manufacturer's needs during these phases (e.g., 15-60 minutes). Accordingly, the PPC is ready for instant activation, out-of-the-box, upon first transmission to the network. Network charges only begin accruing after this initial PPC activation event (or expiration of the predetermined "free" usage period). In one approach, the APM server may be configured by an ISP to allow the PPC to connect to the network.

A data block methodology may be used on a PPC's SIM card to provide enhanced security in cases of loss or theft of a patient's PPC. A unique key code, for example, may be stored on the PPC's SIM card for enhancing security. This unique key code can incorporate coded information based on a variety of data, including calibration parameters from manufacturing, use parameters, a copy of medical or device data from the PIMD stored on a SIM data block, special phone numbers, special network addresses, etc. Enhanced security pairing may be implemented so a designated SIM card is used only with a designated PPC.

Another approach may involve use of a bar code or other authorization code on the packaging of a new PPC, which can be input along with other needed information to authenticate and authorize use of the new PPC by the APM server. A further approach may involve shipping a new PPC with a depleted battery, so that the new PPC cannot be inadvertently turned on and activated other than by the designated patient. It is noted that initializing a PPC for connection with the APM server may be performed using a data channel of the cellular network rather than a voice channel. In current cellular networks, the data channel typically has better signal strength than the voice channel (i.e., 6 dB better signal strength than the voice or audio channel).

According to various embodiments, a SIM card is used to store information other than or in addition to data traditionally stored in SIM cards used in cellular phones. In this regard, such SIM or smart cards may be referred to more generically as identity cards or identity modules that are configured to store data for a variety or purposes in addition to providing for subscriber identification. For example, a number of configuration parameters may be stored on a SIM card that describes the various functions that can be performed by a particular PPC. The configuration parameters may define options and functions that may be selectively enabled and disabled. These configuration parameters, options, and/or functions may be embodied in a list of attribute/value pairs, or in an XML-based configuration file, for example.

Various software code may be stored in the SIM card and executed at predetermined times or under predetermined conditions. For example, software code stored on the SIM card can be executed during PPC initialization and reset processes. These processes may be related to PPC configuration or tailoring the PPC for specific tasks that a physician/clinic prescribes for that specific patient, such as by enabling/activating prescribed functionality and/or features. Software code may be stored on the SIM card for initiating and performing PPC service diagnostics. The SIM card provides a flexible facility to have relatively short scripts delivered to the PPC. These scripts may be configured to drive diagnostic code execution via an interpreter resident in the PPC firmware, for example, among other processes.

Figure 13:
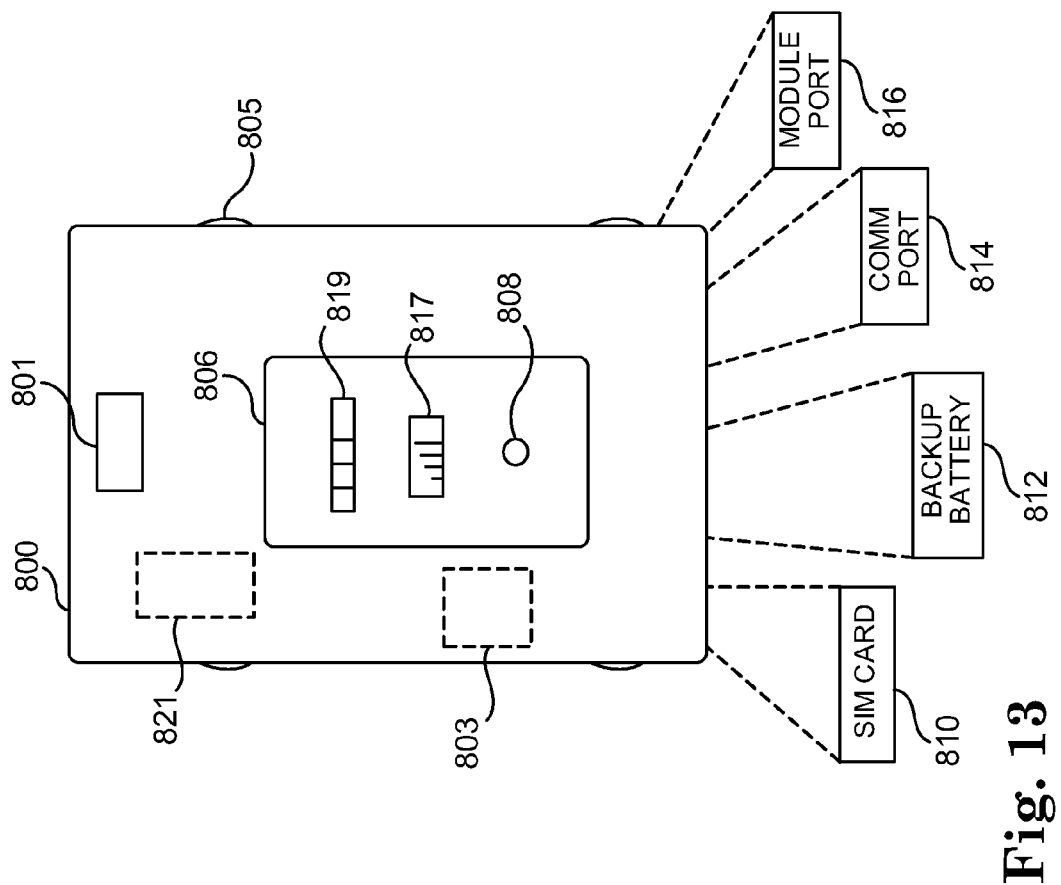
FIG. 13 shows a PPC configured to provide enhanced functionality by use of detachable or configurable modules in accordance with embodiments of the present invention.
Figure 13:
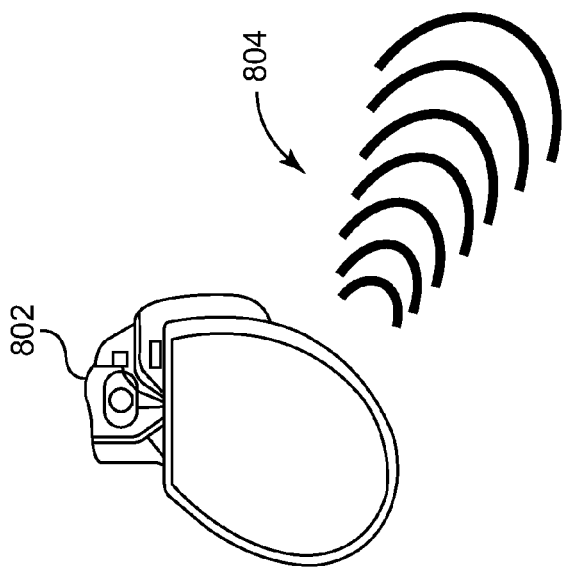

With reference to FIG. 13, for example, there is shown a PPC 800 configured to provide enhanced functionality. The PPC 800 shown in FIG. 13 preferably incorporates features in addition to those provided in a reduced feature set PPC. According to various embodiments, the PPC 800 may include a number of components and/or sensors, several non-limiting examples of which are shown in FIG. 13. The PPC 800 may, for example, incorporate a SIM card 810, which may store data unique to the PIMD 802 and/or the PPC 800 that is paired with the PIMD 802. Data stored in the SIM card 810 or other type of detachable smart card may store various types of data regarding the PIMD 802, PPC 800, and other patient-related data. Incorporation of a SIM card 810 in a PPC 800 of the present invention advantageously facilitates easy transferring of data stored in the SIM card 810 to another PPC 800, such as when upgrading to a different PPC 800 or when replacing a defective PPC 800. Use of a SIM card 810 may significantly reduce the amount of information needed to realize full operation of a newly paired PIMD 802 and PPC 800. It is noted that SIM card 810 may be configured to incorporate core cellular technology into the card itself (e.g., W-SIM), which may simplify the design of the PPC (and reduce cost of a PPC having a reduced feature set).

PPC with Physiologic Sensors

As is further shown in FIG. 13, the PPC 800 may also incorporate a module port 816 configured to receive a memory or processor module that allows for enhanced operation of the PPC 800. For example, the module port 816 may be configured to receive a memory module that provides increased storage for PIMD data, such as cardiac event data, EGM or ECG waveforms, cardiac signal templates, diagnostic data, and the like. For example, attachment of a memory module to the module port 816 allows a greater volume of PIMD data to be buffered by the PPC 800 during extended periods of non-communication between the PPC 800 and an APM server (e.g., due to weak or inadequate cellular connections, no-service locations, periods of high network traffic, etc.).

The PPC 800 shown in FIG. 13 includes one or more physiologic sensors configured to sense one or more physiologic parameters of the patient. For example, the sensors 805 may include metallic sensors for contacting with the patient's skin through which the patient's heartbeat is acquired. The sensors 805 are coupled to electronics (e.g., amplifies, filters, signal processors, and/or other circuitry) that provide a heartbeat signal detector within the PPC 800. The PPC 800 may be equipped with other sensors for sensing any type of physiological data, including an accelerometer, microphone (e.g., heart sounds and/or lung sounds monitor when the PPC 800 is held near the heart), a posture sensor, motion sensor, pulse oximeter, photoplethysmography sensor, a body weight, fat or fluid change sensing arrangement, optical or photonic blood chemistry sensors, blood pressure sensors, and body temperature sensors, among others. As was discussed previously, one or more of these sensors may be used during a pairing operation. Ambient condition sensors may also be incorporated in the PPC 800, such as an ambient temperature, pressure, and/or hygrometer sensor.

Time stamp data may be appended to sensor data and/or an event marker may be appended to sensor data that results from patient actuation of a PPC button when an event is felt by the patient. This aids in time correlating sensor data to other physiologic data and contextual events. Timing (e.g., clock time) used by the PIMD 802 and PPC 800 may be coordinated or synchronized using various time/clock standards, such as APM server time, PIMD clock time, programmer clock time, time zone time based on geographical location of the PPC 800, time indicated by cellular infrastructure, or other standard.

As is shown in FIG. 13, weight, fat or fluid monitoring circuitry within the PPC 800 may be coupled to a number of metallic skin contacts or electrodes 805 that provide for physical and electrical coupling between portions of the user's anatomy and the monitoring circuitry of the PPC 800. According to one arrangement, two electrodes 805 serve as source electrodes and two electrodes 805 serve as detection electrodes. In general terms, changes in body weight, fat or fluid may be determined by measuring changes in the resistance of the body to an injected monitoring signal using a four point probe technique. The monitoring circuitry includes a monitoring signal generator, which is typically a current or voltage source that provides a constant current or voltage monitoring signal. The monitor signal generator is coupled to the two source electrodes 805. The monitoring circuitry further includes a voltage detector which is coupled between the two detection electrodes 805. The voltage detector typically receives an input reference signal from the monitoring signal generator. The monitoring signal generator preferably generates an AC drive current signal. The drive current signal can be a sinusoidal signal or a square wave.

A monitoring signal generated by the monitoring signal generator is injected into the user's body via the source electrodes 805. A current field is produced between the source electrodes 805 in response to propagation of the monitoring signal into the user's body tissue. The detection electrodes 805 are situated such that the current field is detectable. A sense voltage is developed between the detection electrodes 805 and measured by the voltage detector. An impedance, $Z_{bio}$, may be derived using the sense voltage and source current amperage. The derived impedance value is reflective of a biological resistance and reactance (i.e., bioimpedance, $Z_{bio}$) measurable between the detection electrodes 805 in response to the monitoring signals injected into biological tissue by the source electrodes 204. Changes in sense voltage or bioimpedance may be correlated to changes in body weight, fat or fluid, which may be particularly useful when monitoring patient heart failure status, for example.

The PPC 800 shown in FIG. 13 may include one or more acceleration sensors 803 coupled to a microcontroller or processor of the PPC 800. An acceleration sensor 803 may be used for a variety of purposes, including posture sensing, activity sensing, heart rate sensing, heart sound sensing, and as a step counter of a pedometer for counting steps taken by a user during walking or running. Inclusion of one or more acceleration sensors 803 provides a number of pedometer functions, including step counting, distance computations, and caloric consumption calculations. By entering the user's stride length and weight into memory of the PPC 800, for example, the processor of the PPC 800 can calculate various statistics of interest, including total distance traveled, total calories burned, speed, elapsed time, and steps per minute. As discussed previously, inclusion of pedometer functionality into the PPC 800 may provide an incentive for the patient to continuously carry (or remember to carry) the PPC 800.

PPC with Rechargeable Hub

Figure 14:
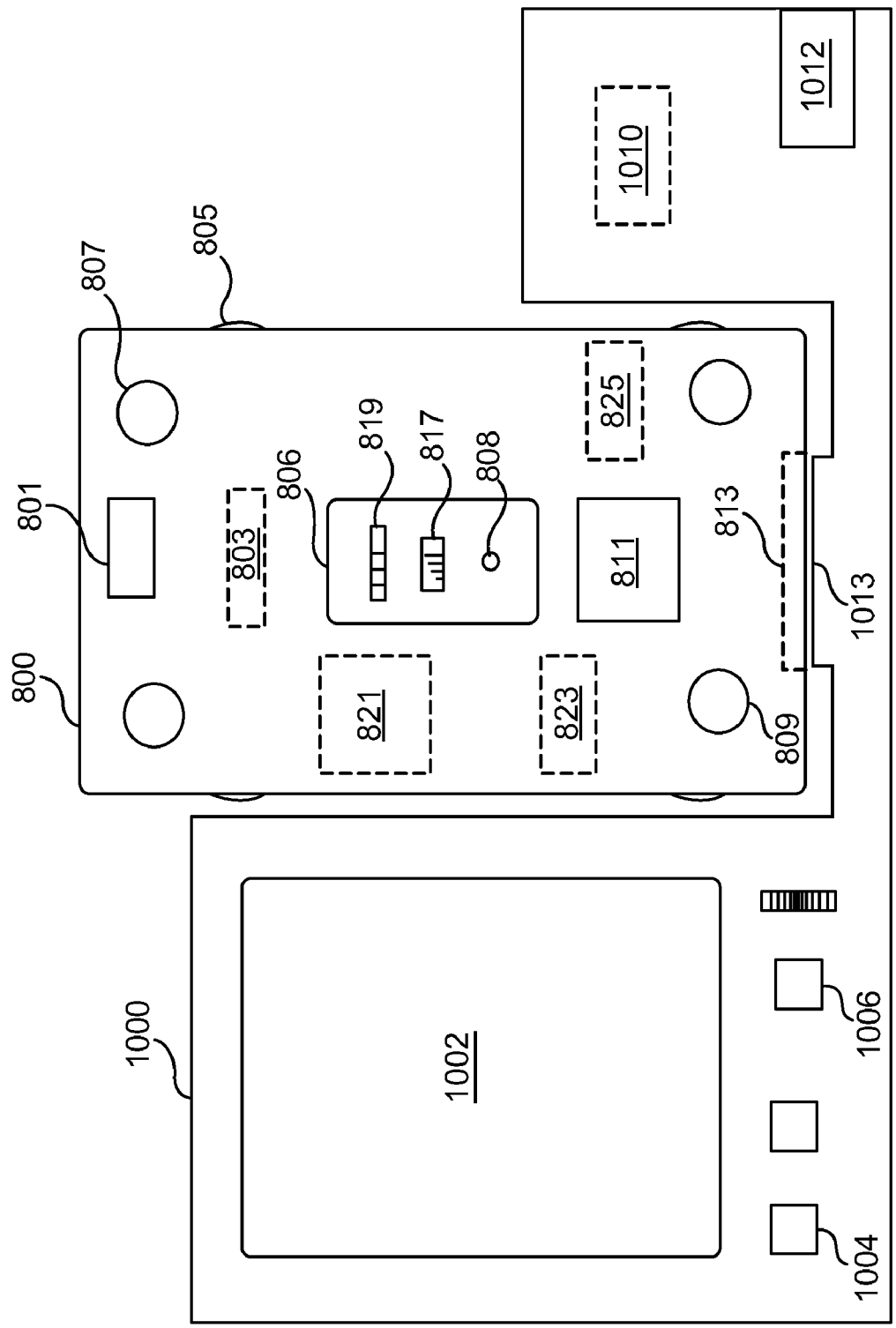
FIG. 14 shows a base station or hub that is configured to physically and electrically receive a PPC in accordance with embodiments of the present invention.

FIG. 14 shows a base station or hub 1000 that is configured to physically and electrically receive the PPC 800. The hub 1000 includes a power cord and connector for connecting with a standard wall socket (e.g., 110-120V, 60 Hz household power source). The hub 1000 may alternatively or additionally include power circuitry appropriate for a 220V/50 Hz power source or other power source, as is widely used in Europe. The power supply circuitry of the hub 1000 may be configured to automatically sense the voltage of the power source and automatically switch appropriate circuitry to safely couple to the power source, which is particularly useful when traveling between the United States and Europe, for example.

The hub 1000 may also include a telephone, modem, or network communications interface 1012 that allows for connection to a traditional land line (e.g., POTS or cable) communication link. The hub 1000 may incorporate or be connectable to a Wi-Fi node/wireless access point for communicating with a household Wi-Fi system. The hub 1000 may also include an antenna arrangement that can be used to increase the antenna range for the PIMD, such as for PIMD interrogation. The antenna arrangement of the hub 1000 may also be configured to host Bluetooth or other communication paths between the hub 1000 and one or more external sensors and/or between the PIMD and one or more external sensors. The hub 1000 preferably includes the same radios as are included in the PPC 800.

The hub 1000 is shown to include a display 1002. The display may be configured to display text and graphics (e.g., LCD or OLED), such as data and waveforms received from the PPC 800. The hub 1000 may include one or more status indicators 1004 and one or more user interface buttons or controls 1006. The hub 100 may also include or couple to one or more physiologic sensors that can acquire physiologic signals from the patient. Such sensors include a blood pressure cuff arrangement, weight scale, pulse oximetry sensor, thermometer, and heart rate monitor, among others. Data acquired by such sensors may be stored by the hub 1000 and/or transferred to an APM server. The hub 1000 may include an array of Bluetooth transceivers and/or transceiver connectors (built-in and/or external) to allow for an expanded number of sensors to communicate with the hub 1000. Time stamp data may be appended to the sensor and PPC data, which preferably includes unique ID data (e.g., SIM card ID, PIMD ID), and may also include ID of the hub 1000 and/or PPC 800 or a combination of these ID data.

A connector 1013 of the hub 1000 is configured to receive a corresponding connector 813 of the PPC 800. Mating engagement of the two connectors 813, 1013 establishes data connectivity and, preferably, power connectivity between the hub 1000 and the PPC 800. The two connectors 813, 1013 may be USB connectors. For example, power is delivered to the PPC 800 when the connector 813 of PPC 800 is mated to the connector 1013 of the hub 1000, thereby recharging the rechargeable battery of the PPC 800 (e.g., lithium ion, lithium polymer, or nickel metal hydride battery). Mating engagement of the two connectors 813, 1013 facilitates transfer to data and power between the PPC 800 and the hub 1000. The hub 1000 may be programmed to initiate charge/discharge cycling of the PPC 800 to promote extended PPC battery life.

PIMD data acquired by the PPC 800 during ambulatory use by the patient may be transferred to a memory 1010 of the hub 1000. This data may be transferred to an APM server via the communications interface 1012. It is understood that a local wireless communication link may also be established between the PPC 800 and hub 1000 using components and protocols discussed previously, in which case a simple power connector between the PPC 800 and hub 1000 may be used to recharge the battery of PPC 800. It is further understood that the PPC 800 may be capable of providing full functionality while seated in the hub 1000. Alternatively, selected functionality may be enabled or disabled when the PPC 800 is seated in the hub 1000.

The PPC 800 shown in FIG. 14 includes various features that may be considered optional. The PPC 800 is shown to include an optical emitter/detector 811 that may be used to facilitate pulse oximetry or photoplethysmography sensing. For example, the patient may simply place a finger or thumb over the optical emitter/detector 811 and push button 801 to initiate an optical sensing procedure. The circular sensors 807 and 809 may represent other types of sensors that may incorporated in the PPC 800, such as those previously described. For example, the upper two sensors 807 and lower two sensor 809 may represent metal contact sensors that may replace or compliment the sensors 805 disposed on the sides of the PPC 800. The PPC 800 may provide wireless or wired connectivity with other patient sensors, such as a Holter monitor or other physiologic sensor separate from the PPC 800. The PPC 800 may itself define a Holter monitor, with sensors being connected to the PPC 800 at an appropriate wired or wireless interface.

The PPC 800 shown in FIG. 14 includes a simple display 806, which includes a battery indicator 819, a signal strength indicator 817, and a push button 801. The PPC 800 may also include an alert module 823 that generates an alert signal in response to a condition requiring immediate attention. The alert module 823 may be coupled to a visual, audible or vibratory component of the PPC 800. The alert module 823 may also be configured to transmit a message to the patient's cell phone, pager, the hub 1000, or the APM server 850 in response to an alert condition. PPC 800 includes a memory 825, which may be configured to store various firmware, software, and data, including software that facilitates pairing of a PIMD 802 with a PPC 800.

The hub 1000 may incorporate a number of features that can enhance management of PIMD and PPC power resources. For example, the PIMD 802 may monitor its battery capacity relative to a threshold. When the battery capacity falls below this threshold, as detected by the PIMD 802, PPC 800 or hub 1000, the hub 1000 or the PPC 800 automatically initiates a call or dispatches a message via any available mechanism to the APM server 850 alerting the server that the PIMD battery is nearing depletion. The PPC 800 or hub 1000 may also make an automatic call to the patient's cell phone, home phone, or advocate's phone, such as a physician's office phone. The threshold is preferably established to allow enough time for the call or message to be dispatched and responded to by the APM service, which includes time for the patient to travel to a hospital or care facility.

The hub 1000 or PPC 800 may be programmed to trend the charge history of the PPC 800 and evaluate the health of the PPC's battery. If the charging trend indicates the PPC's battery is failing, a call or message may be communicated by the PPC 800 or hub 1000 to the APM server 850 that the PPC's battery requires replacement or evaluation. The PPC battery may be replaced the next time the patient visits his or her physician, for example. A call may be placed by the PPC 800 or hub 1000 ahead of the patient's office visit to indicate that PPC battery replacement is needed, allowing the office to obtain the necessary battery in time for the patient's visit. A signal or light on the hub 1000 and/or PPC 800 may be illuminated to indicate that a new battery is needed based on the history/trend data. The hub 1000 preferably tracks the battery charge status of PPC 800 and knows how much PPC usage time is left (e.g., x=13 hours). The hub 1000 may be programmed to initiate a call to the patient's home or cell phone to indicate that the PPC's battery needs to be charged.

The hub 1000 may include an indicator that beeps or flashes to indicate to the patient that the PPC 800 has not been cradled on the hub 1000 for x days or hours. This indicator prompts the patient to connect the PPC 800 to the hub 1000 for recharging and any needed or desirable data exchange between the PPC 800/hub 1000/APM server 850. The hub 1000 may use a USB connector, for example, that connects with and provides power to the PPC 800 when cradled on the hub 1000.

Multiple hubs 1000 may be used in the same home or facility. Multiple hubs 1000 provides the opportunity to perform enhance functions, such as performing SIM to SIM transfers for replacing PPCs 800 having poor performance. Multiple PPC slots may be provided in a single hub 1000, allowing a single hub 1000 to provide hub functionality (e.g., landline link to the APM server 850) for multiple PPCs 800.

As was discussed previously, the hub 1000 can communicate with the APM server 850 to acquire updates for the PPC 800 before the patient returns home, so that the update is immediately available when the PPC 800 is cradled on the hub 1000. A touch screen 1002 of the hub 1000 may, for example, be provided to facilitate patient interaction with the hub 1000, such as to verify updates from the APM server 850 to the PPC 800. The APM server 850 may provide alerts to the hub 1000 that are to be downloaded to the PIMD 802 via the PPC 800/hub 1000. In one approach, programming changes to the PIMD 802 may only be instigated when the PPC 800 is set in the cradle of the hub 1000. The hub 1000 may be locked in or out when the PPC 800 is seated (e.g., during remote programming). An indicator of an addition or change to PIMD alerts or software may be communicated to the patient via the hub 1000, and patient authorization or consent to make the programming change may be given by patient actuation of an approval or PIMD update button.

The hub 1000 may be implemented to provide additional features. For example, the hub 1000 may be used by the patient's caregiver to communicate with the APM system 850 and/or PPC 800 via the hub's user interface devices. The hub 1000 may include a backup power supply that provides power to the PPC 800 and hub 1000 if local line power is interrupted or lost. The backup power supply may be sufficiently large to provide recharging for the PPC's battery. The hub 1000 may have a backup memory that stores the latest firmware, setting, and configuration data (e.g., redundant configuration data/ firmware) for the PPC 800 and/or PIMD 802, which can be accessed as part of a quick recovery mechanism. The hub 1000 may include a "locate PPC feature" that includes a button that, when actuated, transmits a "find signal" to the PPC to assist the patient/caregiver in locating the PPC.

The hub 1000 may incorporate voice synthesizer circuitry or voice file playback circuitry to convert voice/audio files to human speech. Audio messaging may be uni-directional or bi-directional as between the hub 1000 and the APM server 850. For example, messages transferred from a physician, clinician, or technician (e.g., employee of the APM service) via the APM system 850 to the hub 1000 may be played back in human speech form by audio circuitry/components of the hub 1000. Audio files may be transferred in WAV or MP3 format, for example. The hub 1000 may allow the patient or caregiver to record messages and transmit these messages to a recipient via the APM server 850. A "live" audio session between the patient/caregiver and the physician, clinician, or technician may be implemented using a landline connection, wireless connection, or voice-over-Internet connection established using the hub 1000.

Software Architecture

Figure 15:
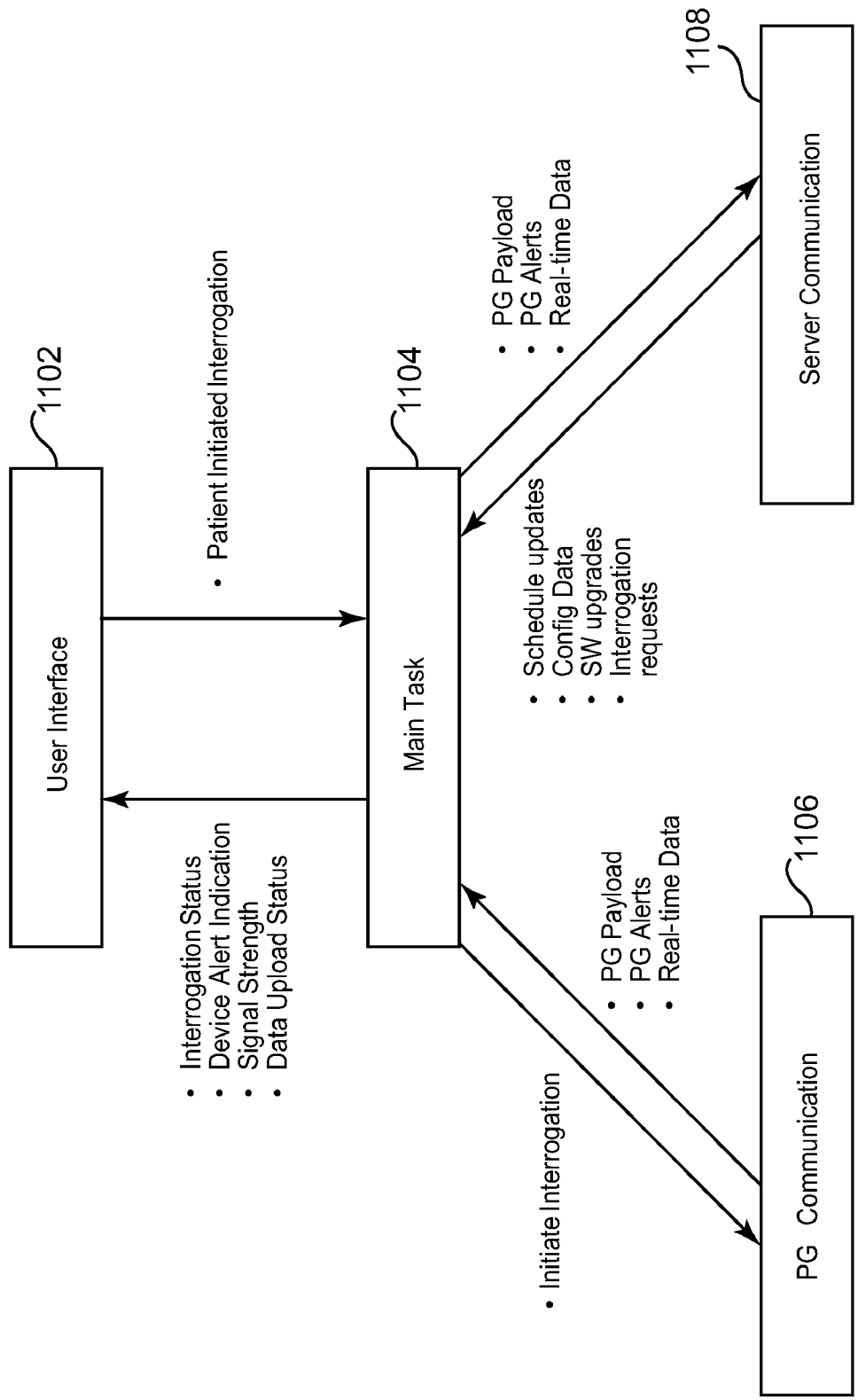
FIG. 15 is a high level software architectural overview that shows the relationships between various LCN tasks and the events and information that flow between these tasks in accordance with embodiments of the present invention.
Figure 16:
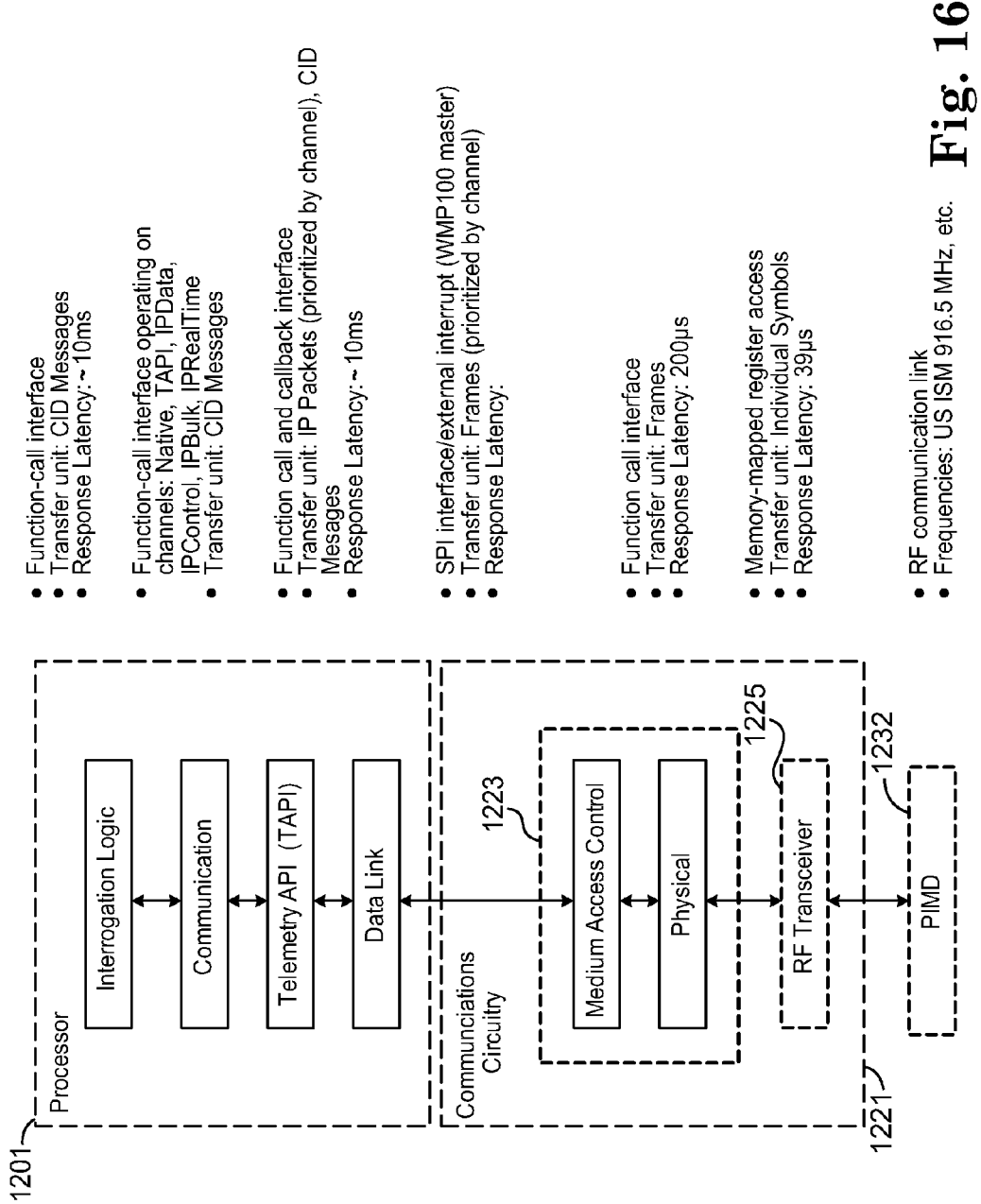
FIG. 16 shows the layering of functional blocks within a PIMD communications protocol stack in accordance with embodiments of the present invention.
Figure 17:
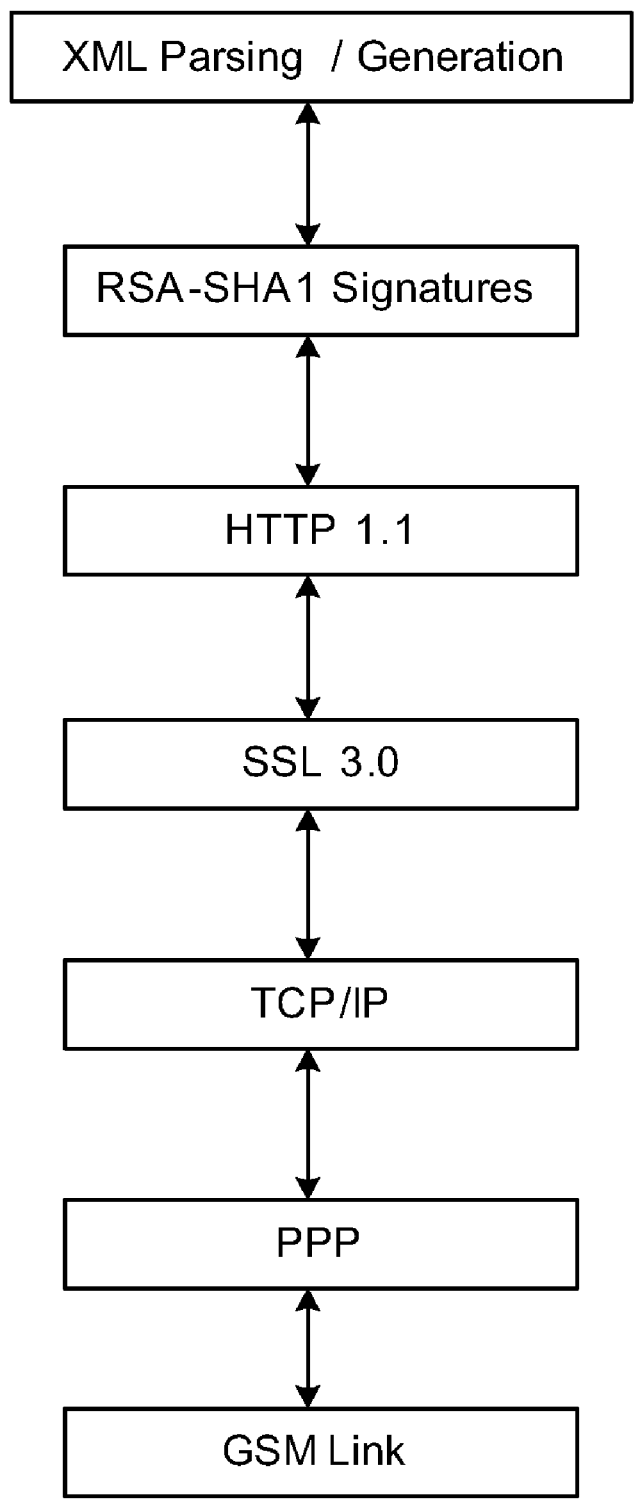
FIG. 17 shows server communications in functional block diagram form in accordance with embodiments of the invention.

FIGS. 15-17 provide an overview of software architecture for a PPC in accordance with embodiments of the invention. In general, the PPC is responsible for interrogating status and data from the PIMD (e.g., implantable pulse generator or PG) and relaying the information to the APM server. The PIMD interrogation is preferably initiated on a regular basis according to a predetermined schedule, at the request of the clinician via the APM server, or at the request of a patient via a button on the PPC. The PPC must also periodically contact the APM server to get any updates to the schedule, configuration, software, or communicator status. Server-initiated connections are desirable for the PPC, which can be implemented using a server-push paradigm, rather than a PPC-pull paradigm.

FIG. 15 is a high level software architectural overview that shows the relationships between various tasks and the events and information that flow between these tasks. FIG. 15 shows the main PPC software tasks including the main tasks of monitoring the interrogation schedule 1104, performing PIMD (e.g., PG) communications 1106, performing server communications 1108, and interacting with the user interface 1102. It is understood that the term "task" used in the context of the PPC software architecture does not necessarily imply a task in the sense of a separate thread of execution within the system. It is used here as a generic term for the partitioning of the functional duties of the software. The timing granularity and responsiveness of all operations at this architectural level are preferably on the order of hundreds of milliseconds.

The main task 1104 involves monitoring the PPC schedule for scheduled PIMD interrogations or APM server communications. Another main task 1104 is monitoring the PPC user interface for patient-initiated interrogations. The main task 1104 is responsible for initiating and monitoring PIMD interrogations, initiating and monitoring APM server communications, and accepting APM server communication requests. The timing granularity and responsiveness of all main task operations are preferably on the order of 100 ms. Persistence requirements include PPC schedule and software version information.

Responsibilities of PIMD (e.g., PG) communications task 1106 include initiating a PIMD communication session via RF telemetry, interrogating status and data from the PIMD, streaming real-time data from the PIMD, including EGM and marker data, and terminating the PIMD communication session. Concerning timing requirements according to various implementations, the physical layer protocol may require the ability to service a symbol every 39 μs. The physical layer protocol may require the ability to process a frame and be ready for the next frame within about 50 μs of processing time (i.e., the link turnaround time). Persistence requirements, according to various embodiments, may include PIMD session credentials, such as model number, serial number, wakeup access code, permanent HMAC key, and PIMD center frequency. Persistence requirements may also include PIMD payload results, which may be on the order of 100 to 300 KB each, up to three payloads.

In accordance with some embodiments, the PIMD communications task 1106 of the PPC may be implemented using a serial peripheral interface bus (SPI), a microprocessor with wireless functionality, such as Wireless Microprocessor Model No. WMP100 manufactured by Wavecom S. A. of Issy-les-Moulineaux Cedex, France, and a radio transceiver chip, such as Model No. CC1110 available from ChipCon or Texas Instruments. An external interrupt is provided into the WMP100, and one general purpose Input/Output (GPIO) line out of the WMP100 is provided to communicate with the CC1110 transceiver chip. The WMP100 is preferably the SPI master. The CC1110 raises an interrupt into the WMP100 when it has data to send. The WMP100 drives the GPIO line to control the operating state of the CC1110.

The layering of the functional blocks within the PIMD communications protocol stack is depicted in FIG. 16. FIG. 16 shows how the functionality is mapped onto the processor 1201 and communications circuitry 1121 of the PPC in the "two-chip" embodiment shown in FIG. 16. It is noted that the timing requirements become tighter as one moves down the protocol stack. The elements 1201, 1221, 1223 (Intel 8051 processor), 1225 (ChipCon RF transceiver), and 1232 shown in dashed lines in FIG. 16 indicate hardware components. The solid boxes of the processor 1201 and those in the communications circuitry 1221 indicate individual software modules within the PIMD communications software component.

Responsibilities of the server communications task 1108 include establishing or accepting an SSL connection to/from the APM server, accepting configuration, schedule, software version, and other data from the APM server, and uploading PIMD interrogation data to the APM server. Other server communications task responsibilities include supporting real-time data streaming to the APM server or other destination application, and terminating the APM server connection. Concerning timing requirements, all interactions are preferably be on the order of 100 ms, as previously discussed. Persistence requirements include APM server contact information (URL, username, password), APM server credentials (authentication certificates), and PPC credentials (authentication certificates), among others.

According to some embodiments, the user interface of the PPC is of minimal complexity, and may include one or two buttons, a few LED's, possibly a very simple display, and possibly a buzzer. Responsibilities of the user interface task 1102 include indicating interrogation status, signal strength, and data upload status, providing device alert indications, and facilitate patient-initiated interrogation.

FIG. 17 shows server communications in functional block diagram form in accordance with embodiments of the invention. In accordance with various embodiments, particularly those that incorporate a wireless microprocessor such as the Wavecom WMP 100, desirable or useful device driver and support features may include the following software support and hardware peripherals, as is shown in FIG. 17. Software support features according to some embodiments may include XML parsing/generation; digital signature verification/generation (RSA SHA-1); HTTP 1.1; SSL 3.0; TCP/IP; PPP (TCP over point to point protocol); a GSM link; and flash storage access for persistent state data. Hardware peripherals and features according to some embodiments may include: user interface—buttons, LEDs, SPI—one master, battery charging/management, USB device or host/on-the-go interface, serial interface to POTS/cell modem, Ethernet interface (optionally), very low interrupt latency, and a timer granularity that provides frequent updating, such as every 20 ms.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A portable patient communicator (PPC) for communicating with a patient implantable medical device (PIMD) and facilitating communications with a remote server via a wireless network, the wireless network supporting a plurality of disparate data transport mechanisms having differing characteristics, the PPC comprising:
   a housing configured for portability by an ambulatory patient;
   a processor coupled to memory, the processor and the memory provided in the housing, the memory storing wireless radio firmware, medical firmware, and data transfer instructions, the data transfer instructions executable by the processor for transferring preselected data to the remote server in accordance with a priority level;
   a first radio provided in the housing and configured to effect communications with the PIMD in accordance with program instructions of the medical firmware executable by the processor;
   a second radio provided in the housing and configured to effect communications via the wireless network in accordance with program instructions of the wireless radio firmware executable by the processor; and
   a power source provided in the housing and configured to supply power for components of the PPC;
   the processor configured to determine whether the preselected data is available in the memory of the PPC or the PIMD, and if available, the processor configured to execute program instructions for selecting a data transport mechanism among the plurality of disparate data transport mechanisms based at least in part on the priority level and transmitting the preselected data to the wireless network using the selected transport mechanism via the second radio.

2. The communicator of claim 1, wherein the preselected data comprises clinician requested data.

3. The communicator of claim 1, wherein the preselected data comprises specified patient data.

4. The communicator of claim 1, wherein the preselected data comprises specified clinical event data.

5. The communicator of claim 1, wherein the preselected data comprises specified arrhythmia data.

6. The communicator of claim 1, wherein the preselected data comprises specified episode or alert data.

7. The communicator of claim 1, wherein the preselected data comprises specified PIMD operating status data.

8. The communicator of claim 1, wherein the PPC is configured to connect with the remote server and determine if and what preselected data is to be acquired from the PIMD prior to establishing communications with the PIMD.

9. The communicator of claim 8, wherein the PPC is configured to connect with the remote server immediately prior to establishing communications with the PIMD in response to a high priority level.

10. The communicator of claim 8, wherein the PPC is configured to connect with the remote server at an off-peak time prior to establishing communications with the PIMD in response to a low priority level.

11. The communicator of claim 1, wherein the PIMD is configured to tag the preselected data for transfer to the PPC in response to occurrence of a predetermined event.

12. The communicator of claim 1, wherein:
   the PIMD is configured to push the preselected data to the PPC in response to occurrence of a predetermined event; and
   the PPC is configured to connect with the remote server in response to receiving the pushed preselected data.

13. The communicator of claim 1, wherein the PPC is configured to transmit portions of the preselected data at different times based on the priority level.

14. A portable patient communicator (PPC) for communicating with a patient implantable medical device (PIMD) and facilitating communications with a remote server via a wireless network, the wireless network supporting a plurality of disparate data transport mechanisms having differing characteristics, the PPC comprising:
   a housing configured for portability by an ambulatory patient;
   a processor coupled to memory, the processor and the memory provided in the housing, the memory storing wireless radio firmware and medical firmware;
   a first radio provided in the housing and configured to effect communications with the PIMD in accordance with program instructions of the medical firmware executable by the processor;
   a second radio provided in the housing and configured to effect communications via the wireless network in accordance with program instructions of the wireless radio firmware executable by the processor; and
   a power source provided in the housing and configured to supply power for components of the PPC;
   the processor configured to receive data from the PIMD via the first radio to which a priority level is assigned, the processor configured to execute program instructions for selecting a data transport mechanism among the plurality of disparate data transport mechanisms based at least in part on the priority level and transmitting the PIMD data to the wireless network using the selected transport mechanism via the second radio; and
   at a time subsequent to transmission of the PIMD data to the wireless network, retransmitting the PIMD data from the PIMD to the wireless network if it is determined that the previously transmitted PIMD data was not received by the remote server.

15. The communicator of claim 14, wherein the PIMD data comprises preselected patient data requested by a clinician.

16. The communicator of claim 14, wherein the PIMD communicates with the remote server via an external medical system to cooperatively determine whether or not the previously transmitted PIMD data was received by the remote server.

17. The communicator of claim 16, wherein the external medical system comprises a PIMD programmer.

18. The communicator of claim 14, wherein the priority level is determined at least in part by the PPC or the PIMD.

19. The communicator of claim 14, wherein the priority is based at least in part on criticality of a patient's condition as detected by the PIMD.

20. The communicator of claim 14, wherein the processor is configured to establish a connection with the wireless network on an unscheduled event driven basis.

* * * * *